US007608443B2

(12) United States Patent
Kinney et al.

(10) Patent No.: US 7,608,443 B2
(45) Date of Patent: Oct. 27, 2009

(54) LYSOPHOSPHATIDIC ACID ACETYLTRANSFERASES

(75) Inventors: Anthony J. Kinney, Wilmington, DE (US); Rebecca E. Cahoon, Webster Groves, MO (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/820,045

(22) Filed: Jun. 18, 2007

(65) Prior Publication Data

US 2008/0010699 A1    Jan. 10, 2008

Related U.S. Application Data

(62) Division of application No. 11/009,658, filed on Dec. 10, 2004, now Pat. No. 7,235,714, which is a division of application No. 09/914,098, filed as application No. PCT/US00/04526 on Feb. 22, 2000, now Pat. No. 6,855,863.

(60) Provisional application No. 60/121,119, filed on Feb. 22, 1999.

(51) Int. Cl.
*C12N 9/00* (2006.01)
*C12N 9/10* (2006.01)
*C12N 1/20* (2006.01)
*C12N 15/00* (2006.01)
*C07H 21/04* (2006.01)

(52) U.S. Cl. .................... 435/193; 435/183; 435/252.3; 435/320.1; 536/23.2

(58) Field of Classification Search ........................ None
See application file for complete search history.

(56) References Cited

FOREIGN PATENT DOCUMENTS

| WO | WO 95/27791 A1 | 10/1995 |
| WO | WO 96/24674 A1 | 8/1996 |
| WO | WO 00/18889 A2 | 4/2000 |
| WO | WO 00/49156 | 8/2000 |
| WO | WO2007/100789 A2 | 9/2007 |

OTHER PUBLICATIONS

Whisstock et al. Q Rev Biophys. Aug. 2003;36(3):307-40.*
Liu et al. Amino Acids. Oct. 2008;35(3):627-50. Epub Apr. 18, 2008.*
Thornton et al. Nat Struct Biol. Nov. 2000;7 Suppl:991-4.*
Margrit Frentzen et al., Structure, function and metabolism of plant lipids; Siegenthaler and Eichenberger, eds., pp. 105-110, 1984, Properties of the Microsomal Glycerol 3-P and Monoacylglycerol 3-P Acyltransferase from Leaves.
Adrian P. Brown et. al., Plant Molecular Biology, vol. 29:267-278, 1995, Identification of a cDNA That Encodes A 1-Acyl-SN-Glycerol-3-Phosphate Acyltransferase From Limnanthes Douglasii.

National Center for Biotechnology Information General Identifier No. 3878960, Jun. 20, 2001, Cottage, A., Genome Sequence of the Nematode *C. elegans*: a Platform for Investigating Biolog.
*C. elegans*: Sequence to Biology, Science, vol. 282:2012-2018, 1998, Genome Sequence of the Nematode *C. elegans*: a Platform for Investigating Biology.
National Center for Biotechnology Information General No. 2317725, Aug. 9, 1997, Stamps, M. et al.
National Center for Biotechnology Information General No. 3135672, Jan. 19, 1999, Deshazer, D., et. al. The Type II O-Antigenic Polysaccharide Moiety of Burkholderia Pseudomallei Lipopolysaccharide is Required for Serum Resistance and Virulence.
David Deshazer et. al., Molecular Microbiology, vol. 30(5):1081-1100, 1998, the Typr II O-Antigenic Polysaccharide Moiety of Burkholderia Pseudomallei Lipopolysaccharide is Required for Serum Resistance and Virulence.
National Center for Biotechnology Information General No. 6503307, Dec. 2, 1999, Schwartz, J.R. et. al., Arabidopsis Thaliana Chromosome 1 Bac F23A5 Sequence.
National Center for Biotechnology Information General No. 2979560. Apr. 5, 2000. Lin. X. et. al. Sequence and Analysis of Chromosome 2 of the Plant *Arabidopsis thaliana*.
Xiaoying Lin et. al., Nature, vol. 402:761-768. 1999. Sequence and Analysis of Chromosome 2 of the Plant *Arabidopsis thaliana*.
National Center for Biotechnology Information General No. 575960, Brown, A.P. et. al., Isolaltion and Characterization of a Maize cDNA That Complements a 1-Acyl SN-Glycerol-3-Phosphate Acyltransferase Mutant of *Escherichia coli* and Encodes a Protein Which has Similarities to Other Acyltransferases.
National Center for Biotechnology Information General No. 1076821, May 19, 2000, Brown, A.P. et. al., Isolation and Characterization of a Maize cDNA That Complements a 1-Acyl SN-Glycerol-3-Phosphate Acyltransferase Mutant of *Esherichia coli* and Encodes a Protein Which has Similarities to Other Acytransferases.
J. Cao et al., Molecular identification of microsomal acyl-CoA:glycerol-3-phosphate acyltransferase, a key enzyme in de novo triacylglycerol synthesis, vol. 103(52), pp. 19695-19700, Dec. 26, 2006.
J. Cao et al., Molecular identification of microsomal acyl-CoA:glycerol-3-phosphate acyltransferase, a key enzyme in de novo triacylglycerol synthesis. vol. 103(52), pp. 19695-19700, Dec. 14, 2006.
National Center for Biotechnology Information General No. 575960, Brown, A.P. et. al., Isolaltion and Characterization of a Maize cDNA That Complements a 1-Acyl SN-Glycerol-3-Phosphate Acyltransferase Mutant of *Escherichia coli* and Encodes a Protein Which has Similarities to Other Acyltransferases, (Nov. 17, 1994).
National Center for Biotechnology Information General Identifier No. 4583544, Apr. 5, 1999, Graefin Zu Muenster, A., et. al., A cDNA Encoding a Microsomal 1-Acylglycerol-3-Phosphate Acyltransferase of *Brassica nupus L*.

(Continued)

*Primary Examiner*—Christian L Fronda

(57) ABSTRACT

An isolated nucleic acid fragment encoding an LPAAT isozyme is disclosed. Construction of a chimeric gene encoding all or a portion of the LPAAT isozyme, in sense or antisense orientation, wherein expression of the chimeric gene results in production of altered levels of the LPAAT isozyme in a transformed host cell is also disclosed.

12 Claims, No Drawings

OTHER PUBLICATIONS

Adrian P. Brown et. al., Plant Molecular Biology, vol. 26:211-223, 1994, Isolation and Characterisation of a Maize cDNA That Complements a 1-Acyl SN-Glycerol-3-Phosphate Acyltransferase Mutant of *Escherichia coli* and Encodes a Protein Which has Similarities to Other Acyltransferases.

Jitao Zou et. al., The Plant Cell, vol. 9:909-923, 1997, Modification of Seed Oil Content and Acyl Composition in the Brassicaceae by Expression of a Yeast SN-2 Acyltransferase Gene.

EMBL Sequence Library Database Accession No. AW065739, Oct. 18, 1999, V. Walbot, Maize Ests From Various cDNA Libraries Sequenced at Stanford University.

EMBL Sequence Library Database Accession No. AI939764, Aug. 4, 1999, V. Walbot, Maize Ests From Various cDNA Libraries Sequenced at Stanford University.

EMBL Sequence Library Database Accession No. AW055524, Sep. 26, 1999, V. Walbot, Maize Ests From Various cDNA Libraries Sequenced at Stanford University.

EMBL Sequence Library Database Accession No. AI783420, Jul. 2, 1999, Walbot V., Maize Ests From Various cDNA Libraries Sequenced at Stanford University.

* cited by examiner ic acyltransferase (EC 2.3.1.51), also called
LYSOPHATIDIC ACID ACETYLTRANSFERASES This application is a divisional of U.S. patent application Ser. No. 11/009,658 filed Dec. 10, 2004, issued as U.S. Pat. No. 7,235,714, which is a divisional of U.S. patent application Ser. No. 09/914,098 filed Aug. 22, 2001, issued as U.S. Pat. No. 6,855,863, which is a national stage filing of PCT Application No. PCT/US00/04526 filed Feb. 22, 2000, now abandoned, which claims the benefit of U.S. Provisional Application No. 60/121,119, filed Feb. 22, 1999. The entire content of each of these Specifications is incorporated herein by reference.

FIELD OF THE INVENTION

This invention is in the field of plant molecular biology and, in particular, this invention pertains to isolated polynucleotides encoding lysophosphatidic acid acyltransferases in plants and seeds.

BACKGROUND OF THE INVENTION

Triacylglycerols are nonpolar, water-insoluble fatty acid triesters of glycerols. Triacylglycerols differ according to the identity and placement of their three fatty acid residues. Lysophosphatidic acid acyltransferase (EC 2.3.1.51), also called 1-acyl-sn-glycerol-3-phosphate acyltransferase, 1-AGP acyltransferase, 1-AGPAT, lysophosphatidic acid transferase, and LPAAT, catalyzes the attachment of the second acyl group to the glycerol backbone during de-novo biosynthesis of triacylglycerols.

The fatty acid distribution in triacylglycerols is thought to be dependent on the specificities of the acyltransferases involved in their biosynthesis. Although no plant LPAAT has been purified to completion, spinach leaves have at least two systems which reside in different subcellular compartments (chloroplast inner membrane and the endoplasmic reticulum) and which incorporate different fatty acids into the glycerol backbone (Frentzen et al. (1984) in *Structure, function and metabolism of plant lipids*; Siegenthaler and Eichenberger, eds. pp 105-110). Isolation of LPAAT genes from *Limnanthes douglasii* is dependent on the approach used to isolate the clone. Two different clones have been isolated which varied in their expression patterns, in their ability to complement an *E. coli* temperature-sensitive mutant defective in LPAAT activity and in their ability to hybridize to the already known maize LPAAT (Brown et al. (1995) *Plant Mol. Biol.* 29:267-278). Thus, the presence of many other LPAATs with different specificities, subcellular locations and activities is expected.

Production of industrially-significant oils in seed oil plants has been a quest of the agricultural industry of some time now. Introduction of the yeast LPAAT sequence into *Arabidopsis* and *B. napus* results in increased seed oil content in many transgenic plants and in changes in seed oil composition (Zou et al. (1997) *Plant Cell* 9:909-923).

SUMMARY OF THE INVENTION

The invention concerns an isolated polynucleotide comprising a nucleotide sequence selected from the group consisting of: (a) a first nucleotide sequence encoding a polypeptide of at least 100 amino acids having at least 80% identity based on the Clustal method of alignment when compared to a polypeptide selected from the group consisting of SEQ ID NOs:2, 4, 6, 8, 10, 12, 14, 16, 18, 26, 28, 30, 32, 34, 36, 38, 40, 42, 44, 46, 48, 50, and 52, or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs: 1, 3, 5, 7, 9, 11, 13, 15, 17, 25, 27, 29, 31, 33, 35, 37, 39, 41, 43, 45, 47, 49, and 51, that codes for the polypeptide selected from the group consisting of SEQ ID NOs:2, 4, 6, 8, 10, 12, 14, 16, 18, 26, 28, 30, 32, 34, 36, 38, 40, 42, 44, 46, 48, 50, and 52.

In a third embodiment, this invention concerns a chimeric gene comprising an isolated polynucleotide of the present invention operably linked to suitable regulatory sequences.

In a fourth embodiment, this invention concerns an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a fifth embodiment, the present invention concerns a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a sixth embodiment, the invention also relates to lysophosphatidic acid acyltransferase (LPAAT isozymes) polypeptides of at least 100 amino acids comprising at least 80% homology based on the Clustal method of alignment compared to a polypeptide selected from the group consisting of SEQ ID NOs:2, 4, 6, 8, 10, 12, 14, 16, 18, 26, 28, 30, 32, 34, 36, 38, 40, 42, 44, 46, 48, 50, and 52.

In a seventh embodiment, the invention concerns a method of selecting an isolated polynucleotide that affects the level of expression of an LPAAT isozyme polypeptide in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level the LPAAT isozyme polypeptide in the host cell containing the isolated polynucleotide; and (d) comparing the level of the LPAAT isozyme polypeptide in the host cell containing the isolated polynucleotide with the level of the LPAAT isozyme polypeptide in the host cell that does not contain the isolated polynucleotide.

In an eighth embodiment, the invention concerns a method of obtaining a nucleic acid fragment encoding a substantial portion of an LPAAT isozyme polypeptide, preferably a plant LPAAT isozyme polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs: 1, 3, 5, 7, 9, 11, 13, 15, 17, 25, 27, 29, 31, 33, 35, 37, 39, 41, 43, 45, 47, 49, and 51 and the complement of such nucleotide sequences; and amplifying a nucleic acid fragment (preferably a cDNA inserted in a cloning vector) using the oligonucleotide primer. The amplified nucleic acid fragment preferably will encode a portion of an LPAAT isozyme amino acid sequence.

In a ninth embodiment, the invention concerns a method of obtaining a nucleic acid fragment encoding all or a substantial portion of the amino acid sequence encoding an LPAAT isozyme polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a tenth embodiment, this invention concerns a composition, such as a hybridization mixture, comprising an isolated polynucleotide of the present invention.

In an eleventh embodiment, this invention concerns an isolated polynucleotide of the present invention comprising at least 30 contiguous nucleotides derived from a nucleic acid sequence selected from the group consisting of SEQ ID NOs: 1, 3, 5, 7, 9, 11, 13, 15, 17, 25, 27, 29, 31, 33, 35, 37, 39, 41, 43, 45, 47, 49, and 51.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably plant cell, such as a monocot or a dicot, under conditions which allow expression of the LPAAT isozyme polynucleotide in an amount sufficient to complement a null mutant to provide a positive selection means.

In a thirteenth embodiment, this invention concerns an isolated polynucleotide comprising a nucleotide sequence selected from the group consisting of: (a) first nucleotide sequence encoding a polypeptide of at least 100 amino acids having at least 95% identity based on the Clustal method of alignment when compared to a polypeptide selected from the group consisting of SEQ ID NOs:20, 22, 24, 54, 56, and 58 or (b) a second nucleotide sequence comprising the complement of the first nucleotide sequence. All of the embodiments described above are applicable with the exception of the particular sequences involved and the sequence identity being at least 95% as noted in the appropriate claims.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825.

TABLE 1

Lysophosphatidic Acid Acyltransferases

| Protein | Clone Designation | SEQ ID NO: (Nucleotide) | SEQ ID NO: (Amino Acid) |
|---|---|---|---|
| Corn Polypeptide Similar to *Mus musculus* LPAAT | Contig of: p0018.chssd06r p0104.cabbd29r cca.pk0027.c9 p0018.chstw94r p0094.csssl20r | 1 | 2 |
| Soybean Polypeptide Similar to *Mus musculus* LPAAT | sl2.pk121.a19 | 3 | 4 |
| Wheat Polypeptide Similar to *Mus musculus* LPAAT | Contig of: wlm1.pk0018.g6 wre1n.pk0040.h11 wre1n.pk0064.g7 | 5 | 6 |
| Corn Polypeptide Similar to *B. pseudomallei* LPAAT | Contig of: ceb5.pk0049.b3 cen3n.pk0027.f6 | 7 | 8 |
| Soybean Polypeptide Similar to *B. pseudomallei* LPAAT | sgs1c.pk001.i16 | 9 | 10 |
| Wheat Polypeptide Similar to *B. pseudomallei* LPAAT | wre1n.pk0027.d4 | 11 | 12 |
| *Arabidopsis* Polypeptide Similar to *Arabidopsis thaliana* Protein | ads1c.pk005.i10 | 13 | 14 |
| Rice Polypeptide Similar to *Arabidopsis thaliana* Protein | Contig of: rls6.pk0076.d5 rlr24.pk0068.e3 | 15 | 16 |
| Soybean Polypeptide Similar to *Arabidopsis thaliana* Protein | scb1c.pk003.d18 | 17 | 18 |
| Rice Polypeptide Similar to Corn LPAAT | Contig of: rr1.pk0004.a10 rr1.pk0039.e10 | 19 | 20 |
| Soybean Polypeptide Similar to Corn LPAAT | Contig of: se4.cp0008.b2 sl2.pk0033.c1 | 21 | 22 |
| Wheat Polypeptide Similar to Corn LPAAT | Contig of: wlk1.pk0004.e7 wle1n.pk0002.g3 | 23 | 24 |
| Catalpa Polypeptide Similar to *Mus musculus* LPAAT | ncs.pk0013.d2:fis | 25 | 26 |
| Corn Polypeptide Similar to | Contig of: | 27 | 28 |

TABLE 1-continued

Lysophosphatidic Acid Acyltransferases

| | | SEQ ID NO: | |
|---|---|---|---|
| Protein | Clone Designation | (Nucleotide) | (Amino Acid) |
| *Mus musculus* LPAAT | ceb1.pk0011.d11 | | |
| | ceb5.pk0053.e3 | | |
| | p0010.cbpbq45r | | |
| | p0018.chssd06r:fis | | |
| Rice Polypeptide Similar to *Mus musculus* LPAAT | rlr2.pk0028.d6:fis | 29 | 30 |
| Sorghum Polypeptide Similar to *Mus musculus* LPAAT | gds1c.pk002.a19:fis | 31 | 32 |
| Soybean Polypeptide Similar to *Mus musculus* LPAAT | sl2.pk121.a19:fis | 33 | 34 |
| Catalpa Polypeptide Similar to *B. pseudomallei* LPAAT | ncs.pk0009.f12:fis | 35 | 36 |
| Wheat Polypeptide Similar to *B. pseudomallei* LPAAT | wre1n.pk0027.d4:fis | 37 | 38 |
| Corn Polypeptide Similar to *Arabidopsis thaliana* Protein | Contig of: ceb1.mn0001.d12:fis cpe1c.pk006.e1 | 39 | 40 |
| Rice Polypeptide Similar to *A. thaliana* Protein | rls6.pk0076.d5:fis | 41 | 42 |
| Soybean Polypeptide Similar to *Arabidopsis thaliana* Protein | scb1c.pk003.d18:fis | 43 | 44 |
| Corn Polypeptide Similar to *A. thaliana* acyltransferase | cco1n.pk062.p19 | 45 | 46 |
| Rice Polypeptide Similar to *A. thaliana* acyltransferase | rlr6.pk0094.f6:fis | 47 | 48 |
| Soybean Polypeptide Similar to *A. thaliana* acyltransferase | sdp4c.pk006.n11:fis | 49 | 50 |
| Soybean Polypeptide Similar to *A. thaliana* acyltransferase | Contig of: sgs1c.pk005.k7 sgs5c.pk0003.e7 | 51 | 52 |
| Rice Polypeptide Similar to Corn LPAAT | rr1.pk0004.a10:fis | 53 | 54 |
| Soybean Polypeptide Similar to Corn LPAAT | sl2.pk0033.c1:fis | 55 | 56 |
| Wheat Polypeptide Similar to Corn LPAAT | wlk1.pk0004.e7:fis | 57 | 58 |

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide" and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from a nucleotide sequence selected from the group consisting of (a) SEQ ID NOs:1, 3, 5, 7, 9, 11, 13, 15, 17, 25, 27, 29, 31, 33, 35, 37, 39, 41, 43, 45, 47, 49, and 51, or the complement of such sequences and /or (b) SEQ ID NOs:19, 21, 23, 53, 55, and 57 or the complement of such sequences. The term "isolated" polynucleotide is one that has been substantially separated or purified away from other nucleic acid sequences in the cell of the organism in which the nucleic acid naturally occurs, i.e., other chromosomal and extrachromosomal DNA and RNA, by conventional nucleic acid purification methods. The term also embraces recombinant polynucleotides and chemically synthesized polynucleotides.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic acid fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of (a) SEQ ID NOs:1, 3, 5, 7, 9, 11, 13, 15, 17, 25, 27, 29, 31, 33, 35, 37, 39, 41, 43, 45, 47, 49, and 51 and the complement of such nucleotide sequences, and/or (b) SEQ ID NOs:19, 21, 23, 53, 55, and 57 and the complement of such nucleotide sequences may be used in methods of selecting an isolated polynucleotide that affects the expression of an LPAAT isozyme polypeptide in a host cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403-410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a DNA that is complementary to and derived from a mRNA template using the enzyme reverse transcriptase. The cDNA can be single-stranded or converted into the double stranded form using, for example, the klenow fragment of DNA polymerase I. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in a sense or antisense orientation.

The term "recombinant" means, for example, that a recombinant nucleic acid sequence is made by an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" or "altered expression" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is a technique for the synthesis of large quantities of specific DNA segments. It consists of a series of repetitive cycles (Perkin Elmer Cetus Instruments, Norwark, Conn.). Typically, the double-stranded DNA is heat denatured, the two primers complementary to the 3' boundaries of the target segment are annealed at low temperature and then extended at an intermediate temperature. One set of these three consecutive steps is referred to as a cycle.

The present invention concerns an isolated polynucleotide comprising a nucleotide sequence selected from the group consisting of: (a) first nucleotide sequence encoding a polypeptide of at least 100 amino acids having at least 80% identity based on the Clustal method of alignment when compared to a polypeptide selected from the group consisting of SEQ ID NOs:2, 4, 6, 8, 10, 12, 14, 16, 18, 26, 28, 30, 32, 34, 36, 38, 40, 42, 44, 46, 48, 50, and 52, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9, 11, 13, 15, 17, 25, 27, 29, 31, 33, 35, 37, 39, 41, 43, 45, 47, 49, and 51, that codes for the polypeptide selected from the group consisting of SEQ ID NOs:2, 4, 6, 8, 10, 12, 14, 16, 18, 26, 28, 30, 32, 34, 36, 38, 40, 42, 44, 46, 48, 50, and 52.

The present invention also concerns an isolated polynucleotide comprising a nucleotide sequence selected from the group consisting of: (a) first nucleotide sequence encoding a polypeptide of at least 100 amino acids having at least 95% identity based on the Clustal method of alignment when compared to a polypeptide selected from the group consisting of SEQ ID NOs:20, 22, 24, 54, 56, and 58 or (b) a second nucleotide sequence comprising the complement of the first nucleotide sequence.

Preferably, the first nucleotide sequence comprises a nucleic acid sequence selected from the group consisting of SEQ ID Nos:19, 21, 23, 53, 55 and 57 that codes for the polypeptide selected from the group consisting of SEQ ID NOs:20, 22, 24, 54, 56, and 58.

Nucleic acid fragments encoding at least a portion of several LPAAT isozymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other LPAAT isozymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673-5677; Loh et al. (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of:

(a) SEQ ID NOs:1, 3, 5, 7, 9, 11, 13, 15, 17, 25, 27, 29, 31, 33, 35, 37, 39, 41, 43, 45, 47, 49, and 51 and the complement of such nucleotide sequences may be used in such methods to obtain a nucleic acid fragment encoding a substantial portion of an amino acid sequence of a polypeptide, and/or (b) SEQ ID NOs:19, 21, 23, 53, 55 and 57 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of an LPAAT isozyme polypeptide preferably a substantial portion of a plant LPAAT isozyme polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of:

(a) SEQ ID NOs:1, 3, 5, 7, 9, 11, 13, 15, 17, 25, 27, 29, 31, 33, 35, 37, 39, 41, 43, 45, 47, 49, and 51 and the complement of such nucleotide sequences; and/or (b) SEQ ID NOs:19, 21, 23, 53, 55 and 57 and the complement of such nucleotide sequences, and amplifying a nucleic acid fragment (preferably a cDNA inserted in a cloning vector) using the oligonucleotide primer. The amplified nucleic acid fragment preferably will encode a portion of an LPAAT isozyme polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns host cells comprising either the chimeric genes of the invention as described herein or an isolated polynucleotide of the invention as described herein. Examples of host cells which can be used to practice the invention include, but are not limited to, yeast, bacteria, plants, and viruses.

As was noted above, the nucleic acid polynucleotides of the instant invention may be used to create transgenic plants in which the disclosed polypeptides are present at higher or lower levels than normal or in cell types or developmental stages in which they are not normally found. This would have the effect of altering the level of specific triacylglycerols in those cells. For example overexpression of an LPAAT similar to the maize LPAAT, such as those contained in Example 6, will result in higher oil content in the seed, stem and leaf while overexpression of LPAAT similar to *Burkholderia pseudomallei* will result in larger accumulation of oil in seed.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an polypeptide of at least 100 amino acids that has at least 80% identity based on the Clustal method of alignment when compared to a polypeptide selected from the group consisting of SEQ ID NOs:2, 4, 6, 8, 10, 12, 14, 16, 18, 26, 28, 30, 32, 34, 36, 38, 40, 42, 44, 46, 48, 50, and 52.

In still another embodiment, the present invention also concerns a polypeptide of at least 100 amino acids that has at least 95% identity based on the Clustal method of alignment when compared to a polypeptide selected from the group consisting of SEQ ID NOs:20, 22, 24, 54, 56, and 58.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded LPAAT isozyme. An example of a vector for high level expression of the instant polypeptides in a bacterial host is provided (Example 9).

All or a substantial portion of the polynucleotides of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

Example 1

Composition of cDNA Libraries, Isolation and Sequencing of cDNA Clones cDNA libraries representing mRNAs from various *Arabidopsis*, catalpa, corn, rice, sorghum, soybean, and wheat tissues were prepared. The characteristics of the libraries are described below.

TABLE 2 cDNA Libraries from *Arabidopsis*, *Catalpa*, Corn, Rice, *Sorghum*, Soybean, and Wheat

| Library | Tissue | Clone |
|---|---|---|
| ads1c | *Arabidopsis Wassilewskija* 6 day old seedlings | ads1c.pk005.i10 |
| cca | Corn Callus Type II Tissue, Undifferentiated, Highly Transformable | cca.pk0027.c9 |
| cco1n | Corn Cob of 67 Day Old Plants Grown in Green House[1] | cco1n.pk062.p19:fis |

TABLE 2-continued cDNA Libraries from *Arabidopsis*, *Catalpa*, Corn, Rice, *Sorghum*, Soybean, and Wheat

| Library | Tissue | Clone |
|---|---|---|
| ceb1 | Corn Embryo 10 to 11 Days After Pollination | ceb1.mn0001.d12:fis |
| ceb1 | Corn Embryo 10 to 11 Days After Pollination | ceb1.pk0011.d11 |
| ceb5 | Corn Embryo 30 Days After Pollination | ceb5.pk0049.b3 |
| ceb5 | Corn Embryo 30 Days After Pollination | ceb5.pk0053.e3 |
| cen3n | Corn Endosperm 20 Days After Pollination[1] | cen3n.pk0027.f6 |
| cpe1c | Corn pooled BMS treated with chemicals related to phosphatase[2] | cpe1c.pk006.e1 |
| gds1c | *Sorghum* Seed 20 Days After Pollination | gds1c.pk002.a19:fis |
| ncs | *Catalpa speciosa* Developing Seed | ncs.pk0009.f12:fis |
| ncs | *Catalpa speciosa* Developing Seed | ncs.pk0013.d2:fis |
| p0010 | Corn Log Phase Suspension Cells Treated With A23187[3] to Induce Mass Apoptosis | p0010.cbpbq45r |
| p0018 | Corn Seedling After 10 Day Drought, Heat Shocked for 24 Hours, Harvested After Recovery at Normal Growth Conditions for 8 Hours | p0018.chssd06r |
| p0018 | Corn Seedling After 10 Day Drought, Heat Shocked for 24 Hours, Harvested After Recovery at Normal Growth Conditions for 8 Hours | p0018.chstw94r |
| p0094 | Corn Leaf Collars for the Ear Leaf (EL) and the Next Leaf Above and Below the EL[1] | p0094.csssl20r |
| p0104 | Corn Roots V5 Stage[4], Corn Root Worm Infested[1] | p0104.cabbd29r |
| rlr2 | Rice Leaf 15 Days After Germination, 2 Hours After Infection of Strain *Magaporthe grisea* 4360-R-62 (AVR2-YAMO); Resistant | rlr2.pk0028.d6:fis |
| rlr24 | Rice Leaf 15 Days After Germination, 24 Hours After Infection of Strain *Magaporthe grisea* 4360-R-62 (AVR2-YAMO); Resistant | rlr24.pk0068.e3 |
| rlr6 | Rice Leaf 15 Days After Germination, 6 Hours After Infection of Strain *Magaporthe grisea* 4360-R-62 (AVR2-YAMO); Resistant | rlr6.pk0094.f6:fis |
| rls6 | Rice Leaf 15 Days After Germination, 6 Hours After Infection of Strain *Magaporthe grisea* 4360-R-67 (AVR2-YAMO); Susceptible | rls6.pk0076.d5 |
| rr1 | Rice Root of Two Week Old Developing Seedling | rr1.pk0004.a10 |
| rr1 | Rice Root of Two Week Old Developing Seedling | rr1.pk0039.e10 |
| scb1c | Soybean Embryogenic Suspension Culture Subjected to 4 Bombardments and Collected 12 Hours Later | scb1c.pk003.d18 |
| sdp4c | Soybean Developing Pods (10-12 mm) | sdp4c.pk006.n11:fis |
| se4 | Soybean Embryo, 19 Days After Flowering | se4.cp0008.b2 |
| sgs1c | Soybean Seeds 4 Hours After Germination | sgs1c.pk001.i16 |
| sgs1c | Soybean Seeds 4 Hours After Germination | sgs1c.pk005.k7 |
| sgs5c | Soybean Seeds 4 Days After Germination | sgs5c.pk0003.e7 |
| sl2 | Soybean Two-Week-Old Developing Seedlings Treated With 2.5 ppm chlorimuron | sl2.pk0033.c1 |
| sl2 | Soybean Two-Week-Old Developing Seedlings Treated With 2.5 ppm chlorimuron | sl2.pk121.a19 |
| wle1n | Wheat Leaf From 7 Day Old Etiolated Seedling[1] | wle1n.pk0002.g3 |
| wlk1 | Wheat Seedlings 1 Hour After Treatment With Herbicide[5] | wlk1.pk0004.e7 |
| wlm1 | Wheat Seedlings 1 Hour After Inoculation With *Erysiphe graminis f.* sp *tritici* | wlm1.pk0018.g6 |
| wre1n | Wheat Root From 7 Day Old Etiolated Seedling[1] | wre1n.pk0027.d4 |
| wre1n | Wheat Root From 7 Day Old Etiolated Seedling[1] | wre1n.pk0040.h11 |
| wre1n | Wheat Root From 7 Day Old Etiolated Seedling[1] | wre1n.pk0064.g7 |

[1] These libraries were normalized essentially as described in U.S. Pat. No. 5,482,845, the disclosure of which is hereby incorporated by reference.
[2] Chemicals used included okadaic acid, cyclosporin A, calyculin A, cypermethrin.
[3] A23187 is commercially available from several vendors including Calbiochem.
[4] Corn developmental stages are explained in the publication "How a corn plant develops" from the Iowa State University Coop. Ext. Service Special Report No. 48 reprinted June 1993.
[5] Application of 6-iodo-2-propoxy-3-propyl-4(3H)-quinazolinone; synthesis and methods of using this compound are described in USSN 08/545,827, the disclosure of which is hereby incorporated by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

Example 2

Identification of cDNA Clones cDNA clones encoding LPAAT isozymes were identified by conducting BLAST (Basic Local Alignment Search Tool; Altschul et al. (1993) *J. Mol. Biol.* 215:403-410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Proteins Similar to *Mus musculus* LPAAT The BLASTX search using the EST sequences from clones listed in Table 3 revealed similarity of the proteins encoded by the cDNAs to an unknown protein from *Caenorhabditis elegans* and a putative LPAAT protein from *Mus musculus* (NCBI General Identifier Nos. 3878960 and 2317725, respectively). Shown in Table 3 are the BLAST results for individual ESTs ("EST") or for the sequences of contigs assembled from two or more ESTs ("Contig"):

TABLE 3

BLAST Results for Sequences Encoding Polypeptides Homologous to *Mus musculus* LPAAT

| Clone | Status | BLAST pLog Score | |
|---|---|---|---|
| | | 3878960 | 2317725 |
| Contig of: p0018.chssd06r p0104.cabbd29r cca.pk0027.c9 p0018.chstw94r p0094.csssl20r | Contig | 59.40 | 57.70 |
| sl2.pk121.a19 | EST | 15.22 | 10.09 |

TABLE 3-continued

BLAST Results for Sequences Encoding Polypeptides Homologous to *Mus musculus* LPAAT

| Clone | Status | BLAST pLog Score | |
|---|---|---|---|
| | | 3878960 | 2317725 |
| Contig of: wlm1.pk0018.g6 wre1n.pk0040.h11 wre1n.pk0064.g7 | Contig | 54.30 | 50.52 |

The sequence of the entire cDNA insert in clones p0018.chssd06r and s12.pk121.a19 was determined. Further sequencing and analysis of the DuPont proprietary EST database allowed the identification of catalpa, rice, and sorghum clones encoding polypeptides with similarities to *Mus musculus* LPAAT. The BLAST search using the sequences from clones listed in Table 4 revealed similarity of the proteins encoded by the cDNAs to an unknown protein from *Caenorhabditis elegans* and a putative LPAAT protein from *Mus musculus* (NCBI General Identifier Nos. 3878960 and 2317725, respectively). Shown in Table 4 are the BLAST results for the sequences of the entire cDNA inserts comprising the indicated cDNA clones ("FIS"), the sequences of the entire protein encoded by a contig assembled from an FIS and one or more ESTs ("Contig*"), or the sequences of the entire protein encoded by an FIS ("CGS"):

TABLE 4

BLAST Results for Sequences Encoding Polypeptides Homologous to *Mus musculus* LPAAT

| Clone | Status | BLAST pLog Score | |
|---|---|---|---|
| | | 3878960 | 2317725 |
| ncs.pk0013.d2:fis | CGS | 56.40 | 54.15 |
| Contig of: ceb1.pk0011.d11 ceb5.pk0053.e3 p0010.cbpbq45r p0018.chssd06r:fis | Contig* | 58.00 | 55.04 |
| rlr2.pk0028.d6:fis | CGS | 57.70 | 55.40 |
| gds1c.pk002.a19:fis | FIS | 58.10 | 45.52 |
| sl2.pk121.a19:fis | CGS | 57.70 | 53.00 |

In this type of plant LPAAT domain I consists of amino acids Asn-His-Thr-Ser-Met-Ile-Asp-Phe-Ile and domain II (62 amino acids downstream) consists of amino acids Leu-Ile-Phe-Pro-Glu-Gly-Thr-Cys.

The data in Table 5 represents a calculation of the percent identity of the amino acid sequences set forth in SEQ ID NOs:2, 4 6, 26, 28, 30, 32, and 34 and the *Caenorhabditis elegans* and *Mus musculus* sequences (NCBI General Identifier Nos. 3878960 and 2317725, respectively).

TABLE 5

Percent Identity of Amino Acid Sequences Deduced From the Nucleotide Sequences of cDNA Clones Encoding Polypeptides Homologous to *Mus musculus* LPAAT

| SEQ ID NO. | Percent Identity to | |
|---|---|---|
| | 3878960 | 2317725 |
| 2 | 38.5 | 35.1 |
| 4 | 39.3 | 29.9 |

TABLE 5-continued

Percent Identity of Amino Acid Sequences Deduced From the
Nucleotide Sequences of cDNA Clones Encoding Polypeptides
Homologous to *Mus musculus* LPAAT

| | Percent Identity to | |
|---|---|---|
| SEQ ID NO. | 3878960 | 2317725 |
| 6 | 39.8 | 35.9 |
| 26 | 31.8 | 35.4 |
| 28 | 32.1 | 36.1 |
| 30 | 31.9 | 37.4 |
| 32 | 33.5 | 36.1 |
| 34 | 32.2 | 35.4 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn, a sorghum, a soybean and a wheat LPAAT and entire catalpa, corn, rice, and soybean LPAAT proteins. These sequences represent the first catalpa, corn, rice, soybean, and wheat sequences encoding LPAAT proteins of this type.

Example 4

Characterization of cDNA Clones Encoding LPAATs Similar to *Burkholderia pseudomallei* LPAAT The BLASTX search using the EST sequences from clones listed in Table 3 revealed similarity of the polypeptides encoded by the cDNAs to LPAAT from *Burkholderia pseudomallei* (NCBI General Identifier No. 3135672). Shown in Table 6 are the BLAST results for individual ESTs ("EST") the sequences of the entire cDNA inserts comprising the indicated cDNA clones ("FIS"), or for the sequences of contigs assembled from two or more ESTs ("Contig"):

TABLE 6

BLAST Results for Sequences Encoding Polypeptides Homologous
to *Burkholderia pseudomallei* LPAAT

| Clone | Status | BLAST pLog Score 3135672 |
|---|---|---|
| Contig of:<br>ceb5.pk0049.b3<br>cen3n.pk0027.f6 | Contig | 9.52 |
| sgs1c.pk001.i16 | FIS | 9.30 |
| wre1n.pk0027.d4 | EST | 4.00 |

The sequence of the entire cDNA insert from clone wre1n.pk0027.d4 was determined. Further sequencing and analysis of the DuPont proprietary database allowed the identification of a catalpa clone with similarity to the *Burkholderia pseudomallei* LPAAT. The BLAST search using the sequences from clones listed in Table 7 revealed similarity of the polypeptides encoded by the *Arabidopsis thaliana* contig to similar to acyltransferase (NCBI General Identifier No. 6503307) and of the cDNAs to LPAAT from *Burkholderia pseudomallei* (NCBI General Identifier No. 3135672). Shown in Table 7 are the BLAST results for the sequences of the entire cDNA inserts comprising the indicated cDNA clones encoding the entire protein ("CGS"):

TABLE 7

BLAST Results for Sequences Encoding Polypeptides Homologous
to *Burkholderia pseudomallei* LPAAT

| | | BLAST pLog Score | |
|---|---|---|---|
| Clone | Status | 6503307 | 3135672 |
| ncs.pk0009.f12:fis | CGS | 87.00 | 10.22 |
| wre1n.pk0027.d4:fis | CGS | 83.52 | 11.40 |

In this type of plant LPAAT domain I consists of amino acids Asn-His-(Val or Ile)-Ser-Tyr-(Val, Ile, or Leu)-Asp-Ile-Leu and domain II (62 amino acids downstream) consists of amino acids Xaa1-(Leu or Ile)-Phe-Pro-Glu-Gly-Thr-Thr, where Xaa1 is Leu, Ile, Met or Tyr.

The data in Table 8 represents a calculation of the percent identity of the amino acid sequences set forth in SEQ ID NOs:8, 10, 12, 36, and 38 and the *Burkholderia pseudomallei* sequence (NCBI General Identifier No. 3135672).

TABLE 8

Percent Identity of Amino Acid Sequences Deduced From the
Nucleotide Sequences of cDNA Clones Encoding Polypeptides
Homologous to *Burkholderia pseudomallei* LPAAT

| SEQ ID NO. | Percent Identity to 3135672 |
|---|---|
| 8 | 19.8 |
| 10 | 17.6 |
| 12 | 17.4 |
| 36 | 219.1 |
| 38 | 20.3 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a wheat LPAAT and entire corn, catalpa, soybean, and wheat LPAAT proteins. These sequences represent the first corn, catalpa, soybean, and wheat sequences encoding LPAATs of this type.

Example 5

Characterization of cDNA Clones Encoding Putative LPAATs

The BLASTX search using the EST sequences from clones listed in Table 9 revealed similarity of the polypeptides encoded by the contig to an unknown protein from *Arabidopsis thaliana* (NCBI General Identifier No. 2979560). Shown in Table 9 are the BLAST results for individual ESTs ("EST"), the sequences of the entire cDNA inserts comprising the indicated cDNA clones ("FIS"), or the sequences of contigs assembled from two or more ESTs ("Contig"):

TABLE 9

BLAST Results for Sequences Encoding Polypeptides Homologous to LPAATs

| Clone | Status | BLAST pLog Score 2979560 |
|---|---|---|
| ads1c.pk005.i10 | FIS | 52.00 |
| Contig of: rls6.pk0076.d5 rlr24.pk0068.e3 | Contig | 22.70 |
| scb1c.pk003.d18 | EST | 45.04 |

The sequence of the entire cDNA insert in clones rls6.pk0076.d5 and scb1c.pk003.d18 was determined. Further sequencing and analysis of the DuPont proprietary database allowed the identification of corn clones with similarities to the *Arabidopsis thaliana* putative protein. The BLAST search using the sequences from clones listed in Table 10 revealed similarity of the polypeptides encoded by the contig to an unknown protein from *Arabidopsis thaliana* (NCBI General Identifier No. 2979560). Shown in Table 10 are the BLAST results for the sequences of the entire cDNA inserts comprising the indicated cDNA clones ("FIS"), the sequences of contigs assembled from two or more ESTs ("Contig"), or the sequences of an FIS encoding the entire protein ("CGS"):

TABLE 10

BLAST Results for Sequences Encoding Polypeptides Homologous to LPAATs

| Clone | Status | BLAST pLog Score 2979560 |
|---|---|---|
| Contig of: ceb1.mn0001.d12:fis cpe1c.pk006.e1 | Contig | 21.70 |
| rls6.pk0076.d5:fis | FIS | 67.52 |
| scb1c.pk003.d18:fis | CGS | 81.00 |

In this type of plant LPAATs domain I includes the amino acids Ser-Asn-His-(Val or Ile)Ser-Tyr-Ile-Glu-Pro-Ile and domain II (61 amino acids downstream) includes the amino acids Leu-Leu-Phe-Pro-Glu-Gly-Thr-Thr-Thr.

The BLAST search using the sequences from clones listed in Table 11 revealed similarity of the polypeptides encoded by the contig to a member of the acyltransferase family from *Arabidopsis thaliana* (NCBI General Identifier No. 6503307). Shown in Table 11 are the BLAST results for the sequences of the entire cDNA inserts comprising the indicated cDNA clones ("FIS"), the sequences of contigs assembled from two or more ESTs ("Contig"), or the sequences of the entire protein encoded by an FIS ("CGS"):

TABLE 11

BLAST Results for Sequences Encoding Polypeptides Homologous to LPAATs

| Clone | Status | BLAST pLog Score 6503307 |
|---|---|---|
| cco1n.pk062.p19:fis | CGS | 119.00 |
| rlr6.pk0094.f6:fis | CGS | 111.00 |
| sdp4c.pk006.n11:fis | FIS | 95.52 |

TABLE 11-continued

BLAST Results for Sequences Encoding Polypeptides Homologous to LPAATs

| Clone | Status | BLAST pLog Score 6503307 |
|---|---|---|
| Contig of: sgs1c.pk005.k7 sgs5c.pk0003.e7 | Contig | 6.52 |

In this type of plant LPAATs domain I includes the amino acids Ser-Asn-His-Val-Ser-Tyr-(Val or Leu)-Asp-Ile-Leu and domain II (61 amino acids downstream) includes the amino acids Leu-Phe-Pro-Glu-Gly-Thr-Thr-Thr.

The data in Table 12 represents a calculation of the percent identity of the amino acid sequences set forth in SEQ ID NOs:14, 16, 18, 40, 42, 44, 46, 48, 50, and 52 and the *Arabidopsis thaliana* sequences (NCBI General Identifier No. 6503307).

TABLE 12

Percent Identity of Amino Acid Sequences Deduced From the Nucleotide Sequences of cDNA Clones Encoding Polypeptides Homologous to LPAATs

| | Percent Identity to | |
|---|---|---|
| SEQ ID NO. | 2979560 | 6503307 |
| 14 | 36.3 | 13.2 |
| 16 | 32.8 | 13.8 |
| 18 | 65.4 | 16.8 |
| 40 | 27.0 | 21.1 |
| 42 | 50.2 | 16.9 |
| 44 | 65.4 | 19.7 |
| 46 | 18.0 | 54.6 |
| 48 | 18.1 | 52.5 |
| 50 | 11.2 | 63.7 |
| 52 | 12.4 | 19.5 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an *Arabidopsis*, a corn, a rice, and a soybean LPAAT and an entire soybean LPAAT. These sequences represent the first corn, rice, soybean, and *Arabidopsis* sequences encoding LPAAT of this type.

Example 6

Characterization of cDNA Clones Encoding Proteins Similar to *Zea mays* LPAAT

The BLASTX search using the EST sequences from clones listed in Table 13 revealed similarity of the polypeptides encoded by the cDNAs to LPAAT from *Zea mays* (NCBI General Identifier No. 575960). Shown in Table 13 are the BLAST results for the sequences of contigs assembled from two or more ESTs ("Contig"):

TABLE 13

BLAST Results for Sequences Encoding Polypeptides Homologous to *Zea mays* LPAAT

| Clone | Status | BLAST pLog Score 575960 |
|---|---|---|
| Contig of: rr1.pk0004.a10 rr1.pk0039.e10 | Contig | 57.70 |
| Contig of: se4.cp0008.b2 sl2.pk0033.c1 | Contig | 67.15 |
| Contig of: wlk1.pk0004.e7 wle1n.pk0002.g3 | Contig | 78.70 |

The sequence of the entire cDNA insert in clones rr1.pk0004.a10, s12.pk0033.c1, and w1k1.pk0004.e7 was determined. The BLASTP search using the amino acid sequences from clones listed in Table 14 revealed similarity of the polypeptides encoded by the cDNAs to LPAATs from *Zea mays* and *Brassica napus* (NCBI General Identifier Nos. 1076821 and 4583544, respectively). Shown in Table 14 are the BLAST results for the sequences of the entire cDNA inserts comprising the indicated cDNA clones encoding the entire protein ("CGS"):

TABLE 14

BLAST Results for Sequences Encoding Polypeptides Homologous to *Zea mays* LPAAT

| | | BLAST pLog Score | |
|---|---|---|---|
| Clone | Status | 1076821 | 4583544 |
| rr1.pk0004.a10:fis | CGS | >254.00 | 149.00 |
| sl2.pk0033.c1:fis | CGS | 169.00 | 175.00 |
| wlk1.pk0004.e7:fis | CGS | >254.00 | 148.00 |

In this type of plant LPAAT domain I consists of amino acids Ser-Asn-His-Arg-Ser-Asp-Ile-Asp-Trp-Leu and domain II (69 amino acids downstream) consists of amino acids Ala-Leu-Phe-Val-Glu-Gly-Thr-Arg-Phe.

The data in Table 15 represents a calculation of the percent identity of the amino acid sequences set forth in SEQ ID NOs:20, 22, 24, 54, 56, and 58 and the *Zea mays* sequence (NCBI General Identifier Nos. 1076821).

TABLE 15

Percent Identity of Amino Acid Sequences Deduced From the Nucleotide Sequences of cDNA Clones Encoding Polypeptides Homologous to *Zea mays* LPAAT

| SEQ ID NO. | Percent Identity to 1076821 |
|---|---|
| 20 | 72.6 |
| 22 | 72.4 |
| 24 | 73.1 |
| 54 | 91.2 |
| 56 | 70.1 |
| 58 | 84.8 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of and an entire rice, soybean, and wheat LPAAT. These sequences represent the first rice, soybean, and wheat sequences encoding LPAATs of this type.

Example 7

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL 1-Blue (Epicurian *Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature (London)* 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Activity assays may be conducted under well known experimental conditions which permit optimal enzymatic activity. For example, assays for LPAAT which incorporates medium-sized chain fatty acids are presented by Knutzon et al. (1995) Plant Physiol. 109:999-1006. Assays for LPAAT which incorporates fatty acids longer than 18 carbons are presented by Lassner et al. (1995) Plant Physiol. 109:1389-1394. Assays to investigate the fatty acid selectivity of LPAATs is presented by Löhden and Frentzen (1992) Planta 188:215-224.

What is claimed is:

1. An isolated polynucleotide comprising:
   (a) a nucleotide sequence encoding a polypeptide having lysophosphatidic acid acyltransferase (LPAAT) activity, wherein the polypeptide has an amino acid sequence of at least 95% sequence identity, based on the Clustal V method of alignment, when compared to SEQ ID NO:34; or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide comprises SEQ ID NO:34.

3. The polynucleotide of claim 1 wherein the nucleotide sequence comprises SEQ ID NO:33.

4. A vector comprising the polynucleotide of claim 1.

5. A recombinant DNA construct comprising the polynucleotide of claim 1 operable linked to at least one regulatory sequence.

6. A method for transforming a cell, comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

11. A method for isolating a polypeptide comprising isolating the polypeptide from a cell or culture medium of the cell, wherein the cell comprises a recombinant DNA construct comprising the polynucleotide of claim 1 operable linked to at least one regulatory sequence.

12. A method of altering the level of lysophosphatidic acid acyltransferase expression in a host cell comprising:

(a) transforming a host cell with the recombinant DNA construct of claim 5; and (b) growing the transformed host cell under conditions that are suitable for expression of the recombinant DNA construct wherein expression of the recombinant DNA construct results in production of altered levels of lysophosphatidic acid acyltransferase in the transformed host cell.

\* \* \* \* \*

SEQUENCE LISTING

```
<160> NUMBER OF SEQ ID NOS: 58

<210> SEQ ID NO 1
<211> LENGTH: 928
<212> TYPE: DNA
<213> ORGANISM: Zea mays
<220> FEATURE:
<221> NAME/KEY: unsure
<222> LOCATION: (858)
<223> OTHER INFORMATION: n = a, c, g, or t
<220> FEATURE:
<221> NAME/KEY: unsure
<222> LOCATION: (876)
<223> OTHER INFORMATION: n = a, c, g, or t
<220> FEATURE:
<221> NAME/KEY: unsure
<222> LOCATION: (897)
<223> OTHER INFORMATION: n = a, c, g, or t
```

-continued

<400> SEQUENCE: 1

```
cttttttcct gtccatttcc tattgaaagg gcaagacaag ttgagaagta aaattgagag      60
gaagttggtt gaaatgatgt gcagtgtttt tgttgcttca tggactggag ttatcaagta     120
tcatggacca cgcccaagca cacgacctca tcaggtattc gttgcaaacc atacatcgat     180
gatagatttc attattctgg agcaaatgac agcatttgct gtcatcatgc agaagcatcc     240
tggatgggtt ggatttattc agaagactat cttggaaagt gtcggttgca tctggtttaa     300
tcgtaatgat ctccgggacc gtgaagttac ggcacggaag ttacgtgatc atgttcaaca     360
accagacaac aatcctctgt tgattttccc ggaaggaact tgtgtgaaca ccagtacac      420
ggtcatgttc aagaagggtg cctttgagct tggctgcgct gtatgtccaa tagctatcaa     480
gtacaataaa atatttgttg atgccttttg gaacagtaag aagcaatctt ttacaatgca     540
cttggtccgg ctgatgacat catgggctgt tgtgtgtgat gtttggtact acctcctca      600
atatctgagg gagggagaga cggcaattgc atttgctgag agagtaaggg acatgatagc     660
tgctagagct ggactaaaga agttccttgg gatggctatc tgaaacacaa ccgtcctagt     720
cccaaacaca ctgaagagaa acaacgcata tttgccgaat ctgtcttgat gagactggag     780
gagaaatgaa gggacgtaaa gccgtacaag tgcacttcgt tagggttta  catgcagcta    840
ccttgttatt ccgttggntt cccaaaaaaa aaaaantgag cctgggacac gtcaaantga     900
ccacctccat tttggttggt taattttg                                        928
```

<210> SEQ ID NO 2
<211> LENGTH: 262
<212> TYPE: PRT
<213> ORGANISM: Zea mays

<400> SEQUENCE: 2

```
Phe Phe Pro Val His Phe Leu Leu Lys Gly Gln Asp Lys Leu Arg Ser
  1               5                  10                  15

Lys Ile Glu Arg Lys Leu Val Glu Met Met Cys Ser Val Phe Val Ala
                 20                  25                  30

Ser Trp Thr Gly Val Ile Lys Tyr His Gly Pro Arg Pro Ser Thr Arg
             35                  40                  45

Pro His Gln Val Phe Val Ala Asn His Thr Ser Met Ile Asp Phe Ile
         50                  55                  60

Ile Leu Glu Gln Met Thr Ala Phe Ala Val Ile Met Gln Lys His Pro
 65                  70                  75                  80

Gly Trp Val Gly Phe Ile Gln Lys Thr Ile Leu Glu Ser Val Gly Cys
                 85                  90                  95

Ile Trp Phe Asn Arg Asn Asp Leu Arg Asp Arg Glu Val Thr Ala Arg
            100                 105                 110

Lys Leu Arg Asp His Val Gln Gln Pro Asp Asn Asn Pro Leu Leu Ile
        115                 120                 125

Phe Pro Glu Gly Thr Cys Val Asn Asn Gln Tyr Thr Val Met Phe Lys
    130                 135                 140

Lys Gly Ala Phe Glu Leu Gly Cys Ala Val Cys Pro Ile Ala Ile Lys
145                 150                 155                 160

Tyr Asn Lys Ile Phe Val Asp Ala Phe Trp Asn Ser Lys Lys Gln Ser
                165                 170                 175

Phe Thr Met His Leu Val Arg Leu Met Thr Ser Trp Ala Val Val Cys
            180                 185                 190

Asp Val Trp Tyr Leu Pro Pro Gln Tyr Leu Arg Glu Gly Glu Thr Ala
```

```
              195                 200                 205
Ile Ala Phe Ala Glu Arg Val Arg Asp Met Ile Ala Ala Arg Ala Gly
    210                 215                 220

Leu Lys Lys Val Pro Trp Asp Gly Tyr Leu Lys His Asn Arg Pro Ser
225                 230                 235                 240

Pro Lys His Thr Glu Glu Lys Gln Arg Ile Phe Ala Glu Ser Val Leu
                245                 250                 255

Met Arg Leu Glu Glu Lys
            260

<210> SEQ ID NO 3
<211> LENGTH: 519
<212> TYPE: DNA
<213> ORGANISM: Glycine max
<220> FEATURE:
<221> NAME/KEY: unsure
<222> LOCATION: (46)
<223> OTHER INFORMATION: n = a, c, g, or t
<220> FEATURE:
<221> NAME/KEY: unsure
<222> LOCATION: (69)
<223> OTHER INFORMATION: n = a, c, g, or t
<220> FEATURE:
<221> NAME/KEY: unsure
<222> LOCATION: (72)
<223> OTHER INFORMATION: n = a, c, g, or t
<220> FEATURE:
<221> NAME/KEY: unsure
<222> LOCATION: (86)
<223> OTHER INFORMATION: n = a, c, g, or t
<220> FEATURE:
<221> NAME/KEY: unsure
<222> LOCATION: (117)
<223> OTHER INFORMATION: n = a, c, g, or t
<220> FEATURE:
<221> NAME/KEY: unsure
<222> LOCATION: (142)
<223> OTHER INFORMATION: n = a, c, g, or t
<220> FEATURE:
<221> NAME/KEY: unsure
<222> LOCATION: (144)
<223> OTHER INFORMATION: n = a, c, g, or t
<220> FEATURE:
<221> NAME/KEY: unsure
<222> LOCATION: (186)
<223> OTHER INFORMATION: n = a, c, g, or t
<220> FEATURE:
<221> NAME/KEY: unsure
<222> LOCATION: (241)
<223> OTHER INFORMATION: n = a, c, g, or t
<220> FEATURE:
<221> NAME/KEY: unsure
<222> LOCATION: (245)
<223> OTHER INFORMATION: n = a, c, g, or t
<220> FEATURE:
<221> NAME/KEY: unsure
<222> LOCATION: (347)
<223> OTHER INFORMATION: n = a, c, g, or t
<220> FEATURE:
<221> NAME/KEY: unsure
<222> LOCATION: (368)..(369)
<223> OTHER INFORMATION: n = a, c, g, or t
<220> FEATURE:
<221> NAME/KEY: unsure
<222> LOCATION: (371)
<223> OTHER INFORMATION: n = a, c, g, or t
<220> FEATURE:
<221> NAME/KEY: unsure
<222> LOCATION: (404)
<223> OTHER INFORMATION: n = a, c, g, or t
<220> FEATURE:
<221> NAME/KEY: unsure
<222> LOCATION: (413)
<223> OTHER INFORMATION: n = a, c, g, or t
```

```
<220> FEATURE:
<221> NAME/KEY: unsure
<222> LOCATION: (422)
<223> OTHER INFORMATION: n = a, c, g, or t
<220> FEATURE:
<221> NAME/KEY: unsure
<222> LOCATION: (436)
<223> OTHER INFORMATION: n = a, c, g, or t
<220> FEATURE:
<221> NAME/KEY: unsure
<222> LOCATION: (438)
<223> OTHER INFORMATION: n = a, c, g, or t
<220> FEATURE:
<221> NAME/KEY: unsure
<222> LOCATION: (479)
<223> OTHER INFORMATION: n = a, c, g, or t
<220> FEATURE:
<221> NAME/KEY: unsure
<222> LOCATION: (489)
<223> OTHER INFORMATION: n = a, c, g, or t
<220> FEATURE:
<221> NAME/KEY: unsure
<222> LOCATION: (493)
<223> OTHER INFORMATION: n = a, c, g, or t
<220> FEATURE:
<221> NAME/KEY: unsure
<222> LOCATION: (504)
<223> OTHER INFORMATION: n = a, c, g, or t
<220> FEATURE:
<221> NAME/KEY: unsure
<222> LOCATION: (508)..(509)
<223> OTHER INFORMATION: n = a, c, g, or t
<220> FEATURE:
<221> NAME/KEY: unsure
<222> LOCATION: (516)
<223> OTHER INFORMATION: n = a, c, g, or t

<400> SEQUENCE: 3
gagaactagt ctcgagtttt tttttttttt ttttggtcat ggaatnattt tcaggcaatt      60
tcatgtaana tntacatgta tatcanaata gtaagtggag tacaaacaag ggttggngaa     120
aatcattact gaaaaagtaa ananatatac attattttc ctcaaagcgc cgcaacacag      180
actcancgaa tatttgttgc tttccttctc tgtgcttggg actagggcga gaatacttca     240
natanccatc ccaaggaacc ttttaagcc cagcacgatg tgagattatg tctctaactc      300
tctctgcaaa ttcaatgggt gtctctcctg gcttcaaatt ttgtggntcc aagtaccata     360
catcacannc nacagcccaa gatgtcatta attgcaagag atgnctggtg aangattgct     420
tncgactatt ccaaancngc atcgacgaaa attttaatgt acttgattgc caccggggna     480
aaatttgtnc agncaaagtc aaantggnnc ccttcntgg                            519

<210> SEQ ID NO 4
<211> LENGTH: 107
<212> TYPE: PRT
<213> ORGANISM: Glycine max
<220> FEATURE:
<221> NAME/KEY: UNSURE
<222> LOCATION: (24)
<223> OTHER INFORMATION: Xaa = any amino acid
<220> FEATURE:
<221> NAME/KEY: UNSURE
<222> LOCATION: (36)
<223> OTHER INFORMATION: Xaa = any amino acid
<220> FEATURE:
<221> NAME/KEY: UNSURE
<222> LOCATION: (43)
<223> OTHER INFORMATION: Xaa = any amino acid
<220> FEATURE:
<221> NAME/KEY: UNSURE
<222> LOCATION: (79)
<223> OTHER INFORMATION: Xaa = any amino acid
<220> FEATURE:
```

```
<221> NAME/KEY: UNSURE
<222> LOCATION: (97)
<223> OTHER INFORMATION: Xaa = any amino acid

<400> SEQUENCE: 4

Pro Val Ala Ile Lys Tyr Ile Lys Ile Phe Val Asp Ala Val Trp Asn
 1               5                  10                  15

Ser Arg Lys Gln Ser Phe Thr Xaa His Leu Leu Gln Leu Met Thr Ser
             20                  25                  30

Trp Ala Val Xaa Cys Asp Val Trp Tyr Leu Xaa Pro Gln Asn Leu Lys
         35                  40                  45

Pro Gly Glu Thr Pro Ile Glu Phe Ala Glu Arg Val Arg Asp Ile Ile
     50                  55                  60

Ser His Arg Ala Gly Leu Lys Lys Val Pro Trp Asp Gly Tyr Xaa Lys
 65                  70                  75                  80

Tyr Ser Arg Pro Ser Pro Lys His Arg Glu Gly Lys Gln Gln Ile Phe
                 85                  90                  95

Xaa Glu Ser Val Leu Arg Arg Phe Glu Glu Lys
            100                 105

<210> SEQ ID NO 5
<211> LENGTH: 1067
<212> TYPE: DNA
<213> ORGANISM: Triticum aestivum
<220> FEATURE:
<221> NAME/KEY: unsure
<222> LOCATION: (935)
<223> OTHER INFORMATION: n = a, c, g, or t
<220> FEATURE:
<221> NAME/KEY: unsure
<222> LOCATION: (1009)
<223> OTHER INFORMATION: n = a, c, g, or t
<220> FEATURE:
<221> NAME/KEY: unsure
<222> LOCATION: (1016)..(1017)
<223> OTHER INFORMATION: n = a, c, g, or t
<220> FEATURE:
<221> NAME/KEY: unsure
<222> LOCATION: (1029)
<223> OTHER INFORMATION: n = a, c, g, or t
<220> FEATURE:
<221> NAME/KEY: unsure
<222> LOCATION: (1034)..(1035)
<223> OTHER INFORMATION: n = a, c, g, or t
<220> FEATURE:
<221> NAME/KEY: unsure
<222> LOCATION: (1061)
<223> OTHER INFORMATION: n = a, c, g, or t

<400> SEQUENCE: 5
tgcttcttgg actggagtga tcaagtacca tggaccacgc ccaagctcac gaccttatca      60
ggtatttgtt gcaaaccata catcgatgat agattttatt attctggagc agatgacagc     120
atttgctgtc atcatgcaaa agcatcctgg atgggttgga tttattcaga agactattct     180
ggaaagtgtg gttgcatctg ggtttaaccg taatgatctc aaggatcgtg aagtagttgg     240
aagaaagtta cgtgatcaag ttcagcatcc agacaacaat cctctcttga ttttcccgga     300
aggaacttgt gttaataatc agtacactgt gatgttcaag aagggtgctt ttgagcttgg     360
ctgtgctgta tgtccaatag ctatcaaata taataaaata tttgttgacg ccttctggaa     420
tagtaagaag caatctttta caatgcattt ggttcgtctt atgacatcat gggctgttgt     480
ttgtgatgtt tggtcttggg aacctcagta tctcagggaa ggggagacag cgatagaatt     540
tactgaaaga gtgagggaca tgatagctgc tcgggctggt cttaagaagg ttccatggga     600
```

```
tggctatctg aaacataacc gccctagccc caaacatacc gaggaaaagc agcgcatgtt      660
tgctgaatct gtgttgagga gactagagga aaactaaata gctatcaatc aactcacggt      720
ctcctggtta gttgagggat ttcccttag ttgccttgta atctgttaat cacccaagtg       780
agacctgggg catgtggaaa tgaccaccgc agttttgctg taaatttgtt tgcggtttga      840
cagaatcagt agcatgtgct tggcaagaaa gaactattga atcaaccttg ctatacatac      900
gacactagtc cgattttgt acaccacaga tcaancgttg atccctgaac aaactgcagt       960
gaacacagat ttgcgtgtac acaaattgac atggacatgt ccatagggnt cgcatnnatg     1020
gatcgtgcna agtnnttaat actaaagatg gtaggtaacc naacatt                   1067
```

<210> SEQ ID NO 6
<211> LENGTH: 231
<212> TYPE: PRT
<213> ORGANISM: Triticum aestivum

<400> SEQUENCE: 6

```
Ala Ser Trp Thr Gly Val Ile Lys Tyr His Gly Pro Arg Pro Ser Ser
 1               5                  10                  15

Arg Pro Tyr Gln Val Phe Val Ala Asn His Thr Ser Met Ile Asp Phe
             20                  25                  30

Ile Ile Leu Glu Gln Met Thr Ala Phe Ala Val Ile Met Gln Lys His
         35                  40                  45

Pro Gly Trp Val Gly Phe Ile Gln Lys Thr Ile Leu Glu Ser Val Val
     50                  55                  60

Ala Ser Gly Phe Asn Arg Asn Asp Leu Lys Asp Arg Glu Val Val Gly
 65                  70                  75                  80

Arg Lys Leu Arg Asp Gln Val Gln His Pro Asp Asn Asn Pro Leu Leu
                 85                  90                  95

Ile Phe Pro Glu Gly Thr Cys Val Asn Asn Gln Tyr Thr Val Met Phe
            100                 105                 110

Lys Lys Gly Ala Phe Glu Leu Gly Cys Ala Val Cys Pro Ile Ala Ile
        115                 120                 125

Lys Tyr Asn Lys Ile Phe Val Asp Ala Phe Trp Asn Ser Lys Lys Gln
    130                 135                 140

Ser Phe Thr Met His Leu Val Arg Leu Met Thr Ser Trp Ala Val Val
145                 150                 155                 160

Cys Asp Val Trp Ser Trp Glu Pro Gln Tyr Leu Arg Glu Gly Glu Thr
                165                 170                 175

Ala Ile Glu Phe Thr Glu Arg Val Arg Asp Met Ile Ala Ala Arg Ala
            180                 185                 190

Gly Leu Lys Lys Val Pro Trp Asp Gly Tyr Leu Lys His Asn Arg Pro
        195                 200                 205

Ser Pro Lys His Thr Glu Glu Lys Gln Arg Met Phe Ala Glu Ser Val
    210                 215                 220

Leu Arg Arg Leu Glu Glu Asn
225                 230
```

<210> SEQ ID NO 7
<211> LENGTH: 1043
<212> TYPE: DNA
<213> ORGANISM: Zea mays

<400> SEQUENCE: 7

```
gccgcgcgtg cacgctgttc gtggatgcag atgggggggcg ccgaggttg gcggggtgga       60
```

-continued

```
ggaggaaggc cgtgctgcga tcggggtgcg cgctctcacg ggtgatgctc ttcgtcttcg    120
ggttctactg gatccgcgag acccgcagaa ggtccactaa tgctaagggt ttaaatcagg    180
accaatttga agaatcccaa aggccagggg caattgtatc taatcatgtc tcttatgtgg    240
atattcttta tcacatgtca gcatcctttc aagttttgt tgctaaggag tcagtgtcca    300
ggttgccact tattggtctc ataagcaatt gtcttggatg cattttgtt caacgagaat    360
cgaagtcttc agaagctaaa ggtgtctcag gcgctgtaac tgaaaggatc aagacgttt    420
gtcaagataa gaatacccca tgatgttgt tgtttcccga gggaactact acaaatgggg    480
attaccttct tccatttaag actggagcct ttcttgcagg tgcaccagtg cagccagtca    540
ttttgaaata cccttacagg agatttagtc cagcatggga ttcaatggat ggagcacgtc    600
atgtgttttt gctgctctgt caatttgtaa atcacatgga ggtggtccgg ttgcctgtat    660
actatccttc tcaactagaa aaagaagatc ctaagctcta cgcaaataat gtcagaaaac    720
taatagcaat ggagggcaat ttagttcttt ctaatattgg gctggcagag aagcgcgtgt    780
accatgcagc actgactggt agtagtctac ctggcgctag acatgagaaa gatgattgaa    840
agacgttgcg tcgcttttc tgtaacagac agccgaggaa cacttaaaaa tgtaactgtg    900
tgcgtgtttt tatacctgta atgtggcagt ttatttgttt gaggaggctg ttgagtaccc    960
ttctcatact acattgtaca aaacaatgt ccaatgtcca ttatagtttg atgaggttcg    1020
tgctccaaaa aaaaaaaaaa aaa                                           1043
```

<210> SEQ ID NO 8
<211> LENGTH: 278
<212> TYPE: PRT
<213> ORGANISM: Zea mays

<400> SEQUENCE: 8

```
Arg Ala Cys Thr Leu Phe Val Asp Ala Asp Gly Gly Arg Pro Arg Leu
 1               5                  10                  15

Ala Gly Trp Arg Arg Lys Ala Val Leu Arg Ser Gly Cys Ala Leu Ser
             20                  25                  30

Arg Val Met Leu Phe Val Phe Gly Phe Tyr Trp Ile Arg Glu Thr Arg
         35                  40                  45

Arg Arg Ser Thr Asn Ala Lys Gly Leu Asn Gln Asp Gln Phe Glu Glu
     50                  55                  60

Ser Gln Arg Pro Gly Ala Ile Val Ser Asn His Val Ser Tyr Val Asp
 65                  70                  75                  80

Ile Leu Tyr His Met Ser Ala Ser Phe Pro Ser Phe Val Ala Lys Glu
                 85                  90                  95

Ser Val Ser Arg Leu Pro Leu Ile Gly Leu Ile Ser Asn Cys Leu Gly
            100                 105                 110

Cys Ile Phe Val Gln Arg Glu Ser Lys Ser Ser Glu Ala Lys Gly Val
        115                 120                 125

Ser Gly Ala Val Thr Glu Arg Ile Gln Asp Val Cys Gln Asp Lys Asn
    130                 135                 140

Thr Pro Met Met Leu Leu Phe Pro Glu Gly Thr Thr Asn Gly Asp
145                 150                 155                 160

Tyr Leu Leu Pro Phe Lys Thr Gly Ala Phe Leu Ala Gly Ala Pro Val
                165                 170                 175

Gln Pro Val Ile Leu Lys Tyr Pro Tyr Arg Arg Phe Ser Pro Ala Trp
            180                 185                 190

Asp Ser Met Asp Gly Ala Arg His Val Phe Leu Leu Leu Cys Gln Phe
```

195                 200                 205
Val Asn His Met Glu Val Val Arg Leu Pro Val Tyr Tyr Pro Ser Gln
    210                 215                 220

Leu Glu Lys Glu Asp Pro Lys Leu Tyr Ala Asn Asn Val Arg Lys Leu
225                 230                 235                 240

Ile Ala Met Glu Gly Asn Leu Val Leu Ser Asn Ile Gly Leu Ala Glu
                245                 250                 255

Lys Arg Val Tyr His Ala Ala Leu Thr Gly Ser Ser Leu Pro Gly Ala
                260                 265                 270

Arg His Glu Lys Asp Asp
        275

<210> SEQ ID NO 9
<211> LENGTH: 1349
<212> TYPE: DNA
<213> ORGANISM: Glycine max

<400> SEQUENCE: 9
aagaacctga cccaggatga ggatcgcgtg agcactcctc ttcagatccg cacaagcatt      60
gcatatcaaa tcaagcatcc tgttccttat ctctgtctct gcatttccct tccttcttct     120
tctctctctc tctctaaaac cctaattcta tacatggaag gaaatctcaa atctaatga     180
ctaattaatt aatccatcga tcaagcatgg agtccgaact caaagacctc aattcgaagc     240
cgccgaacgg caacggcaac agcgttcgcg atgaccgtcc tctgctgaag ccggagcctc     300
cggtctccgc cgacagcatc gccgatatgg agaagaagtt cgccgcttac gtccgccgcg     360
acgtgtacgg caccatggga cgcggcgagt tgcctcccaa ggagaagctc ttgctcggtt     420
cgcgttggt cactcttctc cccattcgag tcgttctcgc cgtcaccata ttgctctttt     480
attacttaat ttgtagggtt tgcactctct tctctgcgcc cactggcgaa gaggaacagg     540
aagattacgc tcacatgagt gggtggagga gaaccattat tgtttcgtgt ggacgcgccc     600
tctccagact catgctttc attttcggct tttattggat ccccgaatcg aactctgcct     660
ctcaggaaga caagagtcgg cagcccgaag agttgaggag acctggcgta ataatttcta     720
atcatgtgtc gtacttggat attttgtatc acatgtcttc ctcattccct agttttgttg     780
ctaagagatc agtggctaaa cttccgctag tcggtctcat cagcaagtgc cttggttgtg     840
tctatgttca gcgggaatca aggtcatcag acttcaaggg tgtttcagct gttgtcactg     900
acagaattcg agaagctcat cagaatgagt ctgctccatt aatgatgtta tttccagaag     960
gtacaaccac aaatggagag ttcctccttc cattcaagac tggtggtttt ttggcaaagg    1020
caccggtact tcctgtgata ttacgatatc attaccagag attagcccct gcctgggatt    1080
ccatatctgg agtgcgccat gtgatatttc tcctgtgtca gtttgtgaat tatatggagg    1140
tgatccgatt acctgtttac catccttcac agcaggagat ggatgatccc aaactatacg    1200
ctaataatgt tagaaggttg atggctactg agggtaattt gatactttct gatattgggc    1260
tagctgaaaa acgaatatat cacgctgctc tcaatggtaa aatagcctg cctagtgttt    1320
tgcatcagaa agacgaatga taatttcat                                     1349

<210> SEQ ID NO 10
<211> LENGTH: 377
<212> TYPE: PRT
<213> ORGANISM: Glycine max

<400> SEQUENCE: 10

-continued

```
Met Glu Ser Glu Leu Lys Asp Leu Asn Ser Lys Pro Pro Asn Gly Asn
 1               5                  10                  15

Gly Asn Ser Val Arg Asp Arg Pro Leu Leu Lys Pro Glu Pro Pro
             20                  25                  30

Val Ser Ala Asp Ser Ile Ala Asp Met Glu Lys Lys Phe Ala Ala Tyr
             35                  40                  45

Val Arg Arg Asp Val Tyr Gly Thr Met Gly Arg Gly Glu Leu Pro Pro
 50                      55                  60

Lys Glu Lys Leu Leu Leu Gly Phe Ala Leu Val Thr Leu Leu Pro Ile
 65              70                  75                      80

Arg Val Val Leu Ala Val Thr Ile Leu Leu Phe Tyr Tyr Leu Ile Cys
                 85                      90                  95

Arg Val Cys Thr Leu Phe Ser Ala Pro Thr Gly Glu Glu Glu Gln Glu
             100                 105                 110

Asp Tyr Ala His Met Ser Gly Trp Arg Arg Thr Ile Ile Val Ser Cys
             115                 120                 125

Gly Arg Ala Leu Ser Arg Leu Met Leu Phe Ile Phe Gly Phe Tyr Trp
 130                 135                 140

Ile Pro Glu Ser Asn Ser Ala Ser Gln Glu Asp Lys Ser Arg Gln Pro
145                 150                 155                 160

Glu Glu Leu Arg Arg Pro Gly Val Ile Ile Ser Asn His Val Ser Tyr
                 165                 170                 175

Leu Asp Ile Leu Tyr His Met Ser Ser Ser Phe Pro Ser Phe Val Ala
             180                 185                 190

Lys Arg Ser Val Ala Lys Leu Pro Leu Val Gly Leu Ile Ser Lys Cys
             195                 200                 205

Leu Gly Cys Val Tyr Val Gln Arg Glu Ser Arg Ser Ser Asp Phe Lys
 210                 215                 220

Gly Val Ser Ala Val Val Thr Asp Arg Ile Arg Glu Ala His Gln Asn
225                 230                 235                 240

Glu Ser Ala Pro Leu Met Met Leu Phe Pro Glu Gly Thr Thr Thr Asn
                 245                 250                 255

Gly Glu Phe Leu Leu Pro Phe Lys Thr Gly Gly Phe Leu Ala Lys Ala
             260                 265                 270

Pro Val Leu Pro Val Ile Leu Arg Tyr His Tyr Gln Arg Phe Ser Pro
             275                 280                 285

Ala Trp Asp Ser Ile Ser Gly Val Arg His Val Ile Phe Leu Leu Cys
         290                 295                 300

Gln Phe Val Asn Tyr Met Glu Val Ile Arg Leu Pro Val Tyr His Pro
305                 310                 315                 320

Ser Gln Gln Glu Met Asp Asp Pro Lys Leu Tyr Ala Asn Asn Val Arg
                 325                 330                 335

Arg Leu Met Ala Thr Glu Gly Asn Leu Ile Leu Ser Asp Ile Gly Leu
             340                 345                 350

Ala Glu Lys Arg Ile Tyr His Ala Ala Leu Asn Gly Asn Asn Ser Leu
             355                 360                 365

Pro Ser Val Leu His Gln Lys Asp Glu
             370                 375

<210> SEQ ID NO 11
<211> LENGTH: 585
<212> TYPE: DNA
<213> ORGANISM: Triticum aestivum
<220> FEATURE:
<221> NAME/KEY: unsure
```

```
<222> LOCATION: (363)
<223> OTHER INFORMATION: n = a, c, g, or t
<220> FEATURE:
<221> NAME/KEY: unsure
<222> LOCATION: (391)
<223> OTHER INFORMATION: n = a, c, g, or t
<220> FEATURE:
<221> NAME/KEY: unsure
<222> LOCATION: (404)
<223> OTHER INFORMATION: n = a, c, g, or t
<220> FEATURE:
<221> NAME/KEY: unsure
<222> LOCATION: (433)
<223> OTHER INFORMATION: n = a, c, g, or t
<220> FEATURE:
<221> NAME/KEY: unsure
<222> LOCATION: (439)
<223> OTHER INFORMATION: n = a, c, g, or t
<220> FEATURE:
<221> NAME/KEY: unsure
<222> LOCATION: (449)
<223> OTHER INFORMATION: n = a, c, g, or t
<220> FEATURE:
<221> NAME/KEY: unsure
<222> LOCATION: (470)
<223> OTHER INFORMATION: n = a, c, g, or t
<220> FEATURE:
<221> NAME/KEY: unsure
<222> LOCATION: (510)
<223> OTHER INFORMATION: n = a, c, g, or t
<220> FEATURE:
<221> NAME/KEY: unsure
<222> LOCATION: (527)
<223> OTHER INFORMATION: n = a, c, g, or t
<220> FEATURE:
<221> NAME/KEY: unsure
<222> LOCATION: (532)
<223> OTHER INFORMATION: n = a, c, g, or t
<220> FEATURE:
<221> NAME/KEY: unsure
<222> LOCATION: (535)
<223> OTHER INFORMATION: n = a, c, g, or t
<220> FEATURE:
<221> NAME/KEY: unsure
<222> LOCATION: (539)
<223> OTHER INFORMATION: n = a, c, g, or t
<220> FEATURE:
<221> NAME/KEY: unsure
<222> LOCATION: (557)
<223> OTHER INFORMATION: n = a, c, g, or t
<220> FEATURE:
<221> NAME/KEY: unsure
<222> LOCATION: (562)
<223> OTHER INFORMATION: n = a, c, g, or t
<220> FEATURE:
<221> NAME/KEY: unsure
<222> LOCATION: (571)
<223> OTHER INFORMATION: n = a, c, g, or t

<400> SEQUENCE: 11
caggggttga ggagggaggc cgtgctgcgt gctggccgcg tgttgtcgcg ggcaatgctg    60
ttcgtgttcg ggttctactg gatccccgtg tccgatcgaa gcttcccaa tgccgaggat    120 gtacctaaag atcactatga agaactggaa agaccagggg cgattgtatc taatcatgtg   180
tcatatgtgg acattcttta tcatatgtca gcttcttctc cgagttttgt tgctaagaac   240
tcagtgtcca agttgccgtt gattggtctc ataagcaaat gtcttgggtg cattttgtt    300 caacgagaac caaatgttca gattctaaag ggtctcaagt gctgtaactg aaagtccatg   360
agntcacaag gacgagaatc cctatatcta nccttcctg aggntacact acaatgggat   420
tactctccat tanacaganc ttcttgcang gacatgcaac tgtatttggn atacctacag   480
agattatcca cctgggacca tgatgggacn caagttttg ccccgnatt tnaantaana   540
```
aggtcccctt ctgaaanact cncaaaaaga ngttcaatca gcaaa                    585

<210> SEQ ID NO 12
<211> LENGTH: 194
<212> TYPE: PRT
<213> ORGANISM: Triticum aestivum
<220> FEATURE:
<221> NAME/KEY: UNSURE
<222> LOCATION: (120)
<223> OTHER INFORMATION: Xaa = any amino acid
<220> FEATURE:
<221> NAME/KEY: UNSURE
<222> LOCATION: (130)
<223> OTHER INFORMATION: Xaa = any amino acid
<220> FEATURE:
<221> NAME/KEY: UNSURE
<222> LOCATION: (134)
<223> OTHER INFORMATION: Xaa = any amino acid
<220> FEATURE:
<221> NAME/KEY: UNSURE
<222> LOCATION: (144)
<223> OTHER INFORMATION: Xaa = any amino acid
<220> FEATURE:
<221> NAME/KEY: UNSURE
<222> LOCATION: (146)
<223> OTHER INFORMATION: Xaa = any amino acid
<220> FEATURE:
<221> NAME/KEY: UNSURE
<222> LOCATION: (149)
<223> OTHER INFORMATION: Xaa = any amino acid
<220> FEATURE:
<221> NAME/KEY: UNSURE
<222> LOCATION: (156)
<223> OTHER INFORMATION: Xaa = any amino acid
<220> FEATURE:
<221> NAME/KEY: UNSURE
<222> LOCATION: (175)
<223> OTHER INFORMATION: Xaa = any amino acid
<220> FEATURE:
<221> NAME/KEY: UNSURE
<222> LOCATION: (177)..(178)..(179)
<223> OTHER INFORMATION: Xaa = any amino acid
<220> FEATURE:
<221> NAME/KEY: UNSURE
<222> LOCATION: (185)
<223> OTHER INFORMATION: Xaa = any amino acid
<220> FEATURE:
<221> NAME/KEY: UNSURE
<222> LOCATION: (187)
<223> OTHER INFORMATION: Xaa = any amino acid
<220> FEATURE:
<221> NAME/KEY: UNSURE
<222> LOCATION: (190)
<223> OTHER INFORMATION: Xaa = any amino acid

<400> SEQUENCE: 12

Gln Gly Leu Arg Arg Glu Ala Val Leu Arg Ala Gly Arg Val Leu Ser
 1               5                  10                  15

Arg Ala Met Leu Phe Val Phe Gly Phe Tyr Trp Ile Pro Val Ser Asp
                20                  25                  30

Arg Ser Phe Pro Asn Ala Glu Asp Val Pro Lys Asp His Tyr Glu Glu
            35                  40                  45

Leu Glu Arg Pro Gly Ala Ile Val Ser Asn His Val Ser Tyr Val Asp
        50                  55                  60

Ile Leu Tyr His Met Ser Ala Ser Pro Ser Phe Val Ala Lys Asn
 65                 70                  75                  80

Ser Val Ser Lys Leu Pro Leu Ile Gly Leu Ile Ser Lys Cys Leu Gly
                85                  90                  95

Cys Ile Phe Val Gln Arg Glu Pro Asn Val Gln Ile Leu Lys Gly Leu
            100                 105                 110

```
Lys Cys Cys Asn Lys Ser Met Xaa Ser Gln Gly Arg Glu Ser Leu Tyr
        115                 120                 125

Leu Xaa Phe Pro Glu Xaa Thr Leu Gln Trp Asp Tyr Ser Pro Leu Xaa
130                 135                 140

Arg Xaa Ser Cys Xaa Asp Met Gln Leu Tyr Leu Xaa Tyr Leu Gln Arg
145                 150                 155                 160

Leu Ser Thr Trp Asp His Asp Gly Thr Gln Val Phe Ala Pro Xaa Phe
                165                 170                 175

Xaa Xaa Xaa Arg Val Pro Ser Glu Xaa Leu Xaa Lys Arg Xaa Ser Ile
            180                 185                 190

Ser Lys
```

<210> SEQ ID NO 13
<211> LENGTH: 1501
<212> TYPE: DNA
<213> ORGANISM: Arabidopsis thaliana

<400> SEQUENCE: 13

```
atgcagaatc atgtggatta ctcggatctg taccagatgt atcctcttct cttttggcta      60
tcagtggata agaaggaaag ggaaacctgc tcggagagag attgctccga ttgttgtatc     120
aaatcatgtt tcttatattg aaccaatctt ctacttctat gaattatcac cgaccattgt     180
tgcatcggag tcacatgatt cacttccatt tgttggaact attatcaggg caatgcaggt     240
gatatatgtg aatagattct cacagacatc aaggaagaat gctgtgcatg aaataaagag     300
aaaagcttcc tgcgatagat ttcctcgtct gctgttattc cccgaaggaa ccacgactaa     360
tgggaaagtt cttatttcct tccaactcgg tgctttcatc cctggttacc ctattcaacc     420
tgtagtagtc cggtatcccc atgtacattt tgatcaatcc tggggaaata tctctttgtt     480
gacgctcatg tttagaatgt tcactcagtt tcacaatttc atggaggttg aatatcttcc     540
tgtaatctat cccagtgaaa agcaaaagca gaatgctgtg cgtctctcac agaagactag     600
tcatgcaatt gcaacatctt tgaatgtcgt ccaaacatcc cattcttttg cggacttgat     660
gctactcaac aaagcaactg agttaaagct ggagaacccc tcaaattaca tggttgaaat     720
ggcaagagtt gagtcgctat tccatgtaag cagcttagag gcaacgcgat ttttggatac     780
atttgttttcc atgattccgg actcgagtgg acgtgttagg ctacatgact tcttcgggg     840
tcttaaactg aaaccttgcc ctctttctaa aaggatattt gagttcatcg atgtggagaa     900
ggtcggatca atcactttca acagttcttg gtttgcctcg ggccacgtgt tgacacagcc     960
gcttttaag caaacatgcg agctagcctt tcccattgc gatgcagatg gagatggcta    1020
tattacaatt caagaactcg agaagctctc aaaaacaca atcccaaact gaacaagga    1080
cgagattcga ggaatgtacc atttgctaga cgacgaccaa gatcaaagaa tcagccaaaa    1140
tgacttgttg tcctgcttaa gaagaaaccc tcttctcata gccatctttg cacctgactt    1200
ggccccaaca taacacagag agacaaaatg gctggctaag atttgtggtg cgatgattgt    1260
aaacttgtct tgtggtata ttattatacc ttttgtttg tcttcatatt tgatttcagc    1320
tagtaaaaag aagggactgc tatgttttta gcctatatat ataccctcct ccaacatgga    1380
tccatccttt tgagtgttgg actataactg cttgtcgttt tccaccccaa aaacgctat    1440
ggtgtttgct cctctagttc tgagcaaact ttgctgtaaa aaaaaaaaaa aaaaaaaaaa    1500
a                                                                  1501
```

<210> SEQ ID NO 14

```
<211> LENGTH: 403
<212> TYPE: PRT
<213> ORGANISM: Arabidopsis thaliana

<400> SEQUENCE: 14

Cys Arg Ile Met Trp Ile Thr Arg Ile Cys Thr Arg Cys Ile Leu Phe
1               5                   10                  15

Ser Phe Gly Tyr Gln Trp Ile Arg Arg Lys Gly Lys Pro Ala Arg Arg
            20                  25                  30

Glu Ile Ala Pro Ile Val Val Ser Asn His Val Ser Tyr Ile Glu Pro
        35                  40                  45

Ile Phe Tyr Phe Tyr Glu Leu Ser Pro Thr Ile Val Ala Ser Glu Ser
    50                  55                  60

His Asp Ser Leu Pro Phe Val Gly Thr Ile Ile Arg Ala Met Gln Val
65                  70                  75                  80

Ile Tyr Val Asn Arg Phe Ser Gln Thr Ser Arg Lys Asn Ala Val His
                85                  90                  95

Glu Ile Lys Arg Lys Ala Ser Cys Asp Arg Phe Pro Arg Leu Leu Leu
            100                 105                 110

Phe Pro Glu Gly Thr Thr Thr Asn Gly Lys Val Leu Ile Ser Phe Gln
        115                 120                 125

Leu Gly Ala Phe Ile Pro Gly Tyr Pro Ile Gln Pro Val Val Val Arg
    130                 135                 140

Tyr Pro His Val His Phe Asp Gln Ser Trp Gly Asn Ile Ser Leu Leu
145                 150                 155                 160

Thr Leu Met Phe Arg Met Phe Thr Gln Phe His Asn Phe Met Glu Val
                165                 170                 175

Glu Tyr Leu Pro Val Ile Tyr Pro Ser Glu Lys Gln Lys Gln Asn Ala
            180                 185                 190

Val Arg Leu Ser Gln Lys Thr Ser His Ala Ile Ala Thr Ser Leu Asn
        195                 200                 205

Val Val Gln Thr Ser His Ser Phe Ala Asp Leu Met Leu Leu Asn Lys
    210                 215                 220

Ala Thr Glu Leu Lys Leu Glu Asn Pro Ser Asn Tyr Met Val Glu Met
225                 230                 235                 240

Ala Arg Val Glu Ser Leu Phe His Val Ser Ser Leu Glu Ala Thr Arg
                245                 250                 255

Phe Leu Asp Thr Phe Val Ser Met Ile Pro Asp Ser Ser Gly Arg Val
            260                 265                 270

Arg Leu His Asp Phe Leu Arg Gly Leu Lys Leu Lys Pro Cys Pro Leu
        275                 280                 285

Ser Lys Arg Ile Phe Glu Phe Ile Asp Val Glu Lys Val Gly Ser Ile
    290                 295                 300

Thr Phe Lys Gln Phe Leu Phe Ala Ser Gly His Val Leu Thr Gln Pro
305                 310                 315                 320

Leu Phe Lys Gln Thr Cys Glu Leu Ala Phe Ser His Cys Asp Ala Asp
                325                 330                 335

Gly Asp Gly Tyr Ile Thr Ile Gln Glu Leu Gly Glu Ala Leu Lys Asn
            340                 345                 350

Thr Ile Pro Asn Leu Asn Lys Asp Glu Ile Arg Gly Met Tyr His Leu
        355                 360                 365

Leu Asp Asp Asp Gln Asp Gln Arg Ile Ser Gln Asn Asp Leu Leu Ser
    370                 375                 380

Cys Leu Arg Arg Asn Pro Leu Leu Ile Ala Ile Phe Ala Pro Asp Leu
```

Ala Pro Thr

<210> SEQ ID NO 15
<211> LENGTH: 692
<212> TYPE: DNA
<213> ORGANISM: Oryza sativa
<220> FEATURE:
<221> NAME/KEY: unsure
<222> LOCATION: (446)
<223> OTHER INFORMATION: n = a, c, g, or t
<220> FEATURE:
<221> NAME/KEY: unsure
<222> LOCATION: (579)
<223> OTHER INFORMATION: n = a, c, g, or t
<220> FEATURE:
<221> NAME/KEY: unsure
<222> LOCATION: (677)
<223> OTHER INFORMATION: n = a, c, g, or t

<400> SEQUENCE: 15

```
gttctaaccc gcctcctctc gcctcgcctc cgccacccat ggcttctcga accctagcc      60
ccgcctccct ctccacgccg ctcctctccg actccatctc gcccacgccc accaccaacg    120
gccacgcggg gcaccataac cacgacgacg acgacgagga gtcgccaacg gtgtgcggcg    180
gcgatggcgg aggaggggg gacccgttcg cgttcctatc ggaggatcgg ccggcgtggt     240
ggtcgccgcg gggggtgtcc ccggccgacc cgttccgcaa cgggacgccg gggtggtgcg    300
gggcgtacga gctcgtgagg gcgctcgtgt gcgcgccggt ggcggcggcg aggctggtgc    360
tgttcgggct ctccatcgcg gtggggtacg ccgccacgtg ggtggcgctc cgcgggtggg    420
tcgacgtgcg ggagcgggcg gcgcangagg gcgccgggcc catgccggcg tggcgccgcc    480
gcctcatgtg gatcacgcgg attccgcgcg ctgcatcctc ttctccttcg gatacattgg    540
ataaggagaa aggaaaaccg ccctagaaac ttcactatnt ttctaaatca tgttcatcat    600
agaaccatat actctcatag cttccgacat cgttctcaaa tccatatcat acattttgaa    660
aatttcagca tcagtantag ttaaaatccc aa                                  692
```

<210> SEQ ID NO 16
<211> LENGTH: 174
<212> TYPE: PRT
<213> ORGANISM: Oryza sativa
<220> FEATURE:
<221> NAME/KEY: UNSURE
<222> LOCATION: (136)
<223> OTHER INFORMATION: Xaa = any amino acid

<400> SEQUENCE: 16

Met Ala Ser Arg Asn Pro Ser Pro Ala Ser Leu Ser Thr Pro Leu Leu
1               5                   10                  15

Ser Asp Ser Ile Ser Pro Thr Pro Thr Thr Asn Gly His Ala Gly His
            20                  25                  30

His Asn His Asp Asp Asp Asp Glu Glu Ser Pro Thr Val Cys Gly Gly
        35                  40                  45

Asp Gly Gly Gly Gly Asp Pro Phe Ala Phe Leu Ser Glu Asp Arg
    50                  55                  60

Pro Ala Trp Trp Ser Pro Arg Gly Val Ser Pro Ala Asp Pro Phe Arg
65                  70                  75                  80

Asn Gly Thr Pro Gly Trp Cys Gly Ala Tyr Glu Leu Val Arg Ala Leu
                85                  90                  95

Val Cys Ala Pro Val Ala Ala Ala Arg Leu Val Leu Phe Gly Leu Ser

-continued

```
                            100                 105                 110
Ile Ala Val Gly Tyr Ala Ala Thr Trp Val Ala Leu Arg Gly Trp Val
            115                 120                 125

Asp Val Arg Glu Arg Ala Ala Xaa Glu Gly Ala Gly Pro Met Pro Ala
130                 135                 140

Trp Arg Arg Arg Leu Met Trp Ile Thr Arg Ile Pro Arg Ala Ala Ser
145                 150                 155                 160

Ser Ser Pro Ser Asp Thr Leu Asp Lys Glu Lys Gly Lys Pro
                165                 170

<210> SEQ ID NO 17
<211> LENGTH: 480
<212> TYPE: DNA
<213> ORGANISM: Glycine max
<220> FEATURE:
<221> NAME/KEY: unsure
<222> LOCATION: (189)
<223> OTHER INFORMATION: n = a, c, g, or t
<220> FEATURE:
<221> NAME/KEY: unsure
<222> LOCATION: (195)
<223> OTHER INFORMATION: n = a, c, g, or t
<220> FEATURE:
<221> NAME/KEY: unsure
<222> LOCATION: (284)
<223> OTHER INFORMATION: n = a, c, g, or t
<220> FEATURE:
<221> NAME/KEY: unsure
<222> LOCATION: (290)
<223> OTHER INFORMATION: n = a, c, g, or t
<220> FEATURE:
<221> NAME/KEY: unsure
<222> LOCATION: (303)
<223> OTHER INFORMATION: n = a, c, g, or t
<220> FEATURE:
<221> NAME/KEY: unsure
<222> LOCATION: (362)
<223> OTHER INFORMATION: n = a, c, g, or t
<220> FEATURE:
<221> NAME/KEY: unsure
<222> LOCATION: (366)
<223> OTHER INFORMATION: n = a, c, g, or t
<220> FEATURE:
<221> NAME/KEY: unsure
<222> LOCATION: (377)..(378)
<223> OTHER INFORMATION: n = a, c, g, or t
<220> FEATURE:
<221> NAME/KEY: unsure
<222> LOCATION: (399)
<223> OTHER INFORMATION: n = a, c, g, or t
<220> FEATURE:
<221> NAME/KEY: unsure
<222> LOCATION: (419)
<223> OTHER INFORMATION: n = a, c, g, or t
<220> FEATURE:
<221> NAME/KEY: unsure
<222> LOCATION: (426)
<223> OTHER INFORMATION: n = a, c, g, or t
<220> FEATURE:
<221> NAME/KEY: unsure
<222> LOCATION: (428)
<223> OTHER INFORMATION: n = a, c, g, or t
<220> FEATURE:
<221> NAME/KEY: unsure
<222> LOCATION: (432)
<223> OTHER INFORMATION: n = a, c, g, or t
<220> FEATURE:
<221> NAME/KEY: unsure
<222> LOCATION: (454)
<223> OTHER INFORMATION: n = a, c, g, or t
<220> FEATURE:
<221> NAME/KEY: unsure
<222> LOCATION: (475)
<223> OTHER INFORMATION: n = a, c, g, or t
```

<400> SEQUENCE: 17

```
gcgacgacga cgacttctcc gtgccgccac cgtccaccct ggacccgttc cgcaaccgca      60
cgccggcgat cgaggggctc tacgagtggg ccaagacggc gctgtgcctg ccgctggcgg     120
cgctgcggct cgcgctgttc gggctctgcc tcgcggtggg gtacgtggcg acgaaggtgg     180
cgctggcang gtggnaggac aaggagaatc ccatgcccaa gtggaggtgt agggttatgt     240
ggatcacgcg cttgtgcgcc aaatgtattc tcttctcctt tggntatcan tggataaaac     300
ggnaagggaa acctgcacca aggggaaatt gctccaataa attgtatcta aaccatgttt     360
cntaanagtg agcctannct tcctatttct aagaattant tcctaacaat ggtgggaanc     420
tgaagncnca anactccata tccttttgtt gggnaccaat taatagagca aatgnaagtc     480
```

<210> SEQ ID NO 18
<211> LENGTH: 107
<212> TYPE: PRT
<213> ORGANISM: Glycine max
<220> FEATURE:
<221> NAME/KEY: UNSURE
<222> LOCATION: (63)
<223> OTHER INFORMATION: Xaa = any amino acid
<220> FEATURE:
<221> NAME/KEY: UNSURE
<222> LOCATION: (65)
<223> OTHER INFORMATION: Xaa = any amino acid
<220> FEATURE:
<221> NAME/KEY: UNSURE
<222> LOCATION: (96)
<223> OTHER INFORMATION: Xaa = any amino acid
<220> FEATURE:
<221> NAME/KEY: UNSURE
<222> LOCATION: (101)
<223> OTHER INFORMATION: Xaa = any amino acid

<400> SEQUENCE: 18

```
Asp Asp Asp Asp Phe Ser Val Pro Pro Ser Thr Leu Asp Pro Phe
  1               5                  10                  15

Arg Asn Arg Thr Pro Ala Ile Glu Gly Leu Tyr Glu Trp Ala Lys Thr
             20                  25                  30

Ala Leu Cys Leu Pro Leu Ala Ala Leu Arg Leu Ala Leu Phe Gly Leu
         35                  40                  45

Cys Leu Ala Val Gly Tyr Val Ala Thr Lys Val Ala Leu Ala Xaa Trp
     50                  55                  60

Xaa Asp Lys Glu Asn Pro Met Pro Lys Trp Arg Cys Arg Val Met Trp
 65                  70                  75                  80

Ile Thr Arg Leu Cys Ala Lys Cys Ile Leu Phe Ser Phe Gly Tyr Xaa
                 85                  90                  95

Trp Ile Lys Arg Xaa Gly Lys Pro Ala Pro Arg
            100                 105
```

<210> SEQ ID NO 19
<211> LENGTH: 784
<212> TYPE: DNA
<213> ORGANISM: Oryza sativa
<220> FEATURE:
<221> NAME/KEY: unsure
<222> LOCATION: (560)
<223> OTHER INFORMATION: n = a, c, g, or t
<220> FEATURE:
<221> NAME/KEY: unsure
<222> LOCATION: (648)
<223> OTHER INFORMATION: n = a, c, g, or t
<220> FEATURE:
<221> NAME/KEY: unsure

```
<222> LOCATION: (670)
<223> OTHER INFORMATION: n = a, c, g, or t
<220> FEATURE:
<221> NAME/KEY: unsure
<222> LOCATION: (739)
<223> OTHER INFORMATION: n = a, c, g, or t
<220> FEATURE:
<221> NAME/KEY: unsure
<222> LOCATION: (758)
<223> OTHER INFORMATION: n = a, c, g, or t

<400> SEQUENCE: 19
cttctcgtcg ccggtggatt cgccgccgcc tccgccgccg ccgccggagg aggaggacga      60
ggagagggcg ctccctcggg ggtgagcatc cagccacctc ggcccgttgc ctcctcttcg     120
catctcggcc ccgcgagatt ggaagtgagg gcagggcagg gcggcagggg ccatggcggt     180
cccactcgtg ctcgtcgtgc tcccgctcgg cctcctcttc ctcctctccg gcctcaacgc     240
catccaggcc gtcctgtttc tctcgataag gccgttctcg aagagcttgt accggcggat     300
caacaggttc ttggccgagc tgctgtggct tcagctggtc tggcttgtgg attggtgggc     360
aggagttaag atacaactgc atgctgatga cgaaacttac aaggcaatgg ggaatgagca     420
tgcacttgtc atatcaaatc atcggagcga tatcgattgg cttattgggt ggattttggg     480
cacagcgctc aaggatgcct tgggaagtac acttgctgtt atgaagaaac atccgaaatc     540
cttccaatta ttgggctggn ccatgttgtt tgcagaatac ccctttttgg gaaaggact       600 gggcaaagga tgaaaagaca ttgaaatggg ggccccaaa ggttgaanga cttccccaga     660
catttgggcn accctttttg tttaaggacc cccttaccca acaaaactcc aacaactcaa     720
ggagtatctg ttcacaggnt tgcaacacca agaaatgnat gatcacgtca aagggattgt     780
acac                                                                  784

<210> SEQ ID NO 20
<211> LENGTH: 146
<212> TYPE: PRT
<213> ORGANISM: Oryza sativa
<220> FEATURE:
<221> NAME/KEY: UNSURE
<222> LOCATION: (130)
<223> OTHER INFORMATION: Xaa = any amino acid

<400> SEQUENCE: 20

Met Ala Val Pro Leu Val Leu Val Val Leu Pro Leu Gly Leu Leu Phe
  1               5                  10                  15

Leu Leu Ser Gly Leu Asn Ala Ile Gln Ala Val Leu Phe Leu Ser Ile
             20                  25                  30

Arg Pro Phe Ser Lys Ser Leu Tyr Arg Arg Ile Asn Arg Phe Leu Ala
         35                  40                  45

Glu Leu Leu Trp Leu Gln Leu Val Trp Leu Val Asp Trp Trp Ala Gly
     50                  55                  60

Val Lys Ile Gln Leu His Ala Asp Asp Glu Thr Tyr Lys Ala Met Gly
 65                  70                  75                  80

Asn Glu His Ala Leu Val Ile Ser Asn His Arg Ser Asp Ile Asp Trp
                 85                  90                  95

Leu Ile Gly Trp Ile Leu Gly Thr Ala Leu Lys Asp Ala Leu Gly Ser
            100                 105                 110

Thr Leu Ala Val Met Lys Lys His Pro Lys Ser Phe Gln Leu Leu Gly
        115                 120                 125

Trp Xaa Met Leu Phe Ala Glu Tyr Pro Phe Leu Gly Lys Gly Leu Gly
    130                 135                 140
```

```
Lys Gly
145

<210> SEQ ID NO 21
<211> LENGTH: 584
<212> TYPE: DNA
<213> ORGANISM: Glycine max
<220> FEATURE:
<221> NAME/KEY: unsure
<222> LOCATION: (17)..(18)
<223> OTHER INFORMATION: n = a, c, g, or t
<220> FEATURE:
<221> NAME/KEY: unsure
<222> LOCATION: (33)
<223> OTHER INFORMATION: n = a, c, g, or t
<220> FEATURE:
<221> NAME/KEY: unsure
<222> LOCATION: (38)..(39)
<223> OTHER INFORMATION: n = a, c, g, or t
<220> FEATURE:
<221> NAME/KEY: unsure
<222> LOCATION: (519)
<223> OTHER INFORMATION: n = a, c, g, or t
<220> FEATURE:
<221> NAME/KEY: unsure
<222> LOCATION: (543)
<223> OTHER INFORMATION: n = a, c, g, or t
<220> FEATURE:
<221> NAME/KEY: unsure
<222> LOCATION: (546)
<223> OTHER INFORMATION: n = a, c, g, or t
<220> FEATURE:
<221> NAME/KEY: unsure
<222> LOCATION: (575)
<223> OTHER INFORMATION: n = a, c, g, or t

<400> SEQUENCE: 21
cgtttgctga cctgacnncg ggtttttttt ttngggggnnc acggtgtttc gttgcgttgt    60
gctctgctct gctcctttgg gcctgggctg ggctgggctg ggctgggctg ggcatggcta   120
ttgcagcagc ggccgtggtg gtaccattgg gcctgctctt cttcgcctcc ggcctccttg   180
ttaatctcat tcaggcaata tgctatgtcg tcgtaaggcc ggtgtcgaaa agtttgtaca   240
gaaggatcaa ccgggtagta gcagagctct tgtggctgga gcttgtatgg cttattgatt   300
ggtgggcagg agttaaggtc caaatattca cagatcatga aacctttcgt ttaatgggta   360
aagagcatgc acttgtgata agcaatcaca gaagtgatat tgattggctt gttggatggg   420
tttcagctca gcgttcaggt tgtcttggca gcactctaag ctgtgatgaa gaaatcttca   480
aagtttctgc cggtcattgg ctggtcaatg tggttttcng agtaaccttt tctggagaag   540
aanttnggcc aaagatgaaa gcccattaaa gtcangcatc ccgg                   584

<210> SEQ ID NO 22
<211> LENGTH: 116
<212> TYPE: PRT
<213> ORGANISM: Glycine max

<400> SEQUENCE: 22

Met Ala Ile Ala Ala Ala Ala Val Val Val Pro Leu Gly Leu Leu Phe
 1               5                  10                  15

Phe Ala Ser Gly Leu Leu Val Asn Leu Ile Gln Ala Ile Cys Tyr Val
                20                  25                  30

Val Val Arg Pro Val Ser Lys Ser Leu Tyr Arg Arg Ile Asn Arg Val
            35                  40                  45

Val Ala Glu Leu Leu Trp Leu Glu Leu Val Trp Leu Ile Asp Trp Trp
        50                  55                  60
```

Ala Gly Val Lys Val Gln Ile Phe Thr Asp His Glu Thr Phe Arg Leu
65                  70                  75                  80

Met Gly Lys Glu His Ala Leu Val Ile Ser Asn His Arg Ser Asp Ile
                85                  90                  95

Asp Trp Leu Val Gly Trp Val Ser Ala Gln Arg Ser Gly Cys Leu Gly
            100                 105                 110

Ser Thr Leu Ser
        115

<210> SEQ ID NO 23
<211> LENGTH: 570
<212> TYPE: DNA
<213> ORGANISM: Triticum aestivum
<220> FEATURE:
<221> NAME/KEY: unsure
<222> LOCATION: (510)
<223> OTHER INFORMATION: n = a, c, g, or t
<220> FEATURE:
<221> NAME/KEY: unsure
<222> LOCATION: (516)
<223> OTHER INFORMATION: n = a, c, g, or t
<220> FEATURE:
<221> NAME/KEY: unsure
<222> LOCATION: (518)
<223> OTHER INFORMATION: n = a, c, g, or t

<400> SEQUENCE: 23
gagaggagac gcggcggcgg ccatggcgat tcccctcgtg ctcgtcctgc tcccgctcgg     60
cctcctcttc ctcctctccg gcctcgtcgt caacactgtc caggccgtat tgttcttgac    120
gataaggcca ttctcgaagc gattgtaccg gcagatcaac gtattcctgg ccgagttgtt    180
gtggcttcag ctgatctggc ttgtggactg gtgggcaggt attaaggtac aggtgtatgc    240
ggatccagaa acttggaaac taatgggcaa agagcacgcc cttctcatat ccaatcatcg    300
aagtgacatt gattggctgg ttggatggat tttagcacag cgttcaggat gtcttggaag    360
cgcaatagct ataatgaaga aatcctcaaa gttccttcca gttattggtt ggtccatgtg    420
gtttgcagaa tactcttttg gagagaactg gcaaaggatg aaaaacacta aatcgggtct    480
caaggtgaaa actccagata ttggctgccn tttgtnaggg tcaaattact cacaaacttt    540
acagtaagaa atcatccaag ggttgcacgc                                     570

<210> SEQ ID NO 24
<211> LENGTH: 160
<212> TYPE: PRT
<213> ORGANISM: Triticum aestivum

<400> SEQUENCE: 24

Met Ala Ile Pro Leu Val Leu Val Leu Leu Pro Leu Gly Leu Leu Phe
1               5                   10                  15

Leu Leu Ser Gly Leu Val Val Asn Thr Val Gln Ala Val Leu Phe Leu
            20                  25                  30

Thr Ile Arg Pro Phe Ser Lys Arg Leu Tyr Arg Gln Ile Asn Val Phe
        35                  40                  45

Leu Ala Glu Leu Leu Trp Leu Gln Leu Ile Trp Leu Val Asp Trp Trp
    50                  55                  60

Ala Gly Ile Lys Val Gln Val Tyr Ala Asp Pro Glu Thr Trp Lys Leu
65                  70                  75                  80

Met Gly Lys Glu His Ala Leu Leu Ile Ser Asn His Arg Ser Asp Ile
                85                  90                  95

```
Asp Trp Leu Val Gly Trp Ile Leu Ala Gln Arg Ser Gly Cys Leu Gly
            100                 105                 110

Ser Ala Ile Ala Ile Met Lys Lys Ser Ser Lys Phe Leu Pro Val Ile
        115                 120                 125

Gly Trp Ser Met Trp Phe Ala Glu Tyr Ser Phe Gly Glu Asn Trp Gln
    130                 135                 140

Arg Met Lys Asn Thr Lys Ser Gly Leu Lys Val Lys Thr Pro Asp Ile
145                 150                 155                 160

<210> SEQ ID NO 25
<211> LENGTH: 1337
<212> TYPE: DNA
<213> ORGANISM: Catalpa speciosa

<400> SEQUENCE: 25
gcacgagagg ctaaaggaca atgagcaagc taaaaacatc cagctccgaa ttggatttgg      60
atcaccccaa tatcgaagac tatcttccat ccggatccat tcaagagcct cacggcaagc     120
tccgcctgcg tgatttgctc gatatttcac caactctaac tgaggcagct ggtgccattg     180
ttgatgactc cttcacgaga tgcttcaagt caaatccgcc agaaccctgg aactggaaca     240
tatatttgtt tcctttgtgg tgcttaggag ttgttgtcag atatggtctt cttttcccct     300
taagggtaat agtgttgaca ataggatgga ttatatttct ctcatgctat ttccctgtgc     360
atttcctgtt aaagggcat gacaaattga aaaaaaatt agagagaggt ctagtggagt       420
tgatgtgcag ttttttgtt gcatcatgga ctggggttgt caagtaccat ggtccgcggc      480
ccagcatgcg gcctaagcag ttttttgtgg ctaatcacac atccatgatt gatttcattg     540
ttttggaaca aatgactgca tttgcagtga ttatgcagaa gcatcctggg tgggtaggac     600
tattgcagag cactattttg gagagtctag gatgtatctg gttcaaccgg tcagagtcca     660
aggaccgtga aattgttgca aaaaagctaa gagatcatgt ccatggcgct gataataatc     720
ctcttcttat attcccggaa ggaacatgtg tgaataacca ctacactgtg atgtttaaga     780
agggtgcatt tgaacttgga tgcactgtct gtccaatcgc aatcaagtat aacaagattt     840
tgtggatgc cttctggaac agcagaaagc aatcctttac aatgcacttg ttgcagctta     900
tgacatcctg gctgttgtc tgtgatgttt ggtacctgga gcctcaaaat ctaaaacctg      960
gggaaacacc aattgaattt gctgagaggg tgagggcat tatttctgtt cgagcaggcc    1020
ttaagaaggt gccgtgggat ggatatttga agtactctcg ccccagccca agcatcgtg    1080
agcgaaagca acaaagcttc gcagagtcag ttctccatca cctggaagag aaatagattg    1140
aagataaata attttgttat ttactgtctt caatttgtta gatcaagttt gttagctgtt    1200
ttgaaattca atcttatttg tcactataaa gaggatttca gttcctcaat tgacataatg    1260
aaattccttt gatacgtcgt tgaagaggaa aatacaatat gaagtgttga aaaaaaaaa    1320
aaaaaaaaaa aaaaaaaa                                                  1337

<210> SEQ ID NO 26
<211> LENGTH: 371
<212> TYPE: PRT
<213> ORGANISM: Catalpa speciosa

<400> SEQUENCE: 26

Met Ser Lys Leu Lys Thr Ser Ser Glu Leu Asp Leu Asp His Pro
 1               5                  10                  15

Asn Ile Glu Asp Tyr Leu Pro Ser Gly Ser Ile Gln Glu Pro His Gly
            20                  25                  30
```

```
Lys Leu Arg Leu Arg Asp Leu Leu Asp Ile Ser Pro Thr Leu Thr Glu
         35                  40                  45

Ala Ala Gly Ala Ile Val Asp Asp Ser Phe Thr Arg Cys Phe Lys Ser
     50                  55                  60

Asn Pro Pro Glu Pro Trp Asn Trp Asn Ile Tyr Leu Phe Pro Leu Trp
 65                  70                  75                  80

Cys Leu Gly Val Val Arg Tyr Gly Leu Leu Phe Pro Leu Arg Val
                 85                  90                  95

Ile Val Leu Thr Ile Gly Trp Ile Ile Phe Leu Ser Cys Tyr Phe Pro
                100                 105                 110

Val His Phe Leu Leu Lys Gly His Asp Lys Leu Arg Lys Lys Leu Glu
            115                 120                 125

Arg Gly Leu Val Glu Leu Met Cys Ser Phe Phe Val Ala Ser Trp Thr
        130                 135                 140

Gly Val Val Lys Tyr His Gly Pro Arg Pro Ser Met Arg Pro Lys Gln
145                 150                 155                 160

Val Phe Val Ala Asn His Thr Ser Met Ile Asp Phe Ile Val Leu Glu
                165                 170                 175

Gln Met Thr Ala Phe Ala Val Ile Met Gln Lys His Pro Gly Trp Val
            180                 185                 190

Gly Leu Leu Gln Ser Thr Ile Leu Glu Ser Leu Gly Cys Ile Trp Phe
        195                 200                 205

Asn Arg Ser Glu Ser Lys Asp Arg Glu Ile Val Ala Lys Lys Leu Arg
    210                 215                 220

Asp His Val His Gly Ala Asp Asn Asn Pro Leu Leu Ile Phe Pro Glu
225                 230                 235                 240

Gly Thr Cys Val Asn Asn His Tyr Thr Val Met Phe Lys Lys Gly Ala
                245                 250                 255

Phe Glu Leu Gly Cys Thr Val Cys Pro Ile Ala Ile Lys Tyr Asn Lys
            260                 265                 270

Ile Phe Val Asp Ala Phe Trp Asn Ser Arg Lys Gln Ser Phe Thr Met
        275                 280                 285

His Leu Leu Gln Leu Met Thr Ser Trp Ala Val Val Cys Asp Val Trp
    290                 295                 300

Tyr Leu Glu Pro Gln Asn Leu Lys Pro Gly Thr Pro Ile Glu Phe
305                 310                 315                 320

Ala Glu Arg Val Arg Gly Ile Ile Ser Val Arg Ala Gly Leu Lys Lys
                325                 330                 335

Val Pro Trp Asp Gly Tyr Leu Lys Tyr Ser Arg Pro Ser Pro Lys His
            340                 345                 350

Arg Glu Arg Lys Gln Gln Ser Phe Ala Glu Ser Val Leu His His Leu
        355                 360                 365

Glu Glu Lys
    370

<210> SEQ ID NO 27
<211> LENGTH: 1582
<212> TYPE: DNA
<213> ORGANISM: Zea mays

<400> SEQUENCE: 27
cctcgcccca tcgcggacct ttcctcggcg gcgtcgccat ctcatcggcg gcgggcgtgc     60
ggccggtggc cgaagccctt aggcgatggc gacctcgtct gtggcggcgg acatggagct    120
```

```
ggaccggcca aacctggagg actacctccc gcccgactcg ctcccgcagg aggcgccccg    180
gaatctccat ctgcgcgatc tgctggacat ctcgccggtg ctcaccgagg cagcgggtgc    240
cattgtcgat gactccttca cacggtgctt taagtcaaat tctccagagc catggaattg    300
gaacatatat ctgttcccct tatggtgctt tggtgtagta ataagatatg gattactctt    360
cccactgagg tccttaacgc ttgcaatagg atggttagca ttttttgctg ccttttttcc    420
tgtccatttc ctattgaaag gtcaagacaa gttgagaagt aaaattgaga ggaagttggt    480
tgaaatgatg tgcagtgttt ttgttgcttc atggactgga gttatcaagt atcatggacc    540
acgcccaagc acacgacctc atcaggtatt cgttgcaaac catacatcga tgatagattt    600
cattattctg gagcaaatga cagcatttgc tgtcatcatg cagaagcatc ctggatgggt    660
tggatttatt cagaagacta tcttggaaag tgtcggttgc atctggttta atcgtaatga    720
tctccgggac cgtgaagtta cggcacggaa gttacgtgat catgttcaac aaccagacaa    780
caatcctctg ttgattttttc cggaaggaac ttgtgtgaac aaccagtaca cggtcatgtt    840
caagaagggt gcctttgagc ttggctgcgc tgtatgtcca atagctatca agtacaataa    900
aatatttgtt gatgcctttt ggaacagtaa gaagcaatct tttacaatgc acttggtccg    960
gctgatgaca tcatgggctg ttgtgtgtga tgtttggtac ttacctcctc aatatctgag   1020
ggagggagag acggcaattg catttgctga gagagtaagg gacatgatag ctgctagagc   1080
tggactaaag aaggttcctt gggatggcta tctgaaacac aaccgtccta gtcccaaaca   1140
cactgaagag aaacaacgca tatttgccga atctgtcttg atgagactgg aggagaaatg   1200
aagggacgta agccgtaca agtgcacttc gttagggttt tacatgcagc taccttgtaa   1260
ttcggttggc ttccagaaaa aaaaaagtga gcctgggaca cgtcaagtga ccacctcagt   1320
tttgttgtaa atttgttact agtttgatag gattattagt atgtacttat caggaaaaga   1380
attctcagta tgtgttttgg ctgcccattc aatgataggt cagtgattaa caccgaagca   1440
ttgtgctctc gtgagatgct gtgttggtct taatatattg acggtactgt accatggttt   1500
aaatgtgatt attgaagcaa tgtgaatgga ttagctggct aagaaaaaaa aaaaaaaaa   1560 aaaaaaaaaa aaaaaaaaaa ag                                            1582
```

<210> SEQ ID NO 28
<211> LENGTH: 371
<212> TYPE: PRT
<213> ORGANISM: Zea mays

<400> SEQUENCE: 28

```
Met Ala Thr Ser Ser Val Ala Ala Asp Met Glu Leu Asp Arg Pro Asn
 1               5                  10                  15

Leu Glu Asp Tyr Leu Pro Pro Asp Ser Leu Pro Gln Glu Ala Pro Arg
             20                  25                  30

Asn Leu His Leu Arg Asp Leu Leu Asp Ile Ser Pro Val Leu Thr Glu
         35                  40                  45

Ala Ala Gly Ala Ile Val Asp Asp Ser Phe Thr Arg Cys Phe Lys Ser
     50                  55                  60

Asn Ser Pro Glu Pro Trp Asn Trp Asn Ile Tyr Leu Phe Pro Leu Trp
 65                  70                  75                  80

Cys Phe Gly Val Val Ile Arg Tyr Gly Leu Leu Phe Pro Leu Arg Ser
                 85                  90                  95

Leu Thr Leu Ala Ile Gly Trp Leu Ala Phe Phe Ala Ala Phe Phe Pro
            100                 105                 110
```

```
Val His Phe Leu Leu Lys Gly Gln Asp Lys Leu Arg Ser Lys Ile Glu
        115                 120                 125

Arg Lys Leu Val Glu Met Met Cys Ser Val Phe Val Ala Ser Trp Thr
    130                 135                 140

Gly Val Ile Lys Tyr His Gly Pro Arg Pro Ser Thr Arg Pro His Gln
145                 150                 155                 160

Val Phe Val Ala Asn His Thr Ser Met Ile Asp Phe Ile Ile Leu Glu
                165                 170                 175

Gln Met Thr Ala Phe Ala Val Ile Met Gln Lys His Pro Gly Trp Val
            180                 185                 190

Gly Phe Ile Gln Lys Thr Ile Leu Glu Ser Val Gly Cys Ile Trp Phe
        195                 200                 205

Asn Arg Asn Asp Leu Arg Asp Arg Glu Val Thr Ala Arg Lys Leu Arg
    210                 215                 220

Asp His Val Gln Gln Pro Asp Asn Asn Pro Leu Leu Ile Phe Pro Glu
225                 230                 235                 240

Gly Thr Cys Val Asn Asn Gln Tyr Thr Val Met Phe Lys Lys Gly Ala
                245                 250                 255

Phe Glu Leu Gly Cys Ala Val Cys Pro Ile Ala Ile Lys Tyr Asn Lys
            260                 265                 270

Ile Phe Val Asp Ala Phe Trp Asn Ser Lys Lys Gln Ser Phe Thr Met
        275                 280                 285

His Leu Val Arg Leu Met Thr Ser Trp Ala Val Val Cys Asp Val Trp
    290                 295                 300

Tyr Leu Pro Pro Gln Tyr Leu Arg Glu Gly Glu Thr Ala Ile Ala Phe
305                 310                 315                 320

Ala Glu Arg Val Arg Asp Met Ile Ala Ala Arg Ala Gly Leu Lys Lys
                325                 330                 335

Val Pro Trp Asp Gly Tyr Leu Lys His Asn Arg Pro Ser Pro Lys His
            340                 345                 350

Thr Glu Glu Lys Gln Arg Ile Phe Ala Glu Ser Val Leu Met Arg Leu
        355                 360                 365

Glu Glu Lys
    370

<210> SEQ ID NO 29
<211> LENGTH: 1422
<212> TYPE: DNA
<213> ORGANISM: Oryza sativa

<400> SEQUENCE: 29
gcacgagatc actgcgaaga tttcctcggc ggcggcggag gggatcgacg gaggggggga      60
tggcgacctc gtcggtggcg ggggacatcg agctggaccg gccgaacctg gaggactacc     120
tcccatccga ctcgctgccg caggagttcc ccaggaatct ccatctgcgc gatctgctgg     180
acatctcgcc ggtgctcact gaagcagcgg gcgccatcgt cgatgattca ttcacacgtt     240
gctttaagtc aaattctcca gagccatgga attggaacat ttatttattc ccattgtggt     300
gcttgggagt agtgataaga tacggaatac tattcccgct gagggggccta actcttctag     360 ttggatggtt agcattcttt gctgcctttt tcctgtaca tttcttattg aaaggtcaaa       420
agatgagaag taaaatagag agaaagctgg ttgaaatgat gtgcagtgtt tttgttgctt      480
cttggactgg agtgatcaag tatcatgggc ctcgcccaag cacacggcct catcaggtat      540
ttgttgcaaa ccatacatcg atgatagatt tcattattct ggagcagatg acagcatttg      600
```

-continued

```
ctgtcattat gcaaaagcat cctggatggg ttggatttat tcagaagact atcttggaaa     660
gtgttggttg catctggttt aatcgcaatg atctcaagga tcgtgaagtg gttgcaaaaa     720
agttacgaga tcatgttcaa catccagaca gcaatcctct cctgattttc cctgaaggaa     780
cttgtgttaa caaccagtac actgtcatgt tcaagaaggg tgcttttgag cttggctgtg     840
ctgtatgccc aatagctatc aaatacaata aatatttgt tgatgccttc tggaatagta      900
agaagcaatc gtttacaatg cacttggtta ggcttatgac atcatgggca gttgtgtgtg     960
atgtatggta cttggagcct cagtatctga gggatggaga acagcaatt gaatttgctg     1020 aaagagtaag agacatgata gctgctagag ctggtcttaa gaaggttccg tgggacgggt    1080
atctgaaaca caaccgccct agtcccaaac acactgaaga gaagcagcgc atctttgctg    1140
actctgtgtt gcggagactg gaggaaagct aaacagatat caatcaactc tggtgctcat    1200
tggtgagtcc aggttactaa tgtcctagtg tgtatctggg tctctggagt atgtggaaat    1260
taccactgca gttttgttgt aaattgtttg cagcttgaca gaatcaacat ttaatagcct    1320
gtattagcca agattttatg attggttagg gttaacacat aaatattata ccttcccaaa    1380
tgatgtatta atacttaccc tcaaaaaaaa aaaaaaaaa ac                         1422
```

<210> SEQ ID NO 30
<211> LENGTH: 370
<212> TYPE: PRT
<213> ORGANISM: Oryza sativa

<400> SEQUENCE: 30

```
Met Ala Thr Ser Ser Val Ala Gly Asp Ile Glu Leu Asp Arg Pro Asn
  1               5                  10                  15

Leu Glu Asp Tyr Leu Pro Ser Asp Ser Leu Pro Gln Glu Phe Pro Arg
             20                  25                  30

Asn Leu His Leu Arg Asp Leu Leu Asp Ile Ser Pro Val Leu Thr Glu
         35                  40                  45

Ala Ala Gly Ala Ile Val Asp Asp Ser Phe Thr Arg Cys Phe Lys Ser
     50                  55                  60

Asn Ser Pro Glu Pro Trp Asn Trp Asn Ile Tyr Leu Phe Pro Leu Trp
 65                  70                  75                  80

Cys Leu Gly Val Val Ile Arg Tyr Gly Ile Leu Phe Pro Leu Arg Gly
                 85                  90                  95

Leu Thr Leu Leu Val Gly Trp Leu Ala Phe Phe Ala Ala Phe Phe Pro
            100                 105                 110

Val His Phe Leu Leu Lys Gly Gln Lys Met Arg Ser Lys Ile Glu Arg
        115                 120                 125

Lys Leu Val Glu Met Met Cys Ser Val Phe Val Ala Ser Trp Thr Gly
    130                 135                 140

Val Ile Lys Tyr His Gly Pro Arg Pro Ser Thr Arg Pro His Gln Val
145                 150                 155                 160

Phe Val Ala Asn His Thr Ser Met Ile Asp Phe Ile Ile Leu Glu Gln
                165                 170                 175

Met Thr Ala Phe Ala Val Ile Met Gln Lys His Pro Gly Trp Val Gly
            180                 185                 190

Phe Ile Gln Lys Thr Ile Leu Glu Ser Val Gly Cys Ile Trp Phe Asn
        195                 200                 205

Arg Asn Asp Leu Lys Asp Arg Glu Val Val Ala Lys Lys Leu Arg Asp
    210                 215                 220

His Val Gln His Pro Asp Ser Asn Pro Leu Leu Ile Phe Pro Glu Gly
```

```
                225                 230                 235                 240
Thr Cys Val Asn Asn Gln Tyr Thr Val Met Phe Lys Lys Gly Ala Phe
                    245                 250                 255
Glu Leu Gly Cys Ala Val Cys Pro Ile Ala Ile Lys Tyr Asn Lys Ile
                260                 265                 270
Phe Val Asp Ala Phe Trp Asn Ser Lys Lys Gln Ser Phe Thr Met His
            275                 280                 285
Leu Val Arg Leu Met Thr Ser Trp Ala Val Val Cys Asp Val Trp Tyr
        290                 295                 300
Leu Glu Pro Gln Tyr Leu Arg Asp Gly Glu Thr Ala Ile Glu Phe Ala
305                 310                 315                 320
Glu Arg Val Arg Asp Met Ile Ala Ala Arg Ala Gly Leu Lys Lys Val
                    325                 330                 335
Pro Trp Asp Gly Tyr Leu Lys His Asn Arg Pro Ser Pro Lys His Thr
                340                 345                 350
Glu Glu Lys Gln Arg Ile Phe Ala Asp Ser Val Leu Arg Arg Leu Glu
            355                 360                 365
Glu Ser
    370

<210> SEQ ID NO 31
<211> LENGTH: 1392
<212> TYPE: DNA
<213> ORGANISM: Sorghum

<400> SEQUENCE: 31
gcacgagcca ggaatctcca tctgcgcgat ctgcttgaca tctcgccggt gctaaccgag       60
gcagcgggtg ccatagtcga tgattcattc acgcgctgct taagtcgaa ttctccagaa      120
ccatggaact ggaacatata tttgttccct ttatggtgct tcggtgtagt aattcgatat      180
ggattactct tcccactgag gtccttaacg cttgcaatag gatggttagc attttttgct      240
gccttttttcc ccgtgcattt cctattgaaa ggtcaagaca gttgagaaa taaaattgag      300
aggaagttgg ttgaaatgat gtgcagtgtt tttgttgctt catggactgg agtgatcaag      360
taccatggac cacgcccaag cacacgacct catcaggtat tgttgcaaa ccatacatca      420
atgatagatt tcattattct ggagcaaatg acagcatttg ctgtcatcat gcagaagcat      480
cctggatggg ttgatttat tcagaagact atcttggaaa gtgtgggttg catctggttt      540
aaccgtaatg atctccggga tcgtgaagtt acggcacgga agttgcgtga tcatgttcaa      600
catccagaca aaaaccctct cttgattttc ccagaaggaa cttgtgttaa caaccagtat      660
acggtcatgt tcaagaaggg tgcctttgag cttgggtgtg ctgtctgtcc aatagctatc      720
aaatacaata aatatttgt tgatgccttt tggaacagta agaagcaatc ttttacgatg      780
cacttggtcc ggttgatgac atcatgggct gttgtgtgtg atgtttggta cttggagcct      840
caatatctga gggagggaga gactgcaatt gcgtttgctg agagagtaag ggacatgata      900
gcagctagag ctggtcttaa gaaggtcccg tgggatggct atctgaaaca caaccgccct      960
agtcccaaac acaccgaaga gaagcaacgc atattcgccg aatctgtctt gaggagacta     1020
gaggagaaat gaagagacat caaacactac aagcgcattt ggttagtggt ttaccgttca     1080
gctaccttgt aattcggttg gctccccgaa aaaaaaagt ccgggacacg tcaagtgccc     1140
agctcagttt tgttgtaaat ttattagaaa tttgacagaa ttggtagtgt gaacttacca     1200
agaaaggaag aatagccgca tgtgttgtgg ctgttcattc tatgattggt taggaattga     1260
```

```
cacttgaaac acggtactct attcagaggc tgtgtccgta tttatgaatc gacgatgtaa    1320
tggttttaat tcatgtgatt attgattcaa taatatgagt agattaaaaa aaaaaaaaaa    1380
aaaaaaaaaa aa                                                        1392
```

<210> SEQ ID NO 32
<211> LENGTH: 343
<212> TYPE: PRT
<213> ORGANISM: Sorghum

<400> SEQUENCE: 32

```
Ala Arg Ala Arg Asn Leu His Leu Arg Asp Leu Leu Asp Ile Ser Pro
  1               5                  10                  15

Val Leu Thr Glu Ala Ala Gly Ala Ile Val Asp Asp Ser Phe Thr Arg
             20                  25                  30

Cys Phe Lys Ser Asn Ser Pro Glu Pro Trp Asn Trp Asn Ile Tyr Leu
         35                  40                  45

Phe Pro Leu Trp Cys Phe Gly Val Val Ile Arg Tyr Gly Leu Leu Phe
     50                  55                  60

Pro Leu Arg Ser Leu Thr Leu Ala Ile Gly Trp Leu Ala Phe Phe Ala
 65                  70                  75                  80

Ala Phe Phe Pro Val His Phe Leu Leu Lys Gly Gln Asp Lys Leu Arg
                 85                  90                  95

Asn Lys Ile Glu Arg Lys Leu Val Glu Met Met Cys Ser Val Phe Val
            100                 105                 110

Ala Ser Trp Thr Gly Val Ile Lys Tyr His Gly Pro Arg Pro Ser Thr
        115                 120                 125

Arg Pro His Gln Val Phe Val Ala Asn His Thr Ser Met Ile Asp Phe
    130                 135                 140

Ile Ile Leu Glu Gln Met Thr Ala Phe Ala Val Ile Met Gln Lys His
145                 150                 155                 160

Pro Gly Trp Val Gly Phe Ile Gln Lys Thr Ile Leu Glu Ser Val Gly
                165                 170                 175

Cys Ile Trp Phe Asn Arg Asn Asp Leu Arg Asp Arg Glu Val Thr Ala
            180                 185                 190

Arg Lys Leu Arg Asp His Val Gln His Pro Asp Lys Asn Pro Leu Leu
        195                 200                 205

Ile Phe Pro Glu Gly Thr Cys Val Asn Asn Gln Tyr Thr Val Met Phe
    210                 215                 220

Lys Lys Gly Ala Phe Glu Leu Gly Cys Ala Val Cys Pro Ile Ala Ile
225                 230                 235                 240

Lys Tyr Asn Lys Ile Phe Val Asp Ala Phe Trp Asn Ser Lys Lys Gln
                245                 250                 255

Ser Phe Thr Met His Leu Val Arg Leu Met Thr Ser Trp Ala Val Val
            260                 265                 270

Cys Asp Val Trp Tyr Leu Glu Pro Gln Tyr Leu Arg Glu Gly Glu Thr
        275                 280                 285

Ala Ile Ala Phe Ala Glu Arg Val Arg Asp Met Ile Ala Ala Arg Ala
    290                 295                 300

Gly Leu Lys Lys Val Pro Trp Asp Gly Tyr Leu Lys His Asn Arg Pro
305                 310                 315                 320

Ser Pro Lys His Thr Glu Glu Lys Gln Arg Ile Phe Ala Glu Ser Val
                325                 330                 335

Leu Arg Arg Leu Glu Glu Lys
        340
```

<210> SEQ ID NO 33
<211> LENGTH: 1466
<212> TYPE: DNA
<213> ORGANISM: Glycine max

<400> SEQUENCE: 33

```
tctctctctc tctctctctc tctctctctc tctctctctg acaaaattg ccctccatca      60
ctttccttgt tagagttggt ttctgcaacc taccatgcaa ttcctcacct gaatccgttt    120
tctattgcca cgttgggatc gaaaagtcta gtttaaccac acgtttgtgg ttgtagtgga    180
agcgtaacga agatgaatgg cattgggaaa ctcaaatcgt cgagttctga attggacctt    240
cacattgaag attacctacc ttctggatcc agtgttcaac aagaacggca tggcaagctc    300
cgactgtgtg atttgctaga catttctcct agtctatctg aggcagcacg tgccattgta    360
gatgatacat tcacaaggtg cttcaagtca aatcctccag aaccttggaa ctggaatgtt    420
tatttgtttc ctttgtggtg ctgtggagtt gtggttcgat atttgatttt gttccctatt    480
aggattctag tgttggcatt aggatggatt atatttcttt cagccttcat tccagtgcac    540
tccctcctga aggaaatga tgatttgagg aaaaagattg agaggtgttt ggtggagatg    600
atgtgcagtt tctttgttgc atcatggact ggggttgtca agtaccatgg gccaagacct    660
agtatccgac caaaacaggt ttttgtggcc aatcatactt ccatgattga tttcattatc    720
ttagaacaga tgactgcatt tgctgttatt atgcagaagc atcctggatg ggttggatta    780
ttgcagagca ccattttgga gagtgtgggg tgtatctggt tcaatcgtac agaggcaaag    840
gatcgagaaa ttgtggcaag gaaattgagg gatcatgtcc tgggagctaa caataaccct    900
cttctcatat ttcctgaagg aacttgtgta ataatcact actctgtcat gttcaagaag    960
ggtgcatttg aacttggctg cacaatttgc ccagttgcaa tcaagtacaa taaaattttc   1020
gtcgatgctt tttggaatag tcgaaagcaa tcattcacca ctcatctctt gcaattaatg   1080
acatcttggg ctgtagtttg tgatgtttgg tacttggagc cacaaaattt gaagccagga   1140
gagacaccca ttgaatttgc agagagagtt agagacataa tctcacatcg tgctgggctt   1200
aaaaaggttc cttgggatgg atatctgaag tattctcgcc ctagtcccaa gcacagagaa   1260
ggaaagcaac aaatattcgc tgagtctgtg ttgcggcgct ttgaggaaaa ataatgtata   1320
tcttttttact ttttcagtaa tgattttctc caaccttgt ttgtactcca cttactacta   1380
tgatatacat gtagatctta catgaaattg cctgaaaatt ttccatgacc aaaaaaaaaa   1440
aaaaaaaact cgagactagt tctctc                                         1466
```

<210> SEQ ID NO 34
<211> LENGTH: 373
<212> TYPE: PRT
<213> ORGANISM: Glycine max

<400> SEQUENCE: 34

```
Met Asn Gly Ile Gly Lys Leu Lys Ser Ser Ser Glu Leu Asp Leu
  1               5                  10                  15

His Ile Glu Asp Tyr Leu Pro Ser Gly Ser Ser Val Gln Gln Glu Arg
                 20                  25                  30

His Gly Lys Leu Arg Leu Cys Asp Leu Leu Asp Ile Ser Pro Ser Leu
             35                  40                  45

Ser Glu Ala Ala Arg Ala Ile Val Asp Asp Thr Phe Thr Arg Cys Phe
         50                  55                  60
```

```
Lys Ser Asn Pro Pro Glu Pro Trp Asn Trp Asn Val Tyr Leu Phe Pro
 65                  70                  75                  80

Leu Trp Cys Cys Gly Val Val Arg Tyr Leu Ile Leu Phe Pro Ile
             85                  90                  95

Arg Ile Leu Val Leu Ala Leu Gly Trp Ile Ile Phe Leu Ser Ala Phe
            100                 105                 110

Ile Pro Val His Ser Leu Leu Lys Gly Asn Asp Asp Leu Arg Lys Lys
            115                 120                 125

Ile Glu Arg Cys Leu Val Glu Met Met Cys Ser Phe Val Ala Ser
130                 135                 140

Trp Thr Gly Val Val Lys Tyr His Gly Pro Arg Pro Ser Ile Arg Pro
145                 150                 155                 160

Lys Gln Val Phe Val Ala Asn His Thr Ser Met Ile Asp Phe Ile Ile
                165                 170                 175

Leu Glu Gln Met Thr Ala Phe Ala Val Ile Met Gln Lys His Pro Gly
            180                 185                 190

Trp Val Gly Leu Leu Gln Ser Thr Ile Leu Glu Ser Val Gly Cys Ile
            195                 200                 205

Trp Phe Asn Arg Thr Glu Ala Lys Asp Arg Glu Ile Val Ala Arg Lys
            210                 215                 220

Leu Arg Asp His Val Leu Gly Ala Asn Asn Pro Leu Leu Ile Phe
225                 230                 235                 240

Pro Glu Gly Thr Cys Val Asn Asn His Tyr Ser Val Met Phe Lys Lys
                245                 250                 255

Gly Ala Phe Glu Leu Gly Cys Thr Ile Cys Pro Val Ala Ile Lys Tyr
            260                 265                 270

Asn Lys Ile Phe Val Asp Ala Phe Trp Asn Ser Arg Lys Gln Ser Phe
            275                 280                 285

Thr Thr His Leu Leu Gln Leu Met Thr Ser Trp Ala Val Val Cys Asp
            290                 295                 300

Val Trp Tyr Leu Glu Pro Gln Asn Leu Lys Pro Gly Glu Thr Pro Ile
305                 310                 315                 320

Glu Phe Ala Glu Arg Val Arg Asp Ile Ile Ser His Arg Ala Gly Leu
                325                 330                 335

Lys Lys Val Pro Trp Asp Gly Tyr Leu Lys Tyr Ser Arg Pro Ser Pro
            340                 345                 350

Lys His Arg Glu Gly Lys Gln Gln Ile Phe Ala Glu Ser Val Leu Arg
            355                 360                 365

Arg Phe Glu Glu Lys
    370

<210> SEQ ID NO 35
<211> LENGTH: 1384
<212> TYPE: DNA
<213> ORGANISM: Catalpa speciosa

<400> SEQUENCE: 35
gcacgaggta ggtttctgtc gaggattttg ttgtttgttt tcgggttcta ttggattggt      60
gaaaccagta agggaattga ggttgatggg caggggaata atgagtctgc atctaggaat     120
cggtctgaag aggtggaagg acctgggggct attgtatcca atcatatatc ttatatagat    180
atcctgtatc acatgtcttc ctctttccca gtttcgtttt ccaagagatc cgtcgctaaa     240
cttccccttg ttggtcttgt gagcaagtgt cttggttgtg tatatgtaca gcgtgagtta     300
aagtcgtcgg atttcaaggg ggtatcaggt gttgtcactg aaagaattca agaagctcat    360
```

```
caaataagt tgctccaaa gatgataatt tcccagaag gcacaactac aaatgggac      420 ttcctccttc cattcaagac tggtgcattt ttggcaaagg ctccagtact tcctgtcatt    480
ttaagatatt cgtaccagag atttagtccc gcgtgggact ctatttctgg ggctcgccat    540
gtgattcttc ttctctgtca gtttgtaaat tacattgaag tgacacattt gcctgtttat    600
catccgtccg aacaagaaaa ggaagatccc aagcttttcg ctgaaaatgt taggcttctg    660
atggctcgtg agggtaattt gattctttcg gatattggat tggcggagaa acgagtttat    720
catgctgctc tcaatggttt actttgtcaa agataatcca gcttcgctat attgattgta    780
taaatgtatt ttttgacttc cataaaacta ataactaagc ccataaatta cgctggaaga    840
ggtcattgat cttcatcgtc tatacgattt ctaactatta tctggacatc ttagttactg    900
cttcagcttt ggtaaggatc tctaaagct gtctctattt gatacattag gccgtctggc     960
ttaatacaga acgtggaagc cgatgttgta ttaacgacgt tggtgaacat ggagctattg   1020
cttctacttg aaatttgacc atccattatt tgattcttga cacatgaagt tgagaaatta   1080
gagttcgttt gagattagcc ataaatcgca tttctctaac agtttgttct actgggtacg   1140
gtattagttt ccccttgtat atagcacaat gcaaatgctg tagttaacta ctttgttttg   1200
atcttctgtt ttgtttgctt tattgcaacg ttaggagttg taaatatcct taaaatctag   1260
ttggattagc atagttaatt gtgaaatatg tagtggtgcc tgagaatggt cttggattgg   1320
aagtcttgct tcttctggga aaaaaaaaa aaaaaaaaaa aaaaaaaaaa aaaaaaaaaa   1380
aaaa                                                                 1384

<210> SEQ ID NO 36
<211> LENGTH: 251
<212> TYPE: PRT
<213> ORGANISM: Catalpa speciosa

<400> SEQUENCE: 36

Ala Arg Gly Arg Phe Leu Ser Arg Ile Leu Leu Phe Val Phe Gly Phe
 1               5                  10                  15

Tyr Trp Ile Gly Glu Thr Ser Lys Gly Ile Glu Val Asp Gly Gln Gly
            20                  25                  30

Asn Asn Glu Ser Ala Ser Arg Asn Arg Ser Glu Glu Val Glu Gly Pro
        35                  40                  45

Gly Ala Ile Val Ser Asn His Ile Ser Tyr Ile Asp Ile Leu Tyr His
    50                  55                  60

Met Ser Ser Ser Phe Pro Ser Phe Val Ser Lys Arg Ser Val Ala Lys
65                  70                  75                  80

Leu Pro Leu Val Gly Leu Val Ser Lys Cys Leu Gly Cys Val Tyr Val
                85                  90                  95

Gln Arg Glu Leu Lys Ser Ser Asp Phe Lys Gly Val Ser Gly Val Val
            100                 105                 110

Thr Glu Arg Ile Gln Glu Ala His Gln Asn Lys Phe Ala Pro Lys Met
        115                 120                 125

Ile Ile Phe Pro Glu Gly Thr Thr Thr Asn Gly Asp Phe Leu Leu Pro
    130                 135                 140

Phe Lys Thr Gly Ala Phe Leu Ala Lys Ala Pro Val Leu Pro Val Ile
145                 150                 155                 160

Leu Arg Tyr Ser Tyr Gln Arg Phe Ser Pro Ala Trp Asp Ser Ile Ser
                165                 170                 175

Gly Ala Arg His Val Ile Leu Leu Leu Cys Gln Phe Val Asn Tyr Ile
```

```
                180              185               190
Glu Val Thr His Leu Pro Val Tyr His Pro Ser Glu Gln Glu Lys Glu
          195                 200                 205
Asp Pro Lys Leu Phe Ala Glu Asn Val Arg Leu Leu Met Ala Arg Glu
      210                 215                 220
Gly Asn Leu Ile Leu Ser Asp Ile Gly Leu Ala Glu Lys Arg Val Tyr
225                 230                 235                 240
His Ala Ala Leu Asn Gly Leu Leu Cys Gln Arg
              245                 250
```

<210> SEQ ID NO 37
<211> LENGTH: 1042
<212> TYPE: DNA
<213> ORGANISM: Triticum aestivum

<400> SEQUENCE: 37

```
gcacgagcag gggttgagga gggaggccgt gctgcgtgct ggccgcgtgt tgtcgcgggc        60
aatgctgttc gtgttcgggt tctactggat ccccgtgtcc gatcgaagct tccccaatgc       120
cgaggatgta cctaaagatc actatgaaga actggaaaga ccaggggcga ttgtatctaa       180
tcatgtgtca tatgtggaca ttctttatca tatgtcagct tcttctccga gttttgttgc       240
taagaactca gtgtccaagt tgccgttgat tggtctcata agcaaatgtc ttgggtgcat       300
ttttgttcaa cgagaatcca atgttcaga ttctaaaggt gtctcaggtg ctgtaactga       360
aaggctccat gaggtttcac aagacgagaa ttccccctatg atcttactct ttcctgaggg       420
tactactacg aatggggatt accttctccc atttaagaca ggagcctttc ttgcaagggc       480
accattgcaa cctgtaattt tgagatatcc ttacaggaga tttagtccag cctgggactc       540
catggatggg gcacgtcatg tgttttgct cctctgtcaa tttgcaaatt acatagaggt       600
ggttcgcttg cctgtatact atccttctga gcaagaaaag caggatccta gagtctatgc       660
caacaacgtc agaaaattgc ttgcgactga gggtaattta gttctgtcta atcttgggct       720
ggctgaaaag cgtgtgtatc atgcggcact taatggtaat agtcctcgtg ctctgcatca       780
gaaagatgat tgaaagccct tgcatcactc tctgtacact atctgttgag gtgattgtaa       840
gaatgtatgc caactttagc tgatcatgtg attcatggtt tctctgttg aggagtatgt       900
tgattgatga aacattata cctatttga gatgaattcc ctccttatac tacattgtat       960
agaaaccatt aaacattata gttcaataat aatgtctggc ataattgttt tgcttgttca      1020
aaaaaaaaaa aaaaaaaaaa aa                                              1042
```

<210> SEQ ID NO 38
<211> LENGTH: 261
<212> TYPE: PRT
<213> ORGANISM: Triticum aestivum

<400> SEQUENCE: 38

```
Gln Gly Leu Arg Arg Glu Ala Val Leu Arg Ala Gly Arg Val Leu Ser
  1               5                  10                  15
Arg Ala Met Leu Phe Val Phe Gly Phe Tyr Trp Ile Pro Val Ser Asp
              20                  25                  30
Arg Ser Phe Pro Asn Ala Glu Asp Val Pro Lys Asp His Tyr Glu Glu
          35                  40                  45
Leu Glu Arg Pro Gly Ala Ile Val Ser Asn His Val Ser Tyr Val Asp
      50                  55                  60
Ile Leu Tyr His Met Ser Ala Ser Ser Pro Ser Phe Val Ala Lys Asn
```

```
                65                  70                  75                  80
Ser Val Ser Lys Leu Pro Leu Ile Gly Leu Ile Ser Lys Cys Leu Gly
                    85                  90                  95

Cys Ile Phe Val Gln Arg Glu Ser Lys Cys Ser Asp Ser Lys Gly Val
               100                 105                 110

Ser Gly Ala Val Thr Glu Arg Leu His Glu Val Ser Gln Asp Glu Asn
           115                 120                 125

Ser Pro Met Ile Leu Leu Phe Pro Glu Gly Thr Thr Thr Asn Gly Asp
       130                 135                 140

Tyr Leu Leu Pro Phe Lys Thr Gly Ala Phe Leu Ala Arg Ala Pro Leu
145                 150                 155                 160

Gln Pro Val Ile Leu Arg Tyr Pro Tyr Arg Arg Phe Ser Pro Ala Trp
                165                 170                 175

Asp Ser Met Asp Gly Ala Arg His Val Phe Leu Leu Cys Gln Phe
            180                 185                 190

Ala Asn Tyr Ile Glu Val Val Arg Leu Pro Val Tyr Tyr Pro Ser Glu
            195                 200                 205

Gln Glu Lys Gln Asp Pro Arg Val Tyr Ala Asn Asn Val Arg Lys Leu
        210                 215                 220

Leu Ala Thr Glu Gly Asn Leu Val Leu Ser Asn Leu Gly Leu Ala Glu
225                 230                 235                 240

Lys Arg Val Tyr His Ala Ala Leu Asn Gly Asn Ser Pro Arg Ala Leu
                245                 250                 255

His Gln Lys Asp Asp
            260

<210> SEQ ID NO 39
<211> LENGTH: 1459
<212> TYPE: DNA
<213> ORGANISM: Zea mays
<220> FEATURE:
<221> NAME/KEY: unsure
<222> LOCATION: (203)
<223> OTHER INFORMATION: n = a, c, g, or t

<400> SEQUENCE: 39
gtttccaatc atatctcgta catagaaccc atattcttct tctatgaatt gttcccaacc      60
attgtttcgt cagagtctca tgatgcccta ccatttgttg aacaattat tcgagcgatg     120 caggttatat atgttgacag attctcacca gcttctcgga aggctgctgt aaatgaaata     180
aagagaaagg cagcttgcaa tancttcccg cgggtcctgt tattccctga aggcaccaca     240
acaaatggga gattcctgat ttcgttccaa catggtgcgt tcatacctgg ctaccctgtt     300
caacctgttt ttgtccatta tccacatgtg cactttgatc aatcatgggg aaatatatcg     360
ttattaaagc tcatgttcaa gatgttcaca cagtttcata atttcatgga ggtagagtac     420
cttcctgttg tctaccctcc tgagatcaag caagagaatg cccttcattt tgcagaggat     480
accagctatg ctatggcacg tgccctgaat gccttgccga cttattattc atggcgattc     540
tatgattatg gcacgagcag tagaagctgg aaaggtgaac tgctcaaatt atatggtaga     600
aatggcttgg gttaaagatg tttacggtat aagcacagca gaagtgatgg aactattgga     660
acatttcctg gctatgaatc cagataacga tggacgtgtg aaagctgaag atttctgggc     720
tcattttggt ctggattgca gtcctctgtg caagaagata tttcactatt tcgatttaga     780
cattaagggg ttgattacgt tccgtcagtt cttggttggg tgcgcgcacc tgaggaagca     840
accactgttc cagggttcct gcgagaccgc ctttgagaag tgccggggtc ctgaaacgtc     900
```

-continued

```
tgagatctcc agggcacagc tagctgatct cttgcggtta agcatggtgc caccttctga    960
tgataagatg ctggagctgt tcaagacgtt cgatgtagat ggcgacgaga agatcagcag   1020
ggacgacttc atggcgtgtc ttgggaggtt cccgttcctg atcgcgttct ttgctgccct   1080
gatcaatggg gaagtgtaca tcgagatagt ctgaatgaat gcctgaggca aagcgatgcc   1140
gcgtaaaagg ctggagctgc cagtgccagg cgtaggcagg ggatccctcc gtttatgcaa   1200
tgtggatacc caccgggtgc tcctccactt tgagaccaaa gcaactgtag tattgggtat   1260
tgggttgcat caagtggctg accagtgtag tgcgtcgatt ttgtttagtt gcttcgttcg   1320
aattattatt ggccatttac cgaatctgtt gagatacgcg ctggactagt agattgtcga   1380
tggaactcag aacgcaaata gaaagcatct gtaatctgaa ctaactgaga aaacatttaa   1440
aaaaaaaaaa aaaaaaaa                                                 1459
```

<210> SEQ ID NO 40
<211> LENGTH: 204
<212> TYPE: PRT
<213> ORGANISM: Zea mays
<220> FEATURE:
<221> NAME/KEY: UNSURE
<222> LOCATION: (68)
<223> OTHER INFORMATION: Xaa = any amino acid

<400> SEQUENCE: 40

```
Val Ser Asn His Ile Ser Tyr Ile Glu Pro Ile Phe Phe Tyr Glu
 1               5                  10                  15

Leu Phe Pro Thr Ile Val Ser Ser Glu Ser His Asp Ala Leu Pro Phe
             20                  25                  30

Val Gly Thr Ile Ile Arg Ala Met Gln Val Ile Tyr Val Asp Arg Phe
         35                  40                  45

Ser Pro Ala Ser Arg Lys Ala Ala Val Asn Glu Ile Lys Arg Lys Ala
     50                  55                  60

Ala Cys Asn Xaa Phe Pro Arg Val Leu Leu Phe Pro Glu Gly Thr Thr
 65                  70                  75                  80

Thr Asn Gly Arg Phe Leu Ile Ser Phe Gln His Gly Ala Phe Ile Pro
                 85                  90                  95

Gly Tyr Pro Val Gln Pro Val Val His Tyr Pro His Val His Phe
            100                 105                 110

Asp Gln Ser Trp Gly Asn Ile Ser Leu Leu Lys Leu Met Phe Lys Met
        115                 120                 125

Phe Thr Gln Phe His Asn Phe Met Glu Val Glu Tyr Leu Pro Val Val
    130                 135                 140

Tyr Pro Pro Glu Ile Lys Gln Glu Asn Ala Leu His Phe Ala Glu Asp
145                 150                 155                 160

Thr Ser Tyr Ala Met Ala Arg Ala Leu Asn Ala Leu Pro Thr Tyr Tyr
                165                 170                 175

Ser Trp Arg Phe Tyr Asp Tyr Gly Thr Ser Ser Arg Ser Trp Lys Gly
            180                 185                 190

Glu Leu Leu Lys Leu Tyr Gly Arg Asn Gly Leu Gly
        195                 200
```

<210> SEQ ID NO 41
<211> LENGTH: 2115
<212> TYPE: DNA
<213> ORGANISM: Oryza sativa

<400> SEQUENCE: 41

```
gcacgaggtt ctaacccgcc tcctctcgcc tcgcctccgc cacccatggc ttctcgaaac      60
cctagccccg cctccctctc cacgccgctc ctctccgact ccatctcgcc cacgcccacc     120
accaacggcc acgcggggca ccataaccac gacgacgacg acgaggagtc gccaacggtg     180
tgcggcggcg atggcggagg aggggggggac ccgttcgcgt tcctatcgga ggatcggccg     240
gcgtggtggt cgccgcgggg ggtgtccccg gccgacccgt tccgcaacgg gacgccgggg     300
tggtgcgggg cgtacgagct cgtgagggcg ctcgtgtgcg cgccggtggc ggcggcgagg     360
ctggtgctgt tcgggctctc catcgcgtg gggtacgccg ccacgtgggt ggcgctccgc     420
gggtgggtcg acgtgcggga gcggcggcg caggagggcg ccgggcccat gccggcgtgg     480
cgccgccgcc tcatgtggat cacgcggatc tccgcgcgct gcatcctctt ctccttcgga     540
taccattgga taaggaggaa aggaaaaccc gcgcctagag agcttgcacc tatagttgtc     600
tcaaatcatg tatcatacat agaacccata tacttcttct atgagctgtt cccgacaatc     660
gtttcttcag attctcatga ttccatacca tttgttggaa caattatccg agcaatgcag     720
gttatatatg ttgacagatt ctcgccagct tcaaggaagt ctgctgtaaa tgaaataaag     780
gatgtgattt cagagaaagg cggcttgcaa tagcttccca cgtgtcttgt tattcccgga     840
aggcacgaca acaaatggaa gatttctgat ttctttccaa catggtgcat tcatacctgg     900
ctaccctgtt caacctgtta ttgtgcgcta tccacatgtg cactttgatc aatcatgggg     960
aaatatatca ttaggaaagc tcatgttcaa gatgtttacc cagtttcaca atttcatgga    1020
ggtagagtac ctccctgttg tttacccacc tgagatcaag caagagaatg cccttcattt    1080
tgcagagaac actagctatg ctatggcaca tgcacttaat gttattccaa cctcttattc    1140
atatggggat tcaatgatca tggctcgagc agtggaagat ggaaaggtga actgctcaaa    1200
ttatatggtg gagatggctt gggtaaaaga aacatatggt gtgagcacat cagaagcaat    1260
ggcactcttg gaagactttt tgtgtatgag cccagacaag gacggacgtg tgaatgcgca    1320
agattttttgg gctcattttg gccttaattg caccccctctt tgcaagaaga tatttcagta    1380
cttcgatttt gaagccaagg aatccatcac attccgtcag ttcttgattg gatgtgcgca    1440
cctcaggaag cagccatcgt ttcaggacgc ctgcgaaacc gcgtttgaga ggtgtaggaa    1500
tccccctaaca tctcacatcg gcaggagca gctcgccgat gtcctgcggt caagcatgct    1560
tgagctgatg accgataatg ggatgatgaa gctgttcaag acgttggacg tcgacgatga    1620
cgacggaatc agcaaggatg acctgatggc atcccttagg aagctcccct tcatgatcgc    1680
gctcttcgcg ggccggatca acggggaagt ctacatcgag atagtttgat cgactggatt    1740
gatcgcaggg gagagcaaaa atggtggatg ggagtttgta acgcggtggg agacgacaga    1800
cctccgtctg ttttttagagg gatggtttcc aaccgcttca ccgtccatgt agctttctca    1860
ggcgtgttgg actaaagtgg ctaaccggta tagtgcgcaa ttttgtttca tatcgtaaaa    1920
atatatattt atatccatag aaaagctgtc gcgtgatggc acgctggatt gtgcaatgtg    1980
gatatgatac tgtacaacat tggtccaact gggcgtgcac atagaaactc ttttttttggt    2040
ttggtttggt ttggctaact ggatggatga ttacaaactc cttttggct aaaaaaaaaa    2100
aaaaaaaaaa aaaaa                                                    2115
```

<210> SEQ ID NO 42
<211> LENGTH: 255
<212> TYPE: PRT
<213> ORGANISM: Oryza sativa

<400> SEQUENCE: 42

```
Met Ala Ser Arg Asn Pro Ser Pro Ala Ser Leu Ser Thr Pro Leu Leu
  1               5                  10                  15

Ser Asp Ser Ile Ser Pro Thr Pro Thr Thr Asn Gly His Ala Gly His
             20                  25                  30

His Asn His Asp Asp Asp Glu Glu Ser Pro Thr Val Cys Gly Gly
         35                  40                  45

Asp Gly Gly Gly Gly Asp Pro Phe Ala Phe Leu Ser Glu Asp Arg
     50                  55                  60

Pro Ala Trp Trp Ser Pro Arg Gly Val Ser Pro Ala Asp Pro Phe Arg
 65                  70                  75                  80

Asn Gly Thr Pro Gly Trp Cys Gly Ala Tyr Glu Leu Val Arg Ala Leu
                 85                  90                  95

Val Cys Ala Pro Val Ala Ala Ala Arg Leu Val Leu Phe Gly Leu Ser
            100                 105                 110

Ile Ala Val Gly Tyr Ala Ala Thr Trp Val Ala Leu Arg Gly Trp Val
            115                 120                 125

Asp Val Arg Glu Arg Ala Ala Gln Glu Gly Ala Gly Pro Met Pro Ala
130                 135                 140

Trp Arg Arg Arg Leu Met Trp Ile Thr Arg Ile Ser Ala Arg Cys Ile
145                 150                 155                 160

Leu Phe Ser Phe Gly Tyr His Trp Ile Arg Arg Lys Gly Lys Pro Ala
                165                 170                 175

Pro Arg Glu Leu Ala Pro Ile Val Val Ser Asn His Val Ser Tyr Ile
            180                 185                 190

Glu Pro Ile Tyr Phe Phe Tyr Glu Leu Phe Pro Thr Ile Val Ser Ser
            195                 200                 205

Asp Ser His Asp Ser Ile Pro Phe Val Gly Thr Ile Ile Arg Ala Met
        210                 215                 220

Gln Val Ile Tyr Val Asp Arg Phe Ser Pro Ala Ser Arg Lys Ser Ala
225                 230                 235                 240

Val Asn Glu Ile Lys Asp Val Ile Ser Glu Lys Gly Gly Leu Gln
                245                 250                 255
```

<210> SEQ ID NO 43
<211> LENGTH: 2041
<212> TYPE: DNA
<213> ORGANISM: Glycine max

<400> SEQUENCE: 43

```
gcacgaggcg acgacgacga cttctccgtg ccgccaccgt ccaccctgga cccgttccgc     60
aaccgcacgc cggcgatcga gggctctac gagtgggcca agacggcgct gtgcctgccg    120
ctggcggcgc tgcggctcgc gctgttcggg ctctgcctcg cggtggggta cgtggcgacg    180
aaggtggcgc tggcagggtg gaaggacaag gagaatccca tgcccaagtg gaggtgtagg    240
gttatgtgga tcacgcgctt gtgcgccaga tgtattctct ctcctttggg ctatcagtgg    300
ataaaacgga aaggaaaaacc tgcaccaagg gaaattgctc caataattgt atctaaccat    360
gtttcttata ttgagcctat cttctatttc tatgaattat ttcctaccat tgtggcagct    420
gagtctcatg actccatacc ttttgttggc accattatta gagcaatgca ggtcatatat    480
gttaacagat tcttaccatc atcaaggaag caggctgtta gggaaataaa gaaatctgct    540
ttcaaggaac tgaataacag agaagggcct cttgtgataa atttcctcga gtactattat    600
ttcccgaggg aacaacaact aatggcagga accttatctc cttccaactt ggtgcattta    660
```

```
tccctggata cccaatccag cctgtaatta tacgctatcc tcatgtacac tttgaccaat    720
cctggggtaa tgtttctttg ggaaagctta tgttcagaat gttcactcaa tttcacaact    780
tttttgaggt agaatatctt cctgtcattt atcccctgga tgataaggaa actgctgtac    840
attttcggga gaggactagc cgtgctatcg caactgcact aaatgctgtc cagacaggac    900
attcttatgg agacataatg cttcatatga agcacaaga agcaaaacag agaaccccct     960
caagttttat ggttgaaatg accaaggtgg aatcattatt tcatatcagc agcacggaag   1020
ctgtggactt tctggataaa ttcttggcca tgaatcctga tcccagtggt cgtgttcaat   1080
atcatgactt cttgagggtt ttaagactta aggcttgccc actatctgca agatatttt    1140
cattcattga tgtggagaag agtgggacaa ttacgttcag acagttcttg tatggatctg   1200
cccatgttat gtcccaacct gggttcgatc aaacctttga agaagccttt gctggctgtg   1260
gcggtgcagt aaagacctat gttgttgaac aagagttacg agatttcatc caacctgcta   1320
tcctcaattg gagtgaggat gaggtccatg agttttttat gttatttgac aatgataatg   1380
atggaagaat tgacaagaat gactttcttt catgccttag aagaaatcct cttctcatag   1440
catttttttac acctcagcca cagcaaaaag aatttgaagg taatggagtg atagaaatag   1500
tgtgatggat ggatttcaca ttcaggtctt ttgtggacta caagaaaag aaatgggtag    1560
ggattcctgg ggaatacata cagtatagga tgcagtggcc tcattttttt tttttttcc    1620
ttttctcttt taattttttt accttgctct gattaattac tcgtaaagca taactatttg   1680
gtgaagatct gtgccatcca tcctgcttca tttgatgttt tttgttagct aggtcagttt   1740
tgcacagcta gatgtcagtt acctggatgt tgtgatcaca ccgatccaac atttgagttt   1800
tggttcaggg accatgctga catttagggt ccatgtggtt catgtaaagt ttgaaccaac   1860
gtgtcaattt gtaacaaaca ttataactgt atttttttc aaagatgtga acatgaagaa    1920
agtaatgtaa tttatttgga aaaaaaaaa aaaaaaaaaa aaaaaaaaaa aaaactcgag    1980
gggggggcccg ttgttttcg aggtcgacgt gctcgataag attgtatcca caccgagcgc   2040
g                                                                    2041
```

<210> SEQ ID NO 44
<211> LENGTH: 228
<212> TYPE: PRT
<213> ORGANISM: Glycine max

<400> SEQUENCE: 44

```
Ala Arg Gly Asp Asp Asp Phe Ser Val Pro Pro Ser Thr Leu
 1               5                  10                  15

Asp Pro Phe Arg Asn Arg Thr Pro Ala Ile Glu Gly Leu Tyr Glu Trp
            20                  25                  30

Ala Lys Thr Ala Leu Cys Leu Pro Leu Ala Ala Leu Arg Leu Ala Leu
        35                  40                  45

Phe Gly Leu Cys Leu Ala Val Gly Tyr Val Ala Thr Lys Val Ala Leu
    50                  55                  60

Ala Gly Trp Lys Asp Lys Glu Asn Pro Met Pro Lys Trp Arg Cys Arg
65                  70                  75                  80

Val Met Trp Ile Thr Arg Leu Cys Ala Arg Cys Ile Leu Phe Ser Phe
                85                  90                  95

Gly Tyr Gln Trp Ile Lys Arg Lys Gly Lys Pro Ala Pro Arg Glu Ile
            100                 105                 110

Ala Pro Ile Ile Val Ser Asn His Val Ser Tyr Ile Glu Pro Ile Phe
```

```
                    115                 120                 125
Tyr Phe Tyr Glu Leu Phe Pro Thr Ile Val Ala Glu Ser His Asp
    130                 135                 140

Ser Ile Pro Phe Val Gly Thr Ile Ile Arg Ala Met Gln Val Ile Tyr
145                 150                 155                 160

Val Asn Arg Phe Leu Pro Ser Ser Arg Lys Gln Ala Val Arg Glu Ile
                165                 170                 175

Lys Lys Ser Ala Phe Lys Glu Leu Asn Asn Arg Glu Gly Pro Leu Val
                180                 185                 190

Ile Asn Phe Leu Glu Tyr Tyr Tyr Phe Pro Arg Glu Gln Gln Leu Met
                195                 200                 205

Ala Gly Thr Leu Ser Pro Ser Asn Leu Val His Leu Ser Leu Asp Thr
    210                 215                 220

Gln Ser Ser Leu
225

<210> SEQ ID NO 45
<211> LENGTH: 1502
<212> TYPE: DNA
<213> ORGANISM: Zea mays

<400> SEQUENCE: 45
gcacgaggtc gtcctcacca tgccgatccg gcgtcagcgc tagggttagg gtctcctctg      60
cgcctttatc gccatggctc ctaacgaagc cgctagcatc accacccgt ccgagccgga     120 gagcgtgggc ggcagtgaga tgagcagcga agacatggcc gccgccagtc cgctcctctc     180
gtcgtcctcc ccctcccctt ccccctccgc agccccggtg ctggagagca tagaggaact     240
ggaccggaag tacgcaccgt acgcgcggcg ggacgcgtac ggaccgatgg ggctcggccc     300
cgtgagcgca gcggaggctg cgcggctggc gtttgccgcg gtcgtgctgg tcccgctccg     360
tgtcgtggca ggtgttctcg tactcgtggt ctactacctc gtgtgccgcg tgtgcacgct     420
gcgggtggag gaggaccggg agggcggcga aggggatggg tacgcgcggt tggacgggtg     480
gaggcgggcg ggggctgtgc ggtgcggccg cgcactcgct cgcgccatgt tgtttgtctt     540
cgggttctat tggatccgag agtacgacag ccgccttccc aatgctgagg atggccatgt     600
ggaccagtct aaagaaatcg aaaggcctgg ggcaattgtg tctaatcatg tatcttatgt     660
ggatattctt tatcacatgt cagcctcttt tcctagtttt gttgctaaga gatcagtggc     720
tagattgcct ctagttggtc tcataagcaa atgtcttgga tgcattttg ttcagcggga     780 gtcgaaaaca ccagatttca aggtgtttc aggtgctgta tctgaaagaa tccatcgtgc     840
tcatcaacag aaaaatgcac caatgatgct actcttccct gagggcacaa ctacaaatgg     900
ggattatctc cttccattca aaacaggtgc ttttcttgca aaggcaccag ttcaaccagt     960
cattttgaga tatccttaca aaagatttaa tgcagcatgg gattccatgt caggggcacg    1020
tcatgtattt ctgctgctct gtcaatttgt aaattaccta gaggtggtcc gcttaccagt    1080
ttactatcct tctgagcaag aaaaggatga tcctaagctc tatgcaaaca atgtacggaa    1140
actgatggca gtggagggaa acttgattct ttcagacctt gggctggcgg agaagcgagt    1200
gtaccatgcc gcactgaatg gtaatagtct agctcgtgct ttacatcaga agatgattg    1260 aaatgccatg ctatcgtgct tccataatac tggcttgctt gtaactgtgt gcttgcttgt    1320
gcatcgtcat ggttgagagg aatgtcgtga atatactatc cggcataaat ctgtaaagta    1380
atttaccaac tgtcatagtt cagtaattat gttggttata ctcctacatg gttgggcatc    1440
```

```
cgcacatttg atcctgtggt caatccatgt gagccttttt tactaaaaaa aaaaaaaaaa    1500
aa                                                                   1502
```

<210> SEQ ID NO 46
<211> LENGTH: 395
<212> TYPE: PRT
<213> ORGANISM: Zea mays

<400> SEQUENCE: 46

```
Met Ala Pro Asn Glu Ala Ala Ser Ile Thr Thr Pro Ser Glu Pro Glu
  1               5                  10                  15

Ser Val Gly Gly Ser Glu Met Ser Ser Glu Asp Met Ala Ala Ala Ser
             20                  25                  30

Pro Leu Leu Ser Ser Ser Ser Pro Ser Pro Ser Pro Ser Ala Ala Pro
         35                  40                  45

Val Leu Glu Ser Ile Glu Glu Leu Asp Arg Lys Tyr Ala Pro Tyr Ala
     50                  55                  60

Arg Arg Asp Ala Tyr Gly Pro Met Gly Leu Gly Pro Val Ser Ala Ala
 65                  70                  75                  80

Glu Ala Ala Arg Leu Ala Phe Ala Ala Val Val Leu Val Pro Leu Arg
                 85                  90                  95

Val Val Ala Gly Val Leu Val Leu Val Val Tyr Tyr Leu Val Cys Arg
            100                 105                 110

Val Cys Thr Leu Arg Val Glu Glu Asp Arg Glu Gly Gly Glu Gly Asp
        115                 120                 125

Gly Tyr Ala Arg Leu Asp Gly Trp Arg Arg Ala Gly Ala Val Arg Cys
    130                 135                 140

Gly Arg Ala Leu Ala Arg Ala Met Leu Phe Val Phe Gly Phe Tyr Trp
145                 150                 155                 160

Ile Arg Glu Tyr Asp Ser Arg Leu Pro Asn Ala Glu Asp Gly His Val
                165                 170                 175

Asp Gln Ser Lys Glu Ile Glu Arg Pro Gly Ala Ile Val Ser Asn His
            180                 185                 190

Val Ser Tyr Val Asp Ile Leu Tyr His Met Ser Ala Ser Phe Pro Ser
        195                 200                 205

Phe Val Ala Lys Arg Ser Val Ala Arg Leu Pro Leu Val Gly Leu Ile
    210                 215                 220

Ser Lys Cys Leu Gly Cys Ile Phe Val Gln Arg Glu Ser Lys Thr Pro
225                 230                 235                 240

Asp Phe Lys Gly Val Ser Gly Ala Val Ser Glu Arg Ile His Arg Ala
                245                 250                 255

His Gln Gln Lys Asn Ala Pro Met Met Leu Leu Phe Pro Glu Gly Thr
            260                 265                 270

Thr Thr Asn Gly Asp Tyr Leu Leu Pro Phe Lys Thr Gly Ala Phe Leu
        275                 280                 285

Ala Lys Ala Pro Val Gln Pro Val Ile Leu Arg Tyr Pro Tyr Lys Arg
    290                 295                 300

Phe Asn Ala Ala Trp Asp Ser Met Ser Gly Ala Arg His Val Phe Leu
305                 310                 315                 320

Leu Leu Cys Gln Phe Val Asn Tyr Leu Glu Val Val Arg Leu Pro Val
                325                 330                 335

Tyr Tyr Pro Ser Glu Gln Glu Lys Asp Asp Pro Lys Leu Tyr Ala Asn
            340                 345                 350

Asn Val Arg Lys Leu Met Ala Val Glu Gly Asn Leu Ile Leu Ser Asp
```

```
                355              360              365
Leu Gly Leu Ala Glu Lys Arg Val Tyr His Ala Ala Leu Asn Gly Asn
        370              375              380

Ser Leu Ala Arg Ala Leu His Gln Lys Asp Asp
385              390              395

<210> SEQ ID NO 47
<211> LENGTH: 1555
<212> TYPE: DNA
<213> ORGANISM: Oryza sativa

<400> SEQUENCE: 47
gcacgaggtt taaaccacgt ctcgtcgcca tctcctcatg cctacccact gctagggttt      60
gcccctaagc cccccaccct ctccgccatg gctctccctc tccacgacgc caccacctcc     120
ccctccgacc ccgacgacct cggcggcggc ggcgaggagg aggaggagag gctcgcctcg     180
aagccgctgc tctcgtcccc gtccacctat ccttccgcgg ggacggagga gggcgtcgag     240
gagctggagc tcgaccggag gtacgcgccg tacgcgaggc gggacgcgta cggggcgatg     300
ggccggggcc ccctgggcgc ggcggggggcg gggcggctgg cggtgggcgc cgccgtgctc     360
ttcccgctcc ggctcgccgc gggcgtgctc gtgctcgtcg cctactacct cgtgtgccgc     420
gtgtgcacgc tgcgtgtgga ggaggaggag cgcgagggtg gcggtggcgg cgcggctgga     480
gaagtggagg gggacgggta cgcgcggctc gaggggtgga ggcgtgaggg cgtcgtgcgg     540
tgcggccgcg cgctcgcgcg cgccatgctg ttcgtcttcg gcttctactg gatccgcgag     600
tacgactgcc gcttccctga tgctgaggat gagcatcagg aacagtccaa agaattggga     660
agaccagggg cagtagtatc taatcatgta tcttatgtgg atattcttta ccacatgtca     720
tcttccttcc aagctttgt tgccaagaga tcagtggcca gattgcccat ggttggtctc     780
ataagcaaat gtcttggatg cattttttgtt cagcgggaat ctaaaacctc agatttcaaa     840
ggcgtttcag gtgctgtgac tgagagaatc caacgggctc atcaacagaa gaattctcca     900
atgatgctac ttttccctga aggcacaact acaaatggtg attatctcct ccctttcaag     960
acaggagcat ttcttgcaaa agcaccagtg aagccagtca ttttaagata tccttacaag    1020
agatttagtc cagcatggga ttcgatgtct ggggctcggc atgtatttct gctcctttgt    1080
caatttgtaa ataaccttga ggtgatccat ttgcctgtgt attacccatc tgagcaagag    1140
aaggaagatc ctaagctgta cgcaaataat gtacggaaat tgatggcagt ggaggggaac    1200
ttgattcttt ctgatcttgg gctagcagag aagcgtgtgt accatgcggc attgaatggt    1260
aataatagtc tacctcgtgc tttacatcag aaagatgatt gaaatgcctt gccatcgcgc    1320
ttctgtatac tgatgctgag tgacttgctt gtaatatgag tacaagttcc tggtgttgca    1380
tgattcctca tgttgagagg agctatgtta atatcctccc agtaaactgt aaaattattt    1440
gtccatagtg tggttcagta atcatgtcag ttatacatga ttacattcac atgtctggga    1500
cacacttcac catgcaatcc atcgatgtga gctttataaa aaaaaaaaaa aaaaa         1555

<210> SEQ ID NO 48
<211> LENGTH: 404
<212> TYPE: PRT
<213> ORGANISM: Oryza sativa

<400> SEQUENCE: 48

Met Ala Leu Pro Leu His Asp Ala Thr Thr Ser Pro Ser Asp Pro Asp
1               5                  10                  15
```

```
Asp Leu Gly Gly Gly Gly Glu Glu Glu Glu Arg Leu Ala Ser Lys
         20                  25                  30

Pro Leu Leu Ser Ser Pro Ser Thr Tyr Pro Ser Ala Gly Thr Glu Glu
             35                  40                  45

Gly Val Glu Glu Leu Glu Leu Asp Arg Arg Tyr Ala Pro Tyr Ala Arg
     50                  55                  60

Arg Asp Ala Tyr Gly Ala Met Gly Arg Gly Pro Leu Gly Ala Ala Gly
 65                  70                  75                  80

Ala Gly Arg Leu Ala Val Gly Ala Ala Val Leu Phe Pro Leu Arg Leu
                 85                  90                  95

Ala Ala Gly Val Leu Val Leu Val Ala Tyr Tyr Leu Val Cys Arg Val
            100                 105                 110

Cys Thr Leu Arg Val Glu Glu Glu Arg Glu Gly Gly Gly Gly
            115                 120                 125

Ala Ala Gly Glu Val Glu Gly Asp Gly Tyr Ala Arg Leu Glu Gly Trp
        130                 135                 140

Arg Arg Glu Gly Val Val Arg Cys Gly Arg Ala Leu Ala Arg Ala Met
145                 150                 155                 160

Leu Phe Val Phe Gly Phe Tyr Trp Ile Arg Glu Tyr Asp Cys Arg Phe
                165                 170                 175

Pro Asp Ala Glu Asp Glu His Gln Glu Gln Ser Lys Glu Leu Gly Arg
            180                 185                 190

Pro Gly Ala Val Val Ser Asn His Val Ser Tyr Val Asp Ile Leu Tyr
        195                 200                 205

His Met Ser Ser Ser Phe Pro Ser Phe Val Ala Lys Arg Ser Val Ala
    210                 215                 220

Arg Leu Pro Met Val Gly Leu Ile Ser Lys Cys Leu Gly Cys Ile Phe
225                 230                 235                 240

Val Gln Arg Glu Ser Lys Thr Ser Asp Phe Lys Gly Val Ser Gly Ala
                245                 250                 255

Val Thr Glu Arg Ile Gln Arg Ala His Gln Gln Lys Asn Ser Pro Met
            260                 265                 270

Met Leu Leu Phe Pro Glu Gly Thr Thr Thr Asn Gly Asp Tyr Leu Leu
        275                 280                 285

Pro Phe Lys Thr Gly Ala Phe Leu Ala Lys Ala Pro Val Lys Pro Val
    290                 295                 300

Ile Leu Arg Tyr Pro Tyr Lys Arg Phe Ser Pro Ala Trp Asp Ser Met
305                 310                 315                 320

Ser Gly Ala Arg His Val Phe Leu Leu Leu Cys Gln Phe Val Asn Asn
                325                 330                 335

Leu Glu Val Ile His Leu Pro Val Tyr Tyr Pro Ser Glu Gln Glu Lys
            340                 345                 350

Glu Asp Pro Lys Leu Tyr Ala Asn Asn Val Arg Lys Leu Met Ala Val
        355                 360                 365

Glu Gly Asn Leu Ile Leu Ser Asp Leu Gly Leu Ala Glu Lys Arg Val
    370                 375                 380

Tyr His Ala Ala Leu Asn Gly Asn Asn Ser Leu Pro Arg Ala Leu His
385                 390                 395                 400

Gln Lys Asp Asp

<210> SEQ ID NO 49
<211> LENGTH: 1072
<212> TYPE: DNA
<213> ORGANISM: Glycine max
```

<400> SEQUENCE: 49

```
gcacgaggga agattacgct catatgagtg ggttgaggag aaccgtcatt gtttcgtgtg      60
gacgcgccct ctccagagtc atgctcttca ttttcggctt ttattggatc cccgaatcca     120
actctgcctc tcaggaagac cggagtcagc ctgaagagtt ggggagacct agcgtaataa     180
tatctaatca tgtgtcatac ttggatattt gtatcacat gtcgtcctca ttcccaagtt      240
ttgttgctaa gagatcagtg gctaaacttc cgctcattgg tctcatcagc aagtgccttg     300
gttgtgtgta tgttcagcgg gaatcaaagt catcggactt caagggtgtt tcagctgttg     360
tcactgacag aattcaagaa gctcatcaga atgagtctgc tccattaatg atgttatttc     420
cagaaggaac aaccacaaat ggagagttcc tccttccatt caagactggt ggttttttgg     480
caaaggcacc agtacttcct gtgattttaa gatatcatta ccagagattt agccccgcct     540
gggattccat atctggggtg cgccatgtaa tatttctcct gtgtcagttt gtgaattata     600
tggaggtgat ccgagtacct gtttaccatc cctcacagca ggagatgaat gatcccaaac     660
tatatgctaa taatgttaga aggttgatgg ctactgaggg taatttgata ctttctgata     720
ttgggttagc tgaaaaacga atatatcacg ctgctctcaa tggtaataat agcatgccta     780
gtgttttgca tcagaaagac gaatgataat ttcatggccc ccgtctcaaa tgaaatgtag     840
ttccagtcga gttttagttt caaacttagt atctgtttat gaatggacag cttgtgtgaa     900
gggtatagct aaatagtata cattcaccta aacatctgaa tggtacttgt gtaattttct     960
tgtaaataac gtgaccaata atgttttaat tgctggtgaa ctcaatttga ggcacacaat    1020
tcaagatcta aagtttaac tgttcttcgt tcaaaaaaaa aaaaaaaaaa aa             1072
```

<210> SEQ ID NO 50  
<211> LENGTH: 267  
<212> TYPE: PRT  
<213> ORGANISM: Glycine max

<400> SEQUENCE: 50

```
Thr Arg Glu Asp Tyr Ala His Met Ser Gly Leu Arg Arg Thr Val Ile
  1               5                  10                  15

Val Ser Cys Gly Arg Ala Leu Ser Arg Val Met Leu Phe Ile Phe Gly
             20                  25                  30

Phe Tyr Trp Ile Pro Glu Ser Asn Ser Ala Ser Gln Glu Asp Arg Ser
         35                  40                  45

Gln Pro Glu Glu Leu Gly Arg Pro Ser Val Ile Ser Asn His Val
     50                  55                  60

Ser Tyr Leu Asp Ile Leu Tyr His Met Ser Ser Phe Pro Ser Phe
 65                  70                  75                  80

Val Ala Lys Arg Ser Val Ala Lys Leu Pro Leu Ile Gly Leu Ile Ser
             85                  90                  95

Lys Cys Leu Gly Cys Val Tyr Val Gln Arg Glu Ser Lys Ser Ser Asp
            100                 105                 110

Phe Lys Gly Val Ser Ala Val Val Thr Asp Arg Ile Gln Glu Ala His
        115                 120                 125

Gln Asn Glu Ser Ala Pro Leu Met Met Leu Phe Pro Glu Gly Thr Thr
    130                 135                 140

Thr Asn Gly Glu Phe Leu Leu Pro Phe Lys Thr Gly Gly Phe Leu Ala
145                 150                 155                 160

Lys Ala Pro Val Leu Pro Val Ile Leu Arg Tyr His Tyr Gln Arg Phe
                165                 170                 175
```

Ser Pro Ala Trp Asp Ser Ile Ser Gly Val Arg His Val Ile Phe Leu
            180                 185                 190

Leu Cys Gln Phe Val Asn Tyr Met Glu Val Ile Arg Val Pro Val Tyr
        195                 200                 205

His Pro Ser Gln Gln Glu Met Asn Asp Pro Lys Leu Tyr Ala Asn Asn
    210                 215                 220

Val Arg Arg Leu Met Ala Thr Glu Gly Asn Leu Ile Leu Ser Asp Ile
225                 230                 235                 240

Gly Leu Ala Glu Lys Arg Ile Tyr His Ala Ala Leu Asn Gly Asn Asn
                245                 250                 255

Ser Met Pro Ser Val Leu His Gln Lys Asp Glu
            260                 265

<210> SEQ ID NO 51
<211> LENGTH: 838
<212> TYPE: DNA
<213> ORGANISM: Glycine max
<220> FEATURE:
<221> NAME/KEY: unsure
<222> LOCATION: (205)
<223> OTHER INFORMATION: n = a, c, g, or t
<220> FEATURE:
<221> NAME/KEY: unsure
<222> LOCATION: (779)
<223> OTHER INFORMATION: n = a, c, g, or t
<220> FEATURE:
<221> NAME/KEY: unsure
<222> LOCATION: (814)
<223> OTHER INFORMATION: n = a, c, g, or t

<400> SEQUENCE: 51
gagagaacta gtctcagcca ttttccattt ctttccactt ttatgttttc aggtcatata      60
tgttaacaga ttcttaccat catcaaggaa gcaggctgtt agggaaataa agagaagggc     120
ctcttgcaat agatttcctc gagtactatt atttcccgag ggaacaacaa caaatggcag     180
gaaccttatc tccttccaac ttggngcatt tatccctgga tacccaatcc agcctgtaat     240
tgtacgctat cctcatgtgc actttgacca atcctgggt catgtttctt tgggaaagct     300
tatgttcaga atgttcactc aatttcacaa cttttttgag gtagaatatc ttcctgtcat     360
ttatcccctg gatgataagg aaactgctgt acattttcgg gagaggacta gccgtgctat     420
cgcaactgca ctaaatgctg tccagacagg acattcttat ggagacataa tgcttcatat     480
gaaagcacaa gaagcaaaac aggagaaccc ctcaagtttt atggttgaaa tgaccaaggt     540
ggaatcagtg agtccctaaa agcaaatgac cttaccattt cctttttttt tctgccattt     600
tcaagtccct tgtaaattat ctttttcttt aacttttaa gtaggatatt taggttaaac      660
cttttgaagt acatgcaaat gccacagtaa ccctttgctt atgccaatgg atgacagaca     720
taagtgaccc agggtggctg cataatgttg gggccttcta atctatggga aatatgtant     780
gaaaggggag aatatttaaa ttgtgatttg tggnaataag gggataatat gacataag      838

<210> SEQ ID NO 52
<211> LENGTH: 185
<212> TYPE: PRT
<213> ORGANISM: Glycine max

<400> SEQUENCE: 52

Arg Glu Leu Val Ser Ala Ile Phe His Phe Phe Pro Leu Leu Cys Phe
  1               5                  10                  15

Gln Val Ile Tyr Val Asn Arg Phe Leu Pro Ser Ser Arg Lys Gln Ala

```
                  20                  25                  30
Val Arg Glu Ile Lys Arg Arg Ala Ser Cys Asn Arg Phe Pro Arg Val
         35                  40                  45

Leu Leu Phe Pro Glu Gly Thr Thr Thr Asn Gly Arg Asn Leu Ile Ser
 50                  55                  60

Phe Gln Leu Gly Ala Phe Ile Pro Gly Tyr Pro Ile Gln Pro Val Ile
 65                  70                  75                  80

Val Arg Tyr Pro His Val His Phe Asp Gln Ser Trp Gly His Val Ser
                 85                  90                  95

Leu Gly Lys Leu Met Phe Arg Met Phe Thr Gln Phe His Asn Phe Phe
                100                 105                 110

Glu Val Glu Tyr Leu Pro Val Ile Tyr Pro Leu Asp Asp Lys Glu Thr
            115                 120                 125

Ala Val His Phe Arg Glu Arg Thr Ser Arg Ala Ile Ala Thr Ala Leu
130                 135                 140

Asn Ala Val Gln Thr Gly His Ser Tyr Gly Asp Ile Met Leu His Met
145                 150                 155                 160

Lys Ala Gln Glu Ala Lys Gln Glu Asn Pro Ser Ser Phe Met Val Glu
                165                 170                 175

Met Thr Lys Val Glu Ser Val Ser Pro
                180                 185

<210> SEQ ID NO 53
<211> LENGTH: 1632
<212> TYPE: DNA
<213> ORGANISM: Oryza sativa

<400> SEQUENCE: 53
cttctcgtcg ccggtggatt cgccgccgcc tccgccgccg ccgccggagg aggaggacga      60
ggagagggcg ctccctcggg ggtgagcatc cagccacctc ggcccgttgc ctcctcttcg     120
catctcggcc ccgcgagatt ggaagtgagg gcagggcagg gcggcagggg ccatggcggt     180
cccactcgtg ctcgtcgtgc tcccgctcgg cctcctcttc ctcctctccg gcctcatcat     240
caacgccatc caggccgtcc tgtttctctc gataaggccg ttctcgaaga gcttgtaccg     300
gcggatcaac aggttcttgg ccgagctgct gtggcttcag ctggtctggc ttgtggattg     360
gtgggcagga gttaagatac aactgcatgc tgatgacgaa acttacaagg caatggggaa     420
tgagcatgca cttgtcatat caaataatcg gagcgatatc gattggctta ttgggtggat     480
tttggcacag cgctcaggat gccttggaag tacacttgct gttatgaaga atcatcgaa     540 attccttcca gttattggct ggtccatgtg gtttgcagaa tacctctttt tggaaaggag     600
ctgggcaaag gatgaaaaga cattgaaatg gggcctccaa aggttgaagg acttccccag     660
accattttgg ctagcccttt tgttgagggg cactcgcttt actccagcaa agcttctagc     720
agctcaggag tatgctgttt cacagggttt gccagcaccc agaaatgtat tgattccacg     780
tacaaaggga tttgtatcag ctgtaactat tatgcgggat tttgttccag ctatttatga     840
tacaacagta attattccaa aagattcacc tcaaccaaca atgctgcgga ttttgaaagg     900
gcaatcttca gtggtacatg ttcgcatgaa acgtcatgca atgagtgaga tgccaaagtc     960
agaagacgat gtttcaaaat ggtgcaaaga catctttgta gcaaaggatg cattactgga    1020
taagcatttg gcgacaggca cttttgatga ggagattaga ccaattggcc gcccagtaaa    1080
atcattgctg gtgactttgt tttggtcatg tctccttta tatggcgccg tcaagctctt    1140
cctatggact caactcctgt cgacatggaa aggagtcggg tttacgggcc ttgggctcgc    1200
```

-continued

```
actggtgacg gcggtcatgc atgtcttcat catgttctcg cagtcagagc gatcgagctc    1260
agccaaggcg gctcggaacc gtgtcaagaa agattgaaag agatgaagat agagtctgca    1320
gcttatcaat gggagctacc aattaattgg gtattgaatt catgtaggca acaaaattga    1380
gggcctaatc tttcctgtat aatgcaccaa aagggttctt acagaactga atgcctgaat    1440
agagagattc taggagattt ggtgaactag caactctgag ctctgttgtg ctgtattttc    1500
agagaatgtt ttttttggca gaacaggaat tgtactactt gtatttattg gaacttctac    1560
atcagtctgg atttgttcag aagaccttta gtgatttatg tatcagtgaa acttaaaaaa    1620
aaaaaaaaaa aa                                                         1632
```

<210> SEQ ID NO 54
<211> LENGTH: 374
<212> TYPE: PRT
<213> ORGANISM: Oryza sativa

<400> SEQUENCE: 54

```
Met Ala Val Pro Leu Val Leu Val Val Leu Pro Leu Gly Leu Leu Phe
  1               5                  10                  15

Leu Leu Ser Gly Leu Ile Ile Asn Ala Ile Gln Ala Val Leu Phe Leu
             20                  25                  30

Ser Ile Arg Pro Phe Ser Lys Ser Leu Tyr Arg Arg Ile Asn Arg Phe
         35                  40                  45

Leu Ala Glu Leu Leu Trp Leu Gln Leu Val Trp Leu Val Asp Trp Trp
     50                  55                  60

Ala Gly Val Lys Ile Gln Leu His Ala Asp Asp Glu Thr Tyr Lys Ala
 65                  70                  75                  80

Met Gly Asn Glu His Ala Leu Val Ile Ser Asn Asn Arg Ser Asp Ile
                 85                  90                  95

Asp Trp Leu Ile Gly Trp Ile Leu Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ala Glu Tyr Leu Phe Leu Glu Arg Ser Trp
    130                 135                 140

Ala Lys Asp Glu Lys Thr Leu Lys Trp Gly Leu Gln Arg Leu Lys Asp
145                 150                 155                 160

Phe Pro Arg Pro Phe Trp Leu Ala Leu Phe Val Glu Gly Thr Arg Phe
                165                 170                 175

Thr Pro Ala Lys Leu Leu Ala Ala Gln Glu Tyr Ala Val Ser Gln Gly
            180                 185                 190

Leu Pro Ala Pro Arg Asn Val Leu Ile Pro Arg Thr Lys Gly Phe Val
        195                 200                 205

Ser Ala Val Thr Ile Met Arg Asp Phe Val Pro Ala Ile Tyr Asp Thr
    210                 215                 220

Thr Val Ile Ile Pro Lys Asp Ser Pro Gln Pro Thr Met Leu Arg Ile
225                 230                 235                 240

Leu Lys Gly Gln Ser Ser Val Val His Val Arg Met Lys Arg His Ala
                245                 250                 255

Met Ser Glu Met Pro Lys Ser Glu Asp Val Ser Lys Trp Cys Lys
            260                 265                 270

Asp Ile Phe Val Ala Lys Asp Ala Leu Leu Asp Lys His Leu Ala Thr
        275                 280                 285
```

```
Gly Thr Phe Asp Glu Glu Ile Arg Pro Ile Gly Arg Pro Val Lys Ser
    290                 295                 300

Leu Leu Val Thr Leu Phe Trp Ser Cys Leu Leu Leu Tyr Gly Ala Val
305                 310                 315                 320

Lys Leu Phe Leu Trp Thr Gln Leu Leu Ser Thr Trp Lys Gly Val Gly
                325                 330                 335

Phe Thr Gly Leu Gly Leu Ala Leu Val Thr Ala Val Met His Val Phe
                340                 345                 350

Ile Met Phe Ser Gln Ser Glu Arg Ser Ser Ser Ala Lys Ala Ala Arg
            355                 360                 365

Asn Arg Val Lys Lys Asp
    370
```

<210> SEQ ID NO 55
<211> LENGTH: 1498
<212> TYPE: DNA
<213> ORGANISM: Glycine max

<400> SEQUENCE: 55

```
gcacgaggtt ccgtttgctg acctgacctc ggaaatccaa agagggaaac tcacggtgtt      60
tcgttgcgtt gtgctctgct ctgctccttt gggcctgggc tgggctgggc tgggctgggc     120
tgggcatggc tattgcagca gcggccgtgg tggtaccatt gggcctgctc ttcttcgcct     180
ccggcctcct tgttaatctc attcaggcaa tatgctatgt cgtcgtaagg ccggtgtcga     240
aaagtttgta cagaaggatc aaccgggtag tagcagagct cttgtggctg agcttgtat      300
ggcttattga ttggtgggca ggagttaagg tccaaatatt cacagatcat gaaacctttc     360
gtttaatggg taaagagcat gcacttgtga taagcaatca cagaagtgat attgattggc     420
tgttggatgg gtttcagct cagcgttcag gttgtcttgg cagcactcta gctgtgatga     480
agaaatcttc aaagtttctg ccggtcattg gctggtcaat gtggttttct gagtatcttt     540
ttctggagag aagttgggcc aaggatgaaa gcacattaaa gtcaggcatc cagcgactga     600
gtgatttccc tcttcccttt tggctagctc tctttgtaga aggaacgcgt tttacacagg     660
ccaaactatt agctgctcag gaatatgcca cttccactgg attgcctgtt cctagaaatg     720
ttttgattcc aagaactaag ggttttgttt ctgcagtaag tcatatgcgc tcatttgttc     780
ctgccattta tgatgtaaca gtagccatcc ctaagagttc ccctgctcct acaatgctaa     840
gactcttcaa gggacaacct tcagtggtgc atgttcatat caagaggcat tgatgaagg      900
aactgccaga tacagatgag gctgttgctc aatggtgtcg agatatattt gtggccaagg     960
atgctttgtt agacaaacat atggctgagg gtacttttag tgatcaagag ctgcaggata    1020
ctggtcgacc aataaagtct cttctggtag ttatatcttg ggcgtgtctg gttgttgcgg    1080
ggtctgtaaa gttcctgcaa tggtcttcgt tactctcttc ctggaagggt gttgcatttt    1140
cagcttttgg tttggcagtt gttactgcac ttatgcaaat tctgattcaa ttctcacagt    1200
cagagcgttc aaacccggcc aagatcgtgc ctgcaaagtc aaaaaacaag gggtcttgat    1260
ttatttggcg aacttaaagt tgcatttatg tgtgatgagt gactcatgta atactccatta   1320
ttttgctttc aacatcttat catagtatgc ttctattcta tatatgtact attatgaatg    1380
cttatcgatt cattgttttt aatttaatta ggatatcctt ttgtattgac agtctagggg    1440
atggcctaga aaaattcaac cacctatttt attttaaaaa aaaaaaaaa aaaaaact       1498
```

<210> SEQ ID NO 56
<211> LENGTH: 377

```
<212> TYPE: PRT
<213> ORGANISM: Glycine max

<400> SEQUENCE: 56

Met Ala Ile Ala Ala Ala Val Val Pro Leu Gly Leu Leu Phe
 1               5                  10                  15

Phe Ala Ser Gly Leu Leu Val Asn Leu Ile Gln Ala Ile Cys Tyr Val
            20                  25                  30

Val Val Arg Pro Val Ser Lys Ser Leu Tyr Arg Arg Ile Asn Arg Val
        35                  40                  45

Val Ala Glu Leu Leu Trp Leu Glu Leu Val Trp Leu Ile Asp Trp Trp
    50                  55                  60

Ala Gly Val Lys Val Gln Ile Phe Thr Asp His Glu Thr Phe Arg Leu
 65                  70                  75                  80

Met Gly Lys Glu His Ala Leu Val Ile Ser Asn His Arg Ser Asp Ile
                85                  90                  95

Asp Trp Leu Val Gly Trp Val Ser Ala Gln Arg Ser Gly Cys Leu Gly
            100                 105                 110

Ser Thr Leu Ala Val Met Lys Lys Ser Ser Lys Phe Leu Pro Val Ile
        115                 120                 125

Gly Trp Ser Met Trp Phe Ser Glu Tyr Leu Phe Leu Glu Arg Ser Trp
    130                 135                 140

Ala Lys Asp Glu Ser Thr Leu Lys Ser Gly Ile Gln Arg Leu Ser Asp
145                 150                 155                 160

Phe Pro Leu Pro Phe Trp Leu Ala Leu Phe Val Glu Gly Thr Arg Phe
                165                 170                 175

Thr Gln Ala Lys Leu Leu Ala Ala Gln Glu Tyr Ala Thr Ser Thr Gly
            180                 185                 190

Leu Pro Val Pro Arg Asn Val Leu Ile Pro Arg Thr Lys Gly Phe Val
        195                 200                 205

Ser Ala Val Ser His Met Arg Ser Phe Val Pro Ala Ile Tyr Asp Val
    210                 215                 220

Thr Val Ala Ile Pro Lys Ser Ser Pro Ala Pro Thr Met Leu Arg Leu
225                 230                 235                 240

Phe Lys Gly Gln Pro Ser Val Val His Val His Ile Lys Arg His Leu
                245                 250                 255

Met Lys Glu Leu Pro Asp Thr Asp Glu Ala Val Ala Gln Trp Cys Arg
            260                 265                 270

Asp Ile Phe Val Ala Lys Asp Ala Leu Leu Asp Lys His Met Ala Glu
        275                 280                 285

Gly Thr Phe Ser Asp Gln Glu Leu Gln Asp Thr Gly Arg Pro Ile Lys
    290                 295                 300

Ser Leu Leu Val Val Ile Ser Trp Ala Cys Leu Val Val Ala Gly Ser
305                 310                 315                 320

Val Lys Phe Leu Gln Trp Ser Ser Leu Leu Ser Ser Trp Lys Gly Val
                325                 330                 335

Ala Phe Ser Ala Phe Gly Leu Ala Val Val Thr Ala Leu Met Gln Ile
            340                 345                 350

Leu Ile Gln Phe Ser Gln Ser Glu Arg Ser Asn Pro Ala Lys Ile Val
        355                 360                 365

Pro Ala Lys Ser Lys Asn Lys Gly Ser
    370                 375

<210> SEQ ID NO 57
```

<211> LENGTH: 1415
<212> TYPE: DNA
<213> ORGANISM: Triticum aestivum

<400> SEQUENCE: 57

```
gcacgaggag aggagacgcg gcggcggcca tggcgattcc cctcgtgctc gtcctgctcc      60
cgctcggcct cctcttcctc ctctccggcc tcgtcgtcaa cactgtccag gccgtattgt     120
tcttgacgat aaggccattc tcgaagcgat tgtaccggca gatcaacgta ttcctggccg     180
agttgttgtg gcttcagctg atctggcttg tggactggtg ggcaggtatt aaggtacagg     240
tgtatgcgga tccagaaact tggaaactaa tgggcaaaga gcacgccctt ctcatatcca     300
atcatcgaag tgacattgat tggctggttg gatggatttt agcacagcgt tcaggatgtc     360
ttggaagcgc aatagctata atgaagaaat cctcaaagtt ccttccagtt attggttggt     420
ccatgtggtt tgcagaatac ctcttttttgg agagaagctg ggcaaaggat gaaaaaacac     480
ttaaatcggg tcttcaaagg ttgaaagact tccccagatc attttggctt gcccttttg      540
ttgagggtac aagatttact ccagcaaaac ttttagcagc tcaagaatat gcagtctcac     600
agggtttgac agcgcctagg aatgtgctga ttccacgaac aaagggattt gtatcagctg     660
taagtattat gcgtgacttt gtcccagcta tctacgatac aacagtgatt attccggaag     720
attcgcctaa accaacaatg ctgcgtattc ttcaggaca atcatcagtt gttcatgtcc      780
gcataaaacg ccattcaatg agtgatatgc ctaactcgga tgaggatgtt tcaaaatggt     840
gcaaagatat atttgtagca aaggacgcgt tattggacaa acatatagca actggtactt     900
ttgatgagga aattatacca attggccgtc cagtgaaatc tttgatggtg gtcctgtctt     960
ggtcatgtct cctcctatat ggtgctcata gattcttaca gtggaccagg ctcttgtcga    1020
cgtggaaagg agtgatcctc tttgcttctg gattggcaat ggtaaccgcc gttatgcatg    1080
tattcatcat gttctcgcag gccgagcgct caagctctgc gaaagcagca agggaccgag    1140
tgaagaagga ttgatagctc gtgtgaaatt cagtctatag gggaactgcc aatttattat    1200
gttcagaata tatgtagaca caggctccat gggtcaaatc tagtatgtcc ttgttgtcct    1260
cggtaagagc ttcaggaatt ttgtgtggcg agaactgtga gctttcttcc ttctttctct    1320
actttgtaat gacttgtaaa gatttgcttt gccataccag gaatcgctgc tcgaatttat    1380
cgaagctttt ttttatcaaa aaaaaaaaaa aaaaa                               1415
```

<210> SEQ ID NO 58
<211> LENGTH: 374
<212> TYPE: PRT
<213> ORGANISM: Triticum aestivum

<400> SEQUENCE: 58

```
Met Ala Ile Pro Leu Val Leu Val Leu Leu Pro Leu Gly Leu Leu Phe
  1               5                  10                  15

Leu Leu Ser Gly Leu Val Val Asn Thr Val Gln Ala Val Leu Phe Leu
             20                  25                  30

Thr Ile Arg Pro Phe Ser Lys Arg Leu Tyr Arg Gln Ile Asn Val Phe
         35                  40                  45

Leu Ala Glu Leu Leu Trp Leu Gln Leu Ile Trp Leu Val Asp Trp Trp
     50                  55                  60

Ala Gly Ile Lys Val Gln Val Tyr Ala Asp Pro Glu Thr Trp Lys Leu
 65                  70                  75                  80

Met Gly Lys Glu His Ala Leu Leu Ile Ser Asn His Arg Ser Asp Ile
                 85                  90                  95
```

-continued

```
Asp Trp Leu Val Gly Trp Ile Leu Ala Gln Arg Ser Gly Cys Leu Gly
            100                 105                 110

Ser Ala Ile Ala Ile Met Lys Lys Ser Ser Lys Phe Leu Pro Val Ile
            115                 120                 125

Gly Trp Ser Met Trp Phe Ala Glu Tyr Leu Phe Leu Glu Arg Ser Trp
            130                 135                 140

Ala Lys Asp Glu Lys Thr Leu Lys Ser Gly Leu Gln Arg Leu Lys Asp
145                 150                 155                 160

Phe Pro Arg Ser Phe Trp Leu Ala Leu Phe Val Glu Gly Thr Arg Phe
                165                 170                 175

Thr Pro Ala Lys Leu Leu Ala Ala Gln Glu Tyr Ala Val Ser Gln Gly
            180                 185                 190

Leu Thr Ala Pro Arg Asn Val Leu Ile Pro Arg Thr Lys Gly Phe Val
            195                 200                 205

Ser Ala Val Ser Ile Met Arg Asp Phe Val Pro Ala Ile Tyr Asp Thr
210                 215                 220

Thr Val Ile Ile Pro Glu Asp Ser Pro Lys Pro Thr Met Leu Arg Ile
225                 230                 235                 240

Leu Gln Gly Gln Ser Ser Val Val His Val Arg Ile Lys Arg His Ser
                245                 250                 255

Met Ser Asp Met Pro Asn Ser Asp Glu Asp Val Ser Lys Trp Cys Lys
            260                 265                 270

Asp Ile Phe Val Ala Lys Asp Ala Leu Leu Asp Lys His Ile Ala Thr
            275                 280                 285

Gly Thr Phe Asp Glu Glu Ile Ile Pro Ile Gly Arg Pro Val Lys Ser
            290                 295                 300

Leu Met Val Val Leu Ser Trp Ser Cys Leu Leu Leu Tyr Gly Ala His
305                 310                 315                 320

Arg Phe Leu Gln Trp Thr Gln Leu Leu Ser Thr Trp Lys Gly Val Ile
                325                 330                 335

Leu Phe Ala Ser Gly Leu Ala Met Val Thr Ala Val Met His Val Phe
                340                 345                 350

Ile Met Phe Ser Gln Ala Glu Arg Ser Ser Ser Ala Lys Ala Ala Arg
            355                 360                 365

Asp Arg Val Lys Lys Asp
            370
```